(12) United States Patent
Yang et al.

(10) Patent No.: US 10,583,123 B2
(45) Date of Patent: Mar. 10, 2020

(54) METHOD FOR THE TREATMENT OF ATG4-RELATED DISORDERS

(71) Applicant: National Tsing Hua University, Hsinchu (TW)

(72) Inventors: Lee-Wei Yang, Tainan (TW); Chih-Wen Shu, Miaoli County (TW); Pei-Feng Liu, Taipei (TW); Kun-Lin Tsai, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/842,910

(22) Filed: Dec. 15, 2017

(65) Prior Publication Data

US 2019/0183860 A1     Jun. 20, 2019

(51) Int. Cl.
*A61K 31/4178*     (2006.01)
*A61K 31/351*      (2006.01)
*A61K 31/436*      (2006.01)
*A61K 45/06*       (2006.01)
*A61P 35/00*       (2006.01)

(52) U.S. Cl.
CPC ........ *A61K 31/4178* (2013.01); *A61K 31/351* (2013.01); *A61K 31/436* (2013.01); *A61K 45/06* (2013.01); *A61P 35/00* (2018.01)

(58) Field of Classification Search
CPC .............. A61K 31/4178; A61K 31/351; A61K 31/436; A61P 7/00
USPC ......................................................... 514/397
See application file for complete search history.

(56) References Cited

U.S. PATENT DOCUMENTS 4,766,140 A * 8/1988 Hirsch ................. A61K 31/415
514/396

FOREIGN PATENT DOCUMENTS

WO     2014/200705 A1    12/2014

OTHER PUBLICATIONS

Spring, Laura. printout of https://www.lbbc.org/learn/treatments-and-research/chemotherapy/types-chemotherapy/doxorubicin (Aug. 2015). (Year: 2015).*
Pei-Feng Liu et al., ATG4B promotes colorectal cancer growth independent of autophagic flux, Autophagy, Aug. 2014, pp. 1454-1465, vol. 10, No. 8.

(Continued)

*Primary Examiner* — Craig D Ricci
*Assistant Examiner* — Janet L. Coppins

(57) ABSTRACT

The present invention relates to the area of ATG4-related disorders. More particularly, the present invention relates to a method of treating an ATG4B-related disorder comprising a step of administering a subject with an effective amount of tioconazole. The present invention relates also to a method of increasing a subject's responsiveness to a therapy for a cancer comprising inhibition of ATG4B activity in cells; said method comprises administering the subject with an effective amount of tioconazole. The present invention also relates to a method for enhancing or inducing a response in a cancer cell consisting of cytotoxicity, chemosensitivity or starvation-sensitivity; said method comprises administering a subject with an effective amount of tioconazole to inhibit ATG4B's activity.

6 Claims, 76 Drawing Sheets
(37 of 76 Drawing Sheet(s) Filed in Color)

Specification includes a Sequence Listing.

(56) References Cited

OTHER PUBLICATIONS

Pei-Feng Liu et al., Ablation of ATG4B Suppressed Autophagy and Activated AMPK for Cell Cycle Arrest in Cancer Cells, Cellular Physiology and Biochemistry, Nov. 23, 2017, pp. 728-740, vol. 44.
Annan Yang et al., Autophagy sustains pancreatic cancer growth through both cell autonomous and non-autonomous mechanisms, Jan. 9, 2018.
Noboru Mizushima et al., Protein Turnover via Autophagy: Implications for Metabolism, Annual Review of Nutrition, 2007, vol. 27, pp. 19-40.
Lorenzo Galluzzi et al. Autophagy in malignant transformation and cancer progression, The EMBO Journal, Feb. 23, 2015, vol. 34, No. 7, pp. 856-880.
Peidu Jiang et al., Autophagy and human diseases, Cell Research, Jan. 2014, vol. 24, No. 1, pp. 69-79.
Maurizio Renna et al., Chemical Inducers of Autophagy That Enhance the Clearance of Mutant Proteins in Neurodegenerative Diseases, The Journal of Biological Chemistry, Apr. 9, 2010, vol. 285, No. 15, pp. 11061-11067.
MJ Abedin et al., Autophagy delays apoptotic death in breast cancer cells following DNA damage, Cell Death and Differentiation, 2007, vol. 14, pp. 500-510.
Jean M. Mulcahy Levy et al., Autophagy Inhibition Improves Chemosensitivity in BRAF(V600E) Brain Tumors, Cancer Discovery, Jul. 2014, vol. 4, pp. 773-780.
Chong-Shan Shi et al., Activation of autophagy by inflammatory signals limits IL-1b production by targeting ubiquitinated inflammasomes for destruction, Nature Immunology, Mar. 2012, vol. 13, No. 3, pp. 255-263.
Zhineng J. Yang et al., Autophagy modulation for cancer therapy, Cancer Biology & Therapy, Jan. 15, 2011, vol. 11, No. 2, pp. 169-176.
Abigail R Solitro et al., Leaving the lysosome behind: novel developments in autophagy inhibition, Future Med. Chem., 2016, vol. 8, No. 1, pp. 73-86.
Paola Maycotte et al., Chloroquine sensitizes breast cancer cells to chemotherapy independent of autophagy, Autophagy, Feb. 2012, vol. 8, No. 2, pp. 200-212.
Hannelore Maes et al., Tumor Vessel Normalization by Chloroquine Independent of Autophagy, Cancer Cell, Aug. 11, 2014, vol. 26, pp. 190-206.
Daniel J Klionsky, Citing recent declines in the discovery of new ATG genes, some scientists now suggest that the end of autophagy research may be within sight, Autophagy, May 2014, vol. 10, No. 5, pp. 715-716.
Hitoshi Nakatogawa et al., Atg4 recycles inappropriately lipidated Atg8 to promote autophagosome biogenesis, Autophagy, Feb. 2012, vol. 8, No. 2, pp. 177-186.
Thong-Qiu Yu et al., Dual roles of Atg8-PE deconjugation by Atg4 in autophagy, Autophagy, Jun. 2012, vol. 8, No. 6, pp. 883-892.
Guillermo Marino et al., Human Autophagins, a Family of Cysteine Proteinases Potentially Implicated in Cell Degradation by Autophagy, The Journal of Biological Chemistry, Feb. 7, 2003, vol. 278, No. 6, pp. 3671-3678.
Marco B. E. Schaaf et al., LC3/GABARAP family proteins: autophagy-(un)related functions, The FASEB Journal, Dec. 2016, vol. 30, No. 12, pp. 3961-3978.
Min Li et al., Kinetics Comparisons of Mammalian Atg4 Homologues Indicate Selective Preferences toward Diverse Atg8 Substrates, The Journal of Biological Chemistry, Mar. 4,2011, vol. 286, No. 9, pp. 7327-7338.
Chih-Wen Shu et al., Synthetic substrates for measuring activity of autophagy proteases-autophagins (Atg4), Autophagy, Oct. 1,2010, vol. 6, No. 7, pp. 936-947.
Virginie M.S. Betin et al., Atg4D at the interface between autophagy and apoptosis, Autophagy, Oct. 1,2009, vol. 5, No. 7, pp. 1057-1059.
Oleg Trott et al., AutoDock Vina: Improving the Speed and Accuracy of Docking with a New Scoring Function, Efficient Optimization, and Multithreading, Journal of Computational Chemistry, 2009, vol. 31, No. 2, pp. 455-461.
Chia-En A. Chang et al., Ligand configurational entropy and protein binding, PNAS, Jan. 30, 2007, vol. 104, No. 5, pp. 1534-1539.
Vickie Tsui et al., Theory and Applications of the Generalized Born Solvation Model in Macromolecular Simulations, Biopolymers, 2001, vol. 56, pp. 275-291.
Hideki Hayashi et al., Versatile Assays for High Throughput Screening for Activators or Inhibitors of Intracellular Proteases and Their Cellular Regulators, PLoS ONE, Oct. 2009, vol. 4, No. 10, e7655.
Debra Akin et al., A novel ATG4B antagonist inhibits autophagy and has a negative impact on osteosarcoma tumors, Autophagy, Nov. 2014, vol. 10, No. 11, pp. 2021-2035.
Garrett M. Morris et al., AutoDock4 and AutoDockTools4: Automated Docking with Selective Receptor Flexibility, Journal of Computational Chemistry, 2009, vol. 30, No. 16, pp. 2785-2791.
Svetlana Bortnik et al., Identification of breast cancer cell subtypes sensitive to ATG4B inhibition, Oncotarget, 2016, vol. 7, No. 41, pp. 66970-66988.
Niaonobu Fujita et al., An Atg4B Mutant Hampers the Lipidation of LC3 Paralogues and Causes Defects in Autophagosome Closure, Molecular Biology of the Cell, Nov. 2008, vol. 19, pp. 4651-4659.
Virginie M.S. Betin et al., Autophagy facilitates organelle clearance during differentiation of human erythroblasts: Evidence for a role for ATG4 paralogs during autophagosome maturation, Autophagy, Jun. 2013, vol. 9, No. 6, pp. 881-893.
Daniel J Klionsky et al., Guidelines for the use and interpretation of assays for monitoring autophagy, Autophagy, 2016, vol. 12, No. 1, pp. 1-222.
Daniel F. Egan et al., Small Molecule Inhibition of the Autophagy Kinase ULK1 and Identification of ULK1 Substrates, Molecular Cell, Jul. 16, 2015, vol. 59, pp. 285-297.
Samuel E Weinberg et al., Targeting mitochondria metabolism for cancer therapy, Nature Chemical Biology, Jan. 2015, vol. 11, pp. 9-15.
Yuya Nishida et al., Discovery of Atg5/Atg7-independent alternative macroautophagy, Nature, Oct. 1,2009, vol. 161, pp. 654-658.
Pei-Feng Liu et al., ATG4B promotes colorectal cancer growth independent of autophagic flux, Autophagy, Aug. 2014, vol. 10, No. 8, pp. 1454-1465.
Katharina Rothe et al., The core autophagy protein ATG4B is a potential biomarker and therapeutic target in CML stem/progenitor cells, Blood, Jun. 5, 2014, vol. 123, No. 23, pp. 3622-3634.
Kenji Satoo et al., The structure of Atg4B—LC3 complex reveals the mechanism of LC3 processing and delipidation during autophagy, The EMBO Journal, 2009, vol. 28, No. 9, pp. 1341-1350.

\* cited by examiner

…

Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Ebselen; Ecomustine; Edelfosine; Edrecolomab; Eflomithine; Elemene; Emitefur; Epirubicin; Epristeride; Estramustine Analogue; Estrogen Agonists; Estrogen Antagonists; Exemestane; Fadrozole Hydrochloride; Fazarabine; Fenretinide; Floxuridine; Fludarabine Phosphate; Fluorouracil; Fluorocitabine; Fosquidone; Fostriecin Sodium; Fadrozole; Filgrastim; Finasteride; Flavopiridol; Flezelastine; Fluasterone; Fludarabine; Fluorodaunorunicin Hydrochloride; Forfenimex; Formestane; Fostriecin; Fotemustine; Gemcitabine; Gemcitabine Hydrochloride; Gadolinium Texaphyrin; Gallium Nitrate; Galocitabine; Ganirelix; Gelatinase Inhibitors; Glutathione Inhibitors; Hydroxyurea; Hepsulfam; Heregulin; Hexamethylene Bisacetamide; Hypericin; Idarubicin Hydrochloride; Ifosfamide; Ilmofosine; Interferon Alfa-2a; Interferon Alfa-2b; Interferon Alfa-nl; Interferon Alfan3; Interferon Beta-I a; Interferon Gamma-I b; Iproplatin; Irinotecan Hydrochloride; Ibandronic Acid; Idarubicin; Idoxifene; Idramantone; Ilomastat; Imidazoacridones; Imiquimod; Immunostimulant Peptides; Insulin-Like Growth Factor-I Receptor Inhibitor; Interferon Agonists; Interferons; Interleukins; Ioben-Guane; Iododoxorubicin; Ipomeanol, 4-; Irinotecan; Iroplact; Irsogladine; Isobengazole; Isohomohalicondrin B; Itasetron; Jasplakinolide; Kahalalide F; Lanreotide Acetate; Letrozole; Leuprolide Acetate; Liarozole Hydrochloride; Lometrexol Sodium; Lomustine; Losoxantrone Hydrochloride; Lamellarin-N Triacetate; Lanreotide; Leinamycin; Lenograstim; Lentinan Sulfate; Leptolstatin; Leukemia Inhibiting Factor; Leukocyte Alpha Interferon; Leuprolide+Estrogen+ Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lovastatin; Loxoribine; Lurtotecan; Lutetium Texaphyrin; Lysofylline; Lytic Peptides; Masoprocol; Maytansine; Mechlorethamine Hydrochloride; Megestrol Acetate; Melengestrol Acetate; Meiphalan; Menogaril; Mercaptopurine; Methotrexate; Methotrexate Sodium; Metoprine; Meturedepa; Mitindomide; Mitocarcin; Mitocromin; Mitomalcin; Mitomycin; Mitosper; Mitotane; Mitoxantrone Hydrochloride; Mycophenolic Acid; Maitansine; Mannostatina; Marimastat; Masoprocol; Maspin; Matrilysin Inhibitors; Matrix Metalloproteinase Inhibitors; Menogaril; Merbarone; Meterelin; Methioninase; Metoclopramide; Mif Inhibitor; Mifepristone; Miltefosine; Mirimostim; Mismatched Double Stranded Rna; Mitoguazone; Mitolactol; Mitomycin Analogues; Mitonafide; Mitotoxin Fibroblast Growth Factor-Saporin; Mitoxantrone; Mofarotene; Molgramostim; Monoclonal Antibody, Human Chorionic Gonadotrophin; Monophosphoryllipida+Myobacterium Cell Wall Sk; Mopidamol; Multiple Drug Resistance Gene Inhibitor; Multiple Tumor Suppressor I-Based Therapy; Mustard Anti Cancer Compound; Mycaperoxide B; Mycobacterial Cell Wall Extract; Myriaporone; Macrolides; Nocodazole; Nogalamycin; N-Acetyldinaline; N-Substituted Benzamides; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; Ormaplatin; Oxisuran; $O^6$-Benzylguanine; Octreotide; Okicenone; Oligonucleotides; Onapristone; Ondansetron; Oracin; Oral Cytokine Inducer; Osaterone; Oxaliplatin; Oxaunomycin; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Pommer Sodium; Porfiromycin; Prednimustine; Procarbazine Hydrochloride; Puromycin; Puromycin Hydrochloride; Pyrazofurin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentosan Polysulfate Sodium; Pentostatin; Pentrozole; Perflubron; Perfosfamide; Perillyl Alcohol; Phenazinomycin; Phenylacetate; Phosphatase Inhibitors; Picibanil; Pilocarpine Hydrochloride; Pirarubicin; Piritrexim; Placetina; Placetin B; Plasminogen Activator Inhibitor; Platinum Complex; Platinum Compounds; Platinum-Triamine Complex; Porfimer Sodium; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin-Polyoxyethylene Conjugate; Proteasome Inhibitors; Riboprine; Rogletimide; Raf Antagonists; Raltitrexed; Ramosetron; Ras Famesyl Protein Transferase Inhibitors; Ras Inhibitors; Ras-Gap Inhibitor; Retelliptine Demethylated; Rhenium Re 186 Etidronate; Rhizoxin; Ribozymes; Rii Retinamide; Rohitukine; Romurtide; Roquinimex; Rubiginone Bi; Ruboxyl; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Saintopin; Sarcnu; Sarcophytola; Sargramostim; Sdi I Mimetics; Senescence Derived Inhibitor I; Sense Oligonucleotides; Signal Transduction Inhibitors; Signal Transduction Modulators; Single Chain Antigen Binding Protein; Sizofuran; Sobuzoxane; Sodium Borocaptate; Sodium Phenylacetate; Solverol; Somatomedin Binding Protein; Sonermin; Sparfosic Acid; Spicamycin D; Splenopentin; Spongistatin I; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Tallimustine; Tamoxifen Methiodide; Tauromustine; Tazarotene; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Tretinoin; Triacetyluridine; Triciribine; Tropisetron; Turosteride; Tyrosine Kinase Inhibitors; Tyrphostins; Topoisomerase Inhibitors; Uracil Mustard; Uredepa; Ubc Inhibitors; Ubenimex; Urogenital Sinus-Derived Growth Inhibitory Factor; Urokinase Receptor Antagonists; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Variolin B; Vector System, Erythrocyte Gene Therapy; Velaresol; Veramine; Verdins; Vinorelbine; Vinxaltine; Vitaxin; Vinca Alkaloids; Zeniplatin; Zinostatin; Zorubicin Hydrochloride; Zanoterone; Zilascorb; and Zinostatin Stimalamer.

According to the above, the chemotherapeutic agent is Doxorubicin or Canmptothecin.

According to the above, the infectious disease is caused by one from a group consisting of HIV I and II, HBV, HCV, *Anaplasma phagocytophilum, C. burnetii, and Porphyromonas gingivalis* or secondary disease states or conditions associated with infectious diseases.

According to the above, the ischemia-induced disease is ischemia-induced neuronal death, stroke, traumatic Brain Injury, neonatal ischemic brain injury, ischemia reperfusion damage in heart or kidney.

In one aspect, the invention provides a method of increasing a subject's responsiveness to a therapy for a cancer comprising inhibition of ATG4B activity in cells. The method comprises administering the subject with an effective amount of tioconazole.

According to the above, the cancer is colorectal cancer, neural glioma cancer, breast cancer, gastric cancer, or pancreatic cancer.

According to the above, the cancer is selected from a group consisting of breast cancer, bladder cancer, bone cancer, colorectal cancer, cancer of the brain or nervous system, cancer of endocrine system, cancer of the lymphatic system, epidermoid carcinoma, fibrosarcoma, gastrointestinal cancer, head and neck cancer, Kaposi's sarcoma, kidney cancer, lung cancer, liver cancer, neural glioma cancer, mesothelioma, neurectodermal tumor, non-small cell lung cancer, ovarian cancer, gastric cancer, pancreatic cancer, prostate cancer, skin cancer, and testicular cancer.

According to the above, the tioconazole is in combination with a chemotherapeutic agent in chemotherapy.

According to the above, the chemotherapeutic agent is selected from a group consisting of 20-epi-1,25 dihydroxyvitamin D3; 5-ethynyluracil; Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Abiraterone; Acylfulvene; Adecypenol; Adozelesin; All-Tk Antagonists; Ambamustine; Amidox; Amifostine; Aminolevulinic Acid; Amrubicin; Amsacrine; Anagrelide; Anastrozole; Andrographolide; Angiogenesis Inhibitors; Antagonist D; Antagonist G; Antarelix; Anti-Dorsalizing Morphogenetic Protein-I; Antiandrogen, Prostatic Carcinoma; Antiestrogen; Antineoplaston; Antisense Oligonucleotides; Aphidicolin Glycinate; Apoptosis Gene Modulators; Apoptosis Regulators; Apurinic Acid; Ara-Cdp-Dl-Ptba; Arginine Deaminase; Asulacrine; Atamestane; Atrimustine; Axinastatin I; Axinastatin 2; Axinastatin 3; Azasetron; Azatoxin; Aza Osine; Antimetabolites; Platinum-Based Agents; Alkylating Agents; Tyrosine Kinase Inhibitors; Anthracycline Antibiotics; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Baccatin Iii Derivatives; Balanol; Batimastat; Bcr/Abl Antagonists; Benzochlorins; Benzoylstaurosporine; Beta-Lactam Derivatives; Beta-Alethine; Betaclamycin B; Betulinic Acid; Bfgf Inhibitor; Bisantrene; Bisaziridinylspermine; Bistratene A; Breflate; Budotitane; Buthionine Sulfoximine; Cactinomyde; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Calcipotriol; Calphostin C; Camptothecin derivatives; Canarypox I1-2; Capecitabine; Carboxamide-Amino-Triazole; Carboxyamidotriazole; Carest M3; Carn 700; Cartilage Derived Inhibitor; Casein Kinase Inhibitors (1 cos); Castanospermine; Cecropin B; Cetrorelix; Chlorins; Chloroquinoxaline Sulfonamide; Cicaprost; Cis-Porphyrin; Clomifene Analogues; Clotrimazole; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacarbazine; Dactinomycin; Daunorubicin Hydrochloride; Decitabine; Dexormaplatin; Dezaguanine; Dezaguanine Mesylate; Diaziquone; Docetaxel; Docetaxel Anhydrous; Doxorubicin; Doxorubicin Hydrochloride; Droloxifene; Droloxifene Citrate; Dromostanolone Propionate; Duazomycin; Dacliximab; Dehydrodidenmin B; Deslorelin; Dexifosfamide; Dexrazoxane; Dexverapamil; Diaziquone; Didenmin B; Didox; Diethylnorspermine; Dihydro-5-Azacytidine; Dihydrotaxol, 9-; Dioxamycin; Diphenyl Spiromustine; Docosanol; Dolasetron; Doxifluridine; Dronabinol; Duocarmycin Sa; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Ebselen; Ecomustine; Edelfosine; Edrecolomab; Eflomithine; Elemene; Emitefur; Epirubicin; Epristeride; Estramustine Analogue; Estrogen Agonists; Estrogen Antagonists; Exemestane; Fadrozole Hydrochloride; Fazarabine; Fenretinide; Floxuridine; Fludarabine Phosphate; Fluorouracil; Fluorocitabine; Fosquidone; Fostriecin Sodium; Fadrozole; Filgrastim; Finasteride; Flavopiridol; Flezelastine; Fluasterone; Fludarabine; Fluorodaunorunicin Hydrochloride; Forfenimex; Formestane; Fostriecin; Fotemustine; Gemcitabine; Gemcitabine Hydrochloride; Gadolinium Texaphyrin; Gallium Nitrate; Galocitabine; Ganirelix; Gelatinase Inhibitors; Glutathione Inhibitors; Hydroxyurea; Hepsulfam; Heregulin; Hexamethylene Bisacetamide; Hypericin; Idarubicin Hydrochloride; Ifosfamide; Ilmofosine; Interferon Alfa-2a; Interferon Alfa-2b; Interferon Alfa-nl; Interferon Alfan3; Interferon Beta-I a; Interferon Gamma-I b; Iproplatin; Irinotecan Hydrochloride; Ibandronic Acid; Idarubicin; Idoxifene; Idramantone; Ilomastat; Imidazoacridones; Imiquimod; Immunostimulant Peptides; Insulin-Like Growth Factor-I Receptor Inhibitor; Interferon Agonists; Interferons; Interleukins; Ioben-Guane; Iododoxorubicin; Ipomeanol, 4-; Irinotecan; Iroplact; Irsogladine; Isobengazole; Isohomohalicondrin B; Itasetron; Jasplakinolide; Kahalalide F; Lanreotide Acetate; Letrozole; Leuprolide Acetate; Liarozole Hydrochloride; Lometrexol Sodium; Lomustine; Losoxantrone Hydrochloride; Lamellarin-N Triacetate; Lanreotide; Leinamycin; Lenograstim; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lovastatin; Loxoribine; Lurtotecan; Lutetium Texaphyrin; Lysofylline; Lytic Peptides; Masoprocol; Maytansine; Mechlorethamine Hydrochloride; Megestrol Acetate; Melengestrol Acetate; Meiphalan; Menogaril; Mercaptopurine; Methotrexate; Methotrexate Sodium; Metoprine; Meturedepa; Mitindomide; Mitocarcin; Mitocromin; Mitomalcin; Mitomycin; Mitosper; Mitotane; Mitoxantrone Hydrochloride; Mycophenolic Acid; Maitansine; Mannostatina; Marimastat; Masoprocol; Maspin; Matrilysin Inhibitors; Matrix Metalloproteinase Inhibitors; Menogaril; Merbarone; Meterelin; Methioninase; Metoclopramide; Mif Inhibitor; Mifepristone; Miltefosine; Mirimostim; Mismatched Double Stranded Rna; Mitoguazone; Mitolactol; Mitomycin Analogues; Mitonafide; Mitotoxin Fibroblast Growth Factor-Saporin; Mitoxantrone; Mofarotene; Molgramostim; Monoclonal Antibody, Human Chorionic Gonadotrophin; Monophosphoryllipida+Myobacterium Cell Wall Sk; Mopidamol; Multiple Drug Resistance Gene Inhibitor; Multiple Tumor Suppressor I-Based Therapy; Mustard Anti Cancer Compound; Mycaperoxide B; Mycobacterial Cell Wall Extract; Myriaporone; Macrolides; Nocodazole; Nogalamycin; N-Acetyldinaline; N-Substituted Benzamides; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; Ormaplatin; Oxisuran; 06-Benzylguanine; Octreotide; Okicenone; Oligonucleotides; Onapristone; Ondansetron; Oracin; Oral Cytokine Inducer; Osaterone; Oxaliplatin; Oxaunomycin; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Pommer Sodium; Porfiromycin; Prednimustine; Procarbazine Hydrochloride; Puromycin; Puromycin Hydrochloride; Pyrazofurin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentosan Polysulfate Sodium; Pentostatin; Pentrozole; Perflubron; Perfosfamide; Perillyl Alcohol; Phenazinomycin; Phenylacetate; Phosphatase Inhibitors; Picibanil; Pilocarpine Hydrochloride; Pirarubicin; Piritrexim; Placetina; Placetin B; Plasminogen Activator Inhibitor; Platinum Complex; Platinum Compounds; Platinum-Triamine Complex; Porfimer Sodium; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin-Polyoxyethylene Conjugate; Proteasome Inhibitors; Riboprine; Rogletimide; Raf Antagonists; Raltitrexed; Ramosetron; Ras Famesyl Protein Transferase Inhibitors; Ras Inhibitors; Ras-Gap Inhibitor; Retelliptine Demethylated; Rhenium Re 186 Etidronate; Rhizoxin; Ribozymes; Rii Retinamide; Rohitukine; Romurtide; Roquinimex; Rubiginone Bi; Ruboxyl; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Saintopin; Sarcnu; Sarcophytola; Sargramostim; Sdi I Mimetics; Senescence Derived Inhibitor I; Sense Oligonucleotides; Signal Transduction Inhibitors; Signal Transduction Modulators; Single Chain Antigen Binding Protein; Sizofuran; Sobuzoxane; Sodium Borocaptate; Sodium Phenylacetate; Solverol; Somatomedin Binding Protein; Sonermin; Sparfosic Acid; Spicamycin D; Splenopentin; Spongistatin I; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Tallimustine; Tamoxifen Methiodide; Tauromustine; Tazarotene; Tellurapyrrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Tretinoin; Triacetyluridine; Triciribine; Tropisetron; Turosteride; Tyrosine Kinase Inhibitors; Tyrphostins; Topoisomerase Inhibitors; Uracil Mustard; Uredepa; Ubc Inhibitors; Ubenimex; Urogenital Sinus-Derived Growth Inhibitory Factor; Urokinase Receptor Antagonists; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Variolin B; Vector System, Erythrocyte Gene Therapy; Velaresol; Veramine; Verdins; Vinorelbine; Vinxaltine; Vitaxin; Vinca Alkaloids; Zeniplatin; Zinostatin; Zorubicin Hydrochloride; Zanoterone; Zilascorb; and Zinostatin Stimalamer.

According to the above, the chemotherapeutic agent is Doxorubicin or Camptothecin.

In one aspect, the invention provides a method for enhancing or inducing a response in a cancer cell consisting of cytotoxicity, chemosensitivity or starvation-sensitivity; said method comprises administering a subject with an effective amount of tioconazole to inhibit ATG4B activity.

According to the above, the cancer cell is from colorectal cancer, neural glioma cancer, breast cancer, or gastric cancer, pancreatic cancer.

According to the above, the cancer cell is selected from a group consisting of breast cancer, bladder cancer, bone cancer, colorectal cancer, cancer of the brain or nervous system, cancer of endocrine system, cancer of the lymphatic system, epidermoid carcinoma, fibrosarcoma, gastrointestinal cancer, head and neck cancer, Kaposi's sarcoma, kidney cancer, lung cancer, liver cancer, neural glioma cancer, mesothelioma, neurectodermal tumor, non-small cell lung cancer, ovarian cancer, gastric cancer, pancreatic cancer, prostate cancer, skin cancer, and testicular cancer.

According to the above, the tioconazole is in combination with a chemotherapeutic agent in chemotherapy.

According to the above, the chemotherapeutic agent is selected from a group consisting of 20-epi-1,25 dihydroxyvitamin D3; 5-ethynyluracil; Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Abiraterone; Acylfulvene; Adecypenol; Adozelesin; All-Tk Antagonists; Ambamustine; Amidox; Amifostine; Aminolevulinic Acid; Amrubicin; Amsacrine; Anagrelide; Anastrozole; Andrographolide; Angiogenesis Inhibitors; Antagonist D; Antagonist G; Antarelix; Anti-Dorsalizing Morphogenetic Protein-I; Antiandrogen, Prostatic Carcinoma; Antiestrogen; Antineoplaston; Antisense Oligonucleotides; Aphidicolin Glycinate; Apoptosis Gene Modulators; Apoptosis Regulators; Apurinic Acid; Ara-Cdp-Dl-Ptba; Arginine Deaminase; Asulacrine; Atamestane; Atrimustine; Axinastatin I; Axinastatin 2; Axinastatin 3; Azasetron; Azatoxin; Aza Osine; Antimetabolites; Platinum-Based Agents; Alkylating Agents; Tyrosine Kinase Inhibitors; Anthracycline Antibiotics; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Baccatin Iii Derivatives; Balanol; Batimastat; Bcr/Abl Antagonists; Benzochlorins; Benzoylstaurosporine; Beta-Lactam Derivatives; Beta-Alethine; Betaclamycin B; Betulinic Acid; Bfgf Inhibitor; Bisantrene; Bisaziridinylspermine; Bistratene A; Breflate; Budotitane; Buthionine Sulfoximine; Cactinomyde; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Calcipotriol; Calphostin C; Camptothecin derivatives; Canarypox I1-2; Capecitabine; Carboxamide-Amino-Triazole; Carboxyamidotriazole; Carest M3; Carn 700; Cartilage Derived Inhibitor; Casein Kinase Inhibitors (1 cos); Castanospermine; Cecropin B; Cetrorelix; Chlorins; Chloroquinoxaline Sulfonamide; Cicaprost; Cis-Porphyrin; Clomifene Analogues; Clotrimazole; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacarbazine; Dactinomycin; Daunorubicin Hydrochloride; Decitabine; Dexormaplatin; Dezaguanine; Dezaguanine Mesylate; Diaziquone; Docetaxel; Docetaxel Anhydrous; Doxorubicin; Doxorubicin Hydrochloride; Droloxifene; Droloxifene Citrate; Dromostanolone Propionate; Duazomycin; Dacliximab; Dehydrodidenmin B; Deslorelin; Dexifosfamide; Dexrazoxane; Dexverapamil; Diaziquone; Didenmin B; Didox; Diethylnorspermine; Dihydro-5-Azacytidine; Dihydrotaxol, 9-; Dioxamycin; Diphenyl Spiromustine; Docosanol; Dolasetron; Doxifluridine; Dronabinol; Duocarmycin Sa; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Ebselen; Ecomustine; Edelfosine; Edrecolomab; Eflomithine; Elemene; Emitefur; Epirubicin; Epristeride; Estramustine Analogue; Estrogen Agonists; Estrogen Antagonists; Exemestane; Fadrozole Hydrochloride; Fazarabine; Fenretinide; Floxuridine; Fludarabine Phosphate; Fluorouracil; Fluorocitabine; Fosquidone; Fostriecin Sodium; Fadrozole; Filgrastim; Finasteride; Flavopiridol; Flezelastine; Fluasterone; Fludarabine; Fluorodaunorunicin Hydrochloride; Forfenimex; Formestane; Fostriecin; Fotemustine; Gemcitabine; Gemcitabine Hydrochloride; Gadolinium Texaphyrin; Gallium Nitrate; Galocitabine; Ganirelix; Gelatinase Inhibitors; Glutathione Inhibitors; Hydroxyurea; Hepsulfam; Heregulin; Hexamethylene Bisacetamide; Hypericin; Idarubicin Hydrochloride; Ifosfamide; Ilmofosine; Interferon Alfa-2a; Interferon Alfa-2b; Interferon Alfa-nl; Interferon Alfan3; Interferon Beta-I a; Interferon Gamma-I b; Iproplatin; Irinotecan Hydrochloride; Ibandronic Acid; Idarubicin; Idoxifene; Idramantone; Ilomastat; Imidazoacridones; Imiquimod; Immunostimulant Peptides; Insulin-Like Growth Factor-I Receptor Inhibitor; Interferon Agonists; Interferons; Interleukins; Ioben-Guane; Iododoxorubicin; Ipomeanol, 4-; Irinotecan; Iroplact; Irsogladine; Isobengazole; Isohomohalicondrin B; Itasetron; Jasplakinolide; Kahalalide F; Lanreotide Acetate; Letrozole; Leuprolide Acetate; Liarozole Hydrochloride; Lometrexol Sodium; Lomustine; Losoxantrone Hydrochloride; Lamellarin-N Triacetate; Lanreotide; Leinamycin; Lenograstim; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lovastatin; Loxoribine; Lurtotecan; Lutetium Texaphyrin; Lysofylline; Lytic Peptides; Masoprocol; Maytansine; Mechlorethamine Hydrochloride; Megestrol Acetate; Melengestrol Acetate; Meiphalan; Menogaril; Mercaptopurine; Methotrexate; Methotrexate Sodium; Metoprine; Meturedepa; Mitindomide; Mitocarcin; Mitocromin; Mitomalcin; Mitomycin; Mitosper; Mitotane; Mitoxantrone Hydrochloride; Mycophenolic Acid; Maitansine; Mannostatina; Marimastat; Masoprocol; Maspin; Matrilysin Inhibitors; Matrix Metalloproteinase Inhibitors; Menogaril; Merbarone; Meterelin; Methioninase; Metoclopramide; Mif Inhibitor; Mifepristone; Miltefosine; Mirimostim; Mismatched Double Stranded Rna; Mitoguazone; Mitolactol; Mitomycin Analogues; Mitonafide; Mitotoxin Fibroblast Growth Factor-Saporin; Mitoxantrone; Mofarotene; Molgramostim; Monoclonal Antibody, Human Chorionic Gonadotrophin; Monophosphoryllipida+Myobacterium Cell Wall Sk; Mopidamol; Multiple Drug Resistance Gene Inhibitor; Multiple Tumor Suppressor I-Based Therapy; Mustard Anti Cancer Compound; Mycaperoxide B; Mycobacterial Cell Wall Extract; Myriaporone; Macrolides; Nocodazole; Nogalamycin; N-Acetyldinaline; N-Substituted Benzamides; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; Ormaplatin; Oxisuran; $O^6$-Benzylguanine; Octreotide; Okicenone; Oligonucleotides; Onapristone; Ondansetron; Oracin; Oral Cytokine Inducer; Osaterone; Oxaliplatin; Oxaunomycin; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Pommer Sodium; Porfiromycin; Prednimustine; Procarbazine Hydrochloride; Puromycin; Puromycin Hydrochloride; Pyrazofurin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentosan Polysulfate Sodium; Pentostatin; Pentrozole; Perflubron; Perfosfamide; Perillyl Alcohol; Phenazinomycin; Phenylacetate; Phosphatase Inhibitors; Picibanil; Pilocarpine Hydrochloride; Pirarubicin; Piritrexim; Placetina; Placetin B; Plasminogen Activator Inhibitor; Platinum Complex; Platinum Compounds; Platinum-Triamine Complex; Porfimer Sodium; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin-Polyoxyethylene Conjugate; Proteasome Inhibitors; Riboprine; Rogletimide; Raf Antagonists; Raltitrexed; Ramosetron; Ras Famesyl Protein Transferase Inhibitors; Ras Inhibitors; Ras-Gap Inhibitor; Retelliptine Demethylated; Rhenium Re 186 Etidronate; Rhizoxin; Ribozymes; Rii Retinamide; Rohitukine; Romurtide; Roquinimex; Rubiginone Bi; Ruboxyl; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Saintopin; Sarcnu; Sarcophytola; Sargramostim; Sdi I Mimetics; Senescence Derived Inhibitor I; Sense Oligonucleotides; Signal Transduction Inhibitors; Signal Transduction Modulators; Single Chain Antigen Binding Protein; Sizofuran; Sobuzoxane; Sodium Borocaptate; Sodium Phenylacetate; Solverol; Somatomedin Binding Protein; Sonermin; Sparfosic Acid; Spicamycin D; Splenopentin; Spongistatin I; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista;

Suramin; Swainsonine; Synthetic Glycosaminoglycans; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Tallimustine; Tamoxifen Methiodide; Tauromustine; Tazarotene; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Tretinoin; Triacetyluridine; Triciribine; Tropisetron; Turosteride; Tyrosine Kinase Inhibitors; Tyrphostins; Topoisomerase Inhibitors; Uracil Mustard; Uredepa; Ubc Inhibitors; Ubenimex; Urogenital Sinus-Derived Growth Inhibitory Factor; Urokinase Receptor Antagonists; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Variolin B; Vector System, Erythrocyte Gene Therapy; Velaresol; Veramine; Verdins; Vinorelbine; Vinxaltine; Vitaxin; Vinca Alkaloids; Zeniplatin; Zinostatin; Zorubicin Hydrochloride; Zanoterone; Zilascorb; and Zinostatin Stimalamer.

The foregoing and other features and advantages of the present invention disclosure will be more readily appreciated by one of ordinary skilled in the art from the following figures, embodiments and descriptions.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Some embodiments of the invention are herein described with reference to the accompanying drawings. With specific reference to the drawings in detail, it is emphasized that the particulars shown are by way of example and for purposes of illustrative discussion of embodiments of the invention.

DETAIL DESCRIPTION OF THE INVENTION

Figure 1:
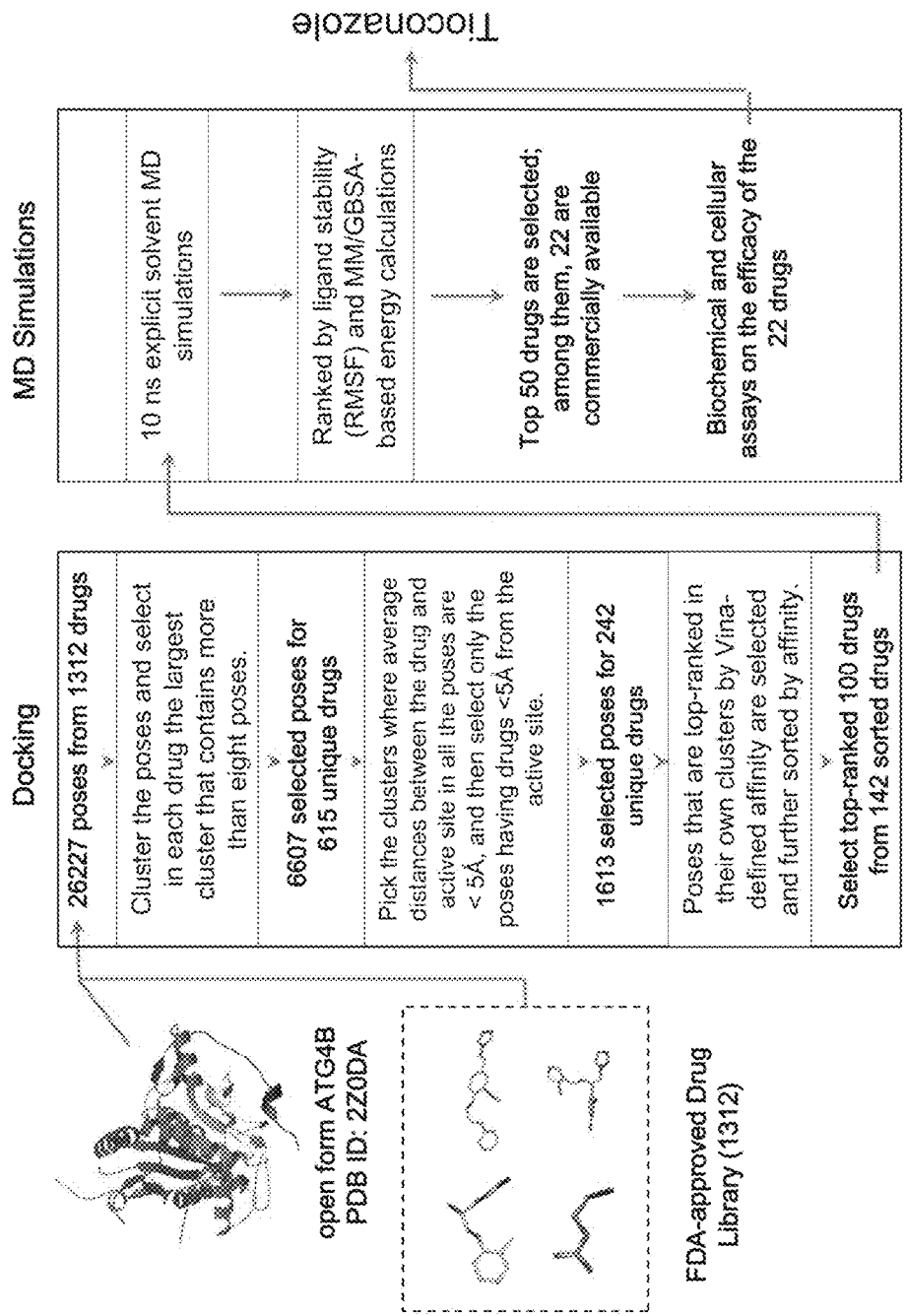
FIG. 1 shows the workflow of the in silico drug screening for 1312 FDA-approved drugs.
Figure 2:
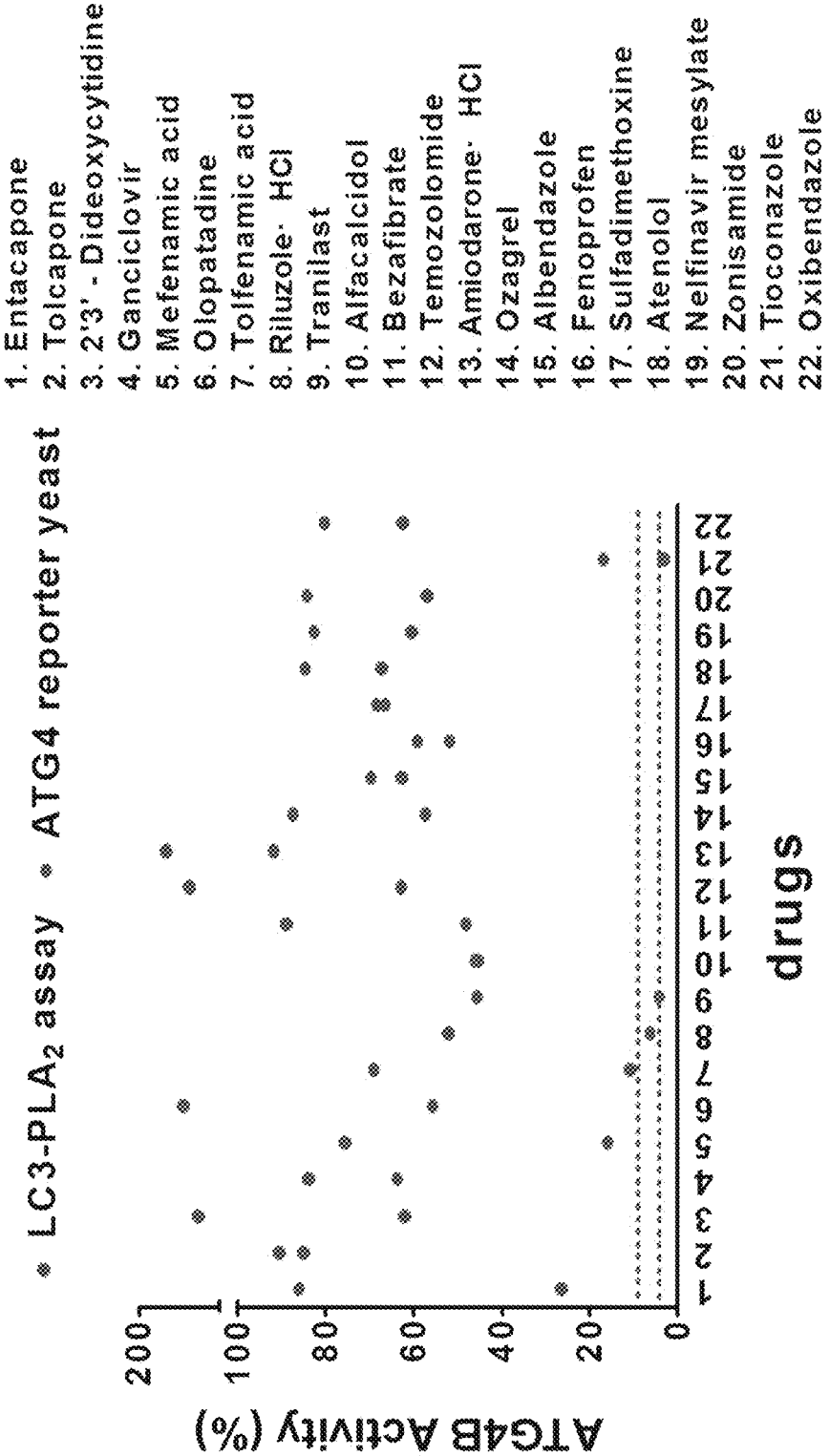
FIGS. 2-10 show the representative images of screening and evaluation of drugs for ATG4 inhibition.
Figure 3:
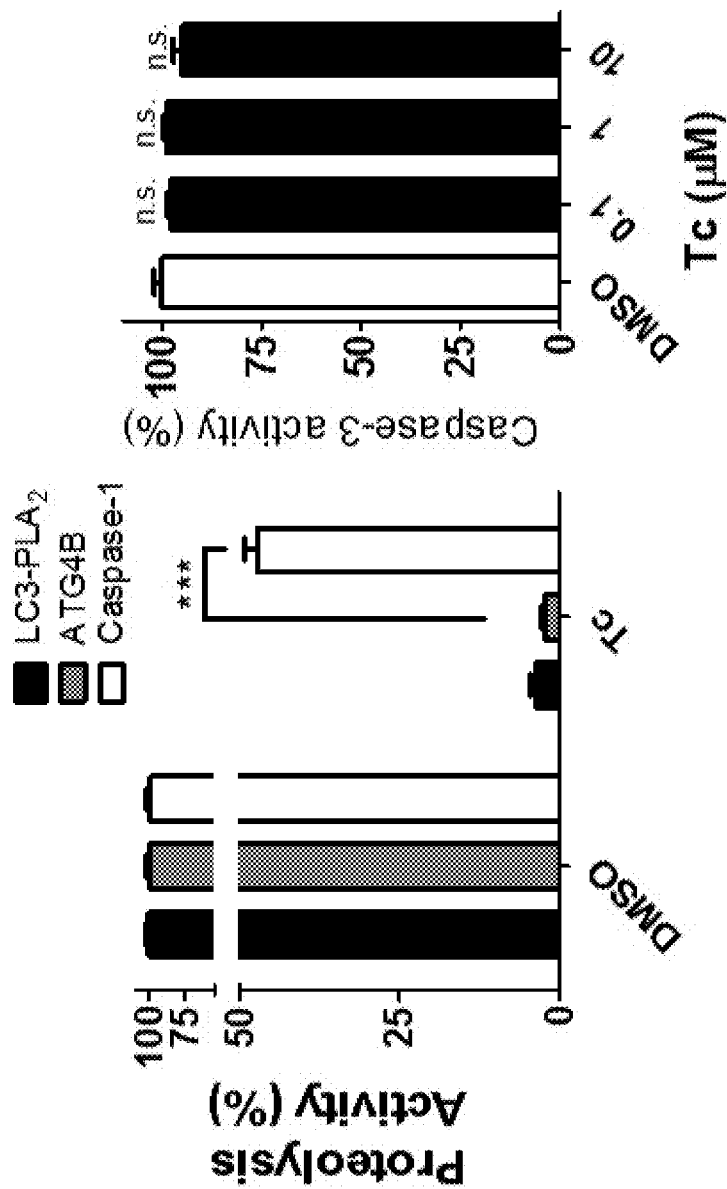

Disclosed in detail herein is a method of treating an ATG4B-related disorder via administering a subject with an effective amount of tioconazole. The invention will be able to be practiced by one skilled in the art that references to the following embodiments and descriptions.

Autophagy modulation has been suggested as a potential mean of cancer therapy. However, this theory remains controversial in clinical settings due to the limited number of drugs available to modulate autophagy. At least thirty-eight ATG genes that are involved in the autophagy machinery have been identified [12]. ATG4 is a key component of autophagy signaling, and its levels are elevated in cancer cells to promote tumorigenesis and malignancy [33, 34], which suggests that ATG4 is a suitable drug target to interrogate the role of autophagy in cancer treatment. Specifically, ATG4 is a cysteine protease required for the initiation of ATG8 conjugation to phosphatidylethanolamine (PE) and the deconjugation of PE-ATG8 (ATG8-II) from membranes of autophagosomes or non-autophagosomes to facilitate autophagy [13, 14]. The human genome contains four ATG4 genes (ATG4A, ATG4B, ATG4C and ATG4D) [15] and seven ATG8 genes (two isoforms of LC3A, LC3B/C, GABARAP, GABARAPL1 and GABARAPL2) [16]. Although ATG4B is the most proteolytically active ATG4 protein and exhibits the broadest specificity for substrates among the four ATG4 members, the remaining ATG4 members exhibit proteolytic activity on certain substrates of GABARAP subfamily [17, 18]. ATG4A cleaves all GABARAP subfamily members (GABARAP, GABARAPL1 and GABARAPL2), whereas ATG4D requires caspase-3 to activate and hydrolyze GABARAPL1 and GABARAPL2 [19]. Overall, currently available information suggests that ATG4 family members have both overlapping and unique functions.

A platform is employed to integrate computational docking and molecular dynamics (MD) simulations to screen FDA-approved drugs for ATG4 inhibitors. Subsequently, biochemical and cellular ATG4B reporter assays were used to confirm tioconazole as an ATG4 inhibitor. Tioconazole is predicted to occupy the active site of ATG4A/B, and it diminishes autophagic flux in cancer cells. Furthermore, tioconazole suppresses tumor growth and enhanced chemotherapy-induced apoptosis in cancer cells and tumor xenografts. The results show that tioconazole, a clinical antifungal drug, can inhibit ATG4 to diminish autophagic flux and ultimately sensitize cancer cells to chemotherapeutic drugs.

A method of this invention is directed to treating an ATG4B-related disorder comprising administering a subject with an effective amount of tioconazole.

Examples of the ATG4B-related disorder include, but are not limited to, cancer, infectious disease and ischemia-induced disease.

Examples of the cancer include, but are not limited to, breast cancer, bladder cancer, bone cancer, colorectal cancer, cancer of the brain or nervous system, cancer of endocrine system, cancer of the lymphatic system, epidermoid carcinoma, fibrosarcoma, gastrointestinal cancer, head and neck cancer, Kaposi's sarcoma, kidney cancer, lung cancer, liver cancer, neural glioma cancer, mesothelioma, neurectodermal tumor, non-small cell lung cancer, ovarian cancer, gastric cancer, pancreatic cancer, prostate cancer, skin cancer, and testicular cancer.

The method includes administering a subject with an effective amount of tioconazole in combination with a chemotherapeutic agent in chemotherapy.

Examples of the chemotherapeutic agent include, but are not limited to, 20-epi-1,25 dihydroxyvitamin D3; 5-ethynyluracil; Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Abiraterone; Acylfulvene; Adecypenol; Adozelesin; All-Tk Antagonists; Ambamustine; Amidox; Amifostine; Aminolevulinic Acid; Amrubicin; Amsacrine; Anagrelide; Anastrozole; Andrographolide; Angiogenesis Inhibitors; Antagonist D; Antagonist G; Antarelix; Anti-Dorsalizing Morphogenetic Protein-I; Antiandrogen, Prostatic Carcinoma; Antiestrogen; Antineoplaston; Antisense Oligonucleotides; Aphidicolin Glycinate; Apoptosis Gene Modulators; Apoptosis Regulators; Apurinic Acid; Ara-Cdp-Dl-Ptba; Arginine Deaminase; Asulacrine; Atamestane; Atrimustine; Axinastatin I; Axinastatin 2; Axinastatin 3; Azasetron; Azatoxin; Aza Osine; Antimetabolites; Platinum-Based Agents; Alkylating Agents; Tyrosine Kinase Inhibitors; Anthracycline Antibiotics; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Baccatin Iii Derivatives; Balanol; Batimastat; Bcr/Abl Antagonists; Benzochlorins; Benzoylstaurosporine; Beta-Lactam Derivatives; Beta-Alethine; Betaclamycin B; Betulinic Acid; Bfgf Inhibitor; Bisantrene; Bisaziridinylspermine; Bistratene A; Breflate; Budotitane; Buthionine Sulfoximine; Cactinomyde; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Calcipotriol; Calphostin C; Camptothecin derivatives; Canarypox I1-2; Capecitabine; Carboxamide-Amino-Triazole; Carboxyamidotriazole; Carest M3; Carn 700; Cartilage Derived Inhibitor; Casein Kinase Inhibitors (1 cos); Castanospermine; Cecropin B; Cetrorelix; Chlorins; Chloroquinoxaline Sulfonamide; Cicaprost; Cis-Porphyrin; Clomifene Analogues; Clotrimazole; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacarbazine; Dactinomycin; Daunorubicin Hydrochloride; Decitabine; Dexormaplatin; Dezaguanine; Dezaguanine Mesylate; Diaziquone; Docetaxel; Docetaxel Anhydrous; Doxorubicin; Doxorubicin Hydrochloride; Droloxifene; Droloxifene Citrate; Dromostanolone Propionate; Duazomycin; Dacliximab; Dehydrodidenmin B; Deslorelin; Dexifosfamide; Dexrazoxane; Dexverapamil; Diaziquone; Didenmin B; Didox; Diethylnorspermine; Dihydro-5-Azacytidine; Dihydrotaxol, 9-; Dioxamycin; Diphenyl Spiromustine; Docosanol; Dolasetron; Doxifluridine; Dronabinol; Duocarmycin Sa; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Ebselen; Ecomustine; Edelfosine; Edrecolomab; Eflomithine; Elemene; Emitefur; Epirubicin; Epristeride; Estramustine Analogue; Estrogen Agonists; Estrogen Antagonists; Exemestane; Fadrozole Hydrochloride; Fazarabine; Fenretinide; Floxuridine; Fludarabine Phosphate; Fluorouracil; Fluorocitabine; Fosquidone; Fostriecin Sodium; Fadrozole; Filgrastim; Finasteride; Flavopiridol; Flezelastine; Fluasterone; Fludarabine; Fluorodaunorunicin Hydrochloride; Forfenimex; Formestane; Fostriecin; Fotemustine; Gemcitabine; Gemcitabine Hydrochloride; Gadolinium Texaphyrin; Gallium Nitrate; Galocitabine; Ganirelix; Gelatinase Inhibitors; Glutathione Inhibitors; Hydroxyurea; Hepsulfam; Hereguglin; Hexamethylene Bisacetamide; Hypericin; Idarubicin Hydrochloride; Ifosfamide; Ilmofosine; Interferon Alfa-2a; Interferon Alfa-2b; Interferon Alfa-nl; Interferon Alfan3; Interferon Beta-I a; Interferon Gamma-I b; Iproplatin; Irinotecan Hydrochloride; Ibandronic Acid; Idarubicin; Idoxifene; Idramantone; Ilomastat; Imidazoacridones; Imiquimod; Immunostimulant Peptides; Insulin-Like Growth Factor-I Receptor Inhibitor; Interferon Agonists; Interferons; Interleukins; Ioben-Guane; Iododoxorubicin; Ipomeanol, 4-; Irinotecan; Iroplact; Irsogladine; Isobengazole; Isohomohalicondrin B; Itasetron; Jasplakinolide; Kahalalide F; Lanreotide Acetate; Letrozole; Leuprolide Acetate; Liarozole Hydrochloride; Lometrexol Sodium; Lomustine; Losoxantrone Hydrochloride; Lamellarin-N Triacetate; Lanreotide; Leinamycin; Lenograstim; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lovastatin; Loxoribine; Lurtotecan; Lutetium Texaphyrin; Lysofylline; Lytic Peptides; Masoprocol; Maytansine; Mechlorethamine Hydrochloride; Megestrol Acetate; Melengestrol Acetate; Meiphalan; Menogaril; Mercaptopurine; Methotrexate; Methotrexate Sodium; Metoprine; Meturedepa; Mitindomide; Mitocarcin; Mitocromin; Mitomalcin; Mitomycin; Mitosper; Mitotane; Mitoxantrone Hydrochloride; Mycophenolic Acid; Maitansine; Mannostatina; Marimastat; Masoprocol; Maspin; Matrilysin Inhibitors; Matrix Metalloproteinase Inhibitors; Menogaril; Merbarone; Meterelin; Methioninase; Metoclopramide; Mif Inhibitor; Mifepristone; Miltefosine; Mirimostim; Mismatched Double Stranded Rna; Mitoguazone; Mitolactol; Mitomycin Analogues; Mitonafide; Mitotoxin Fibroblast Growth Factor-Saporin; Mitoxantrone; Mofarotene; Molgramostim; Monoclonal Antibody, Human Chorionic Gonadotrophin; Monophosphoryllipida+Myobacterium Cell Wall Sk; Mopidamol; Multiple Drug Resistance Gene Inhibitor; Multiple Tumor Suppressor I-Based Therapy; Mustard Anti Cancer Compound; Mycaperoxide B; Mycobacterial Cell Wall Extract; Myriaporone; Macrolides; Nocodazole; Nogalamycin; N-Acetyldinaline; N-Substituted Benzamides; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; Ormaplatin; Oxisuran; $O^6$-Benzylguanine; Octreotide; Okicenone; Oligonucleotides; Onapristone; Ondansetron; Oracin; Oral Cytokine Inducer; Osaterone; Oxaliplatin; Oxaunomycin; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Pommer Sodium; Porfiromycin; Prednimustine; Procarbazine Hydrochloride; Puromycin; Puromycin Hydrochloride; Pyrazofurin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentosan Polysulfate Sodium; Pentostatin; Pentrozole; Perflubron; Perfosfamide; Perillyl Alcohol; Phenazinomycin; Phenylacetate; Phosphatase Inhibitors; Picibanil; Pilocarpine Hydrochloride; Pirarubicin; Piritrexim; Placetina; Placetin B; Plasminogen Activator Inhibitor; Platinum Complex; Platinum Compounds; Platinum-Triamine Complex; Porfimer Sodium; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin-Polyoxyethylene Conjugate; Proteasome Inhibitors; Riboprine; Rogletimide; Raf Antagonists; Raltitrexed; Ramosetron; Ras Farnesyl Protein Transferase Inhibitors; Ras Inhibitors; Ras-Gap Inhibitor; Retelliptine Demethylated; Rhenium Re 186 Etidronate; Rhizoxin; Ribozymes; Rii Retinamide; Rohitukine; Romurtide; Roquinimex; Rubiginone Bi; Ruboxyl; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Saintopin; Sarcnu; Sarcophytola; Sargramostim; Sdi I Mimetics; Senescence Derived Inhibitor I; Sense Oligonucleotides; Signal Transduction Inhibitors; Signal Transduction Modulators; Single Chain Antigen Binding Protein; Sizofuran; Sobuzoxane; Sodium Borocaptate; Sodium Phenylacetate; Solverol; Somatomedin Binding Protein; Sonermin; Sparfosic Acid; Spicamycin D; Splenopentin; Spongistatin I; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Tallimustine; Tamoxifen Methiodide; Tauromustine; Tazarotene; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Tretinoin; Triacetyluridine; Triciribine; Tropisetron; Turosteride; Tyrosine Kinase Inhibitors; Tyrphostins; Topoisomerase Inhibitors; Uracil Mustard; Uredepa; Ubc Inhibitors; Ubenimex; Urogenital Sinus-Derived Growth Inhibitory Factor; Urokinase Receptor Antagonists; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Variolin B; Vector System, Erythrocyte Gene Therapy; Velaresol; Veramine; Verdins; Vinorelbine; Vinxaltine; Vitaxin; Vinca Alkaloids; Zeniplatin; Zinostatin; Zorubicin Hydrochloride; Zanoterone; Zilascorb; and Zinostatin Stimalamer.

Examples of the infectious disease include, but are not limited to, HIV I and II, HBV, HCV disease, secondary disease states and conditions associated with infectious diseases.

Examples of the ischemia-induced disease include, but are not limited to, ischemia-induced neuronal death, stroke, traumatic brain injury, neonatal ischemic brain injury, ischemia reperfusion damage in heart or kidney.

It is believed that one skilled in the art can, based on the above description, utilize the present invention to its fullest extent without further elaboration. The following specific examples are to be construed as merely illustrative, and not limitative of the remainder of the disclosure in any way whatsoever. All publications cited herein are incorporated by reference.

Below are materials and methods used for preparing and testing the methods described above.

Reagents and Cell Culture

We obtained a list of 1312 FDA-approved drugs from MedChem Express (MCE). To validate hits, the drugs purchased from Enzo Life Science were used to screen drugs that inhibit ATG4 with biochemical, yeast and mammalian cell-based reporter assays. Human colorectal cancer HCT116 cells, glioblastoma H4 cells and breast cancer MDA-MB-231 from the ATCC were cultured in Dulbecco's modified Eagle's medium (DMEM) (Invitrogen, 12100-046) supplemented with 10% HyClone fetal bovine serum, penicillin (100 U/ml), and streptomycin (100 mg/ml). The cells were seeded into two- or three-dimensional culture dishes and treated with Doxorubicin (Dox, Millipore, 324380) or Camptothecin (CPT, Millipore, C9911) with or without tioconazole (Sigma-Aldrich, FL-32099). The treated cells were harvested to determine cell viability, apoptosis and immunoblotting. The detailed information previously described is provided in the supplementary experimental procedures. For gene knockdown, cells were transfected in the presence of 5 nM scrambled siRNA (Sigma, SIC002) or siRNA against ATG4 (Ambion, 35623 and 121998 for ATG4A, 20218, s23245 and s23246 for ATG4B, 34931 and 121984 for ATG4C, and 34865 and 149022 for ATG4D) using RNAiMAX (Life Technologies, 13778-150). To generate the shRNA stable cell line, shRNAs against ATG4B (TRCN0000073801), ATG5 (TRCN0000151963) and ATG7 (TRCN0000007584) obtained from The RNAi Consortium (TRC, Taiwan) were infected into HCT116 cells for stable selection. Plasmids for GFP-LC3 (21073) and Lamp1-RFP (1817) were purchased from Addgene and used to evaluate the fusion between autophagosomes and lysosomes via confocal microscopy as described below.

Docking and Explicit Solvent MD Simulations Used in Drug Screening and Inhibitory Mechanism Studies In silico drug screening for 1312 FDA-approved drugs were conducted in two stages. At first, docking software Vina (Trott and Olson, 2010) was used to evaluate potentially effective drug candidates based on three factors—(1) how many slightly different docking poses co-occupy the same binding site (Chang et al., 2007) (2) how far away these poses are from the active site of ATG4B(O) and (3) how favorable Vina-defined energies of individual poses are. Poses belonging to a large cluster (containing >8 poses in a binding pocket), having a short distance (<5 Å) from the active site, and bearing a low binding energy with ATG4B were selected and ranked by their docking affinity with the open-form ATG4B. Each of the top 100 candidates was then subject to MD simulations for the binding stability check. The drugs that left the binding pocket within 10 ns were deprioritized and those that stayed in the pockets were ranked based on binding energies calculated from MM/GBSA (Tsui and Case, 2000) as well as root mean square fluctuations (RMSF) of the distances between drugs and the active site. The trajectories of explicit solvent simulations at body-temperature were analyzed by Generalized-Born (GB) model or Poisson-Boltzmann (PB) model augmented with the hydrophobic solvent accessible surface area (SA) to obtain the binding energy of the drugs. The top-ranked 50 drugs that have the lowest binding energy (per GBSA or PBSA) and the highest stability (per RMSF) are selected and 22 of them could be readily purchased from the market for subsequent biochemical and cellular reporter assays (see below). More details on docking and simulations can be found in SI.

To understand the molecular mechanism of drug-mediated inhibition of LC3 proteolysis, we conducted further docking experiments for the best drug derived from our screening protocols by Autodock 4.0 (Morris et al., 2009). Open and closed ATG4B as well as the substrate LC3 serve as the targets for the small molecule docking. The stability of important docking poses was then examined by standard explicit-solvent MD simulations at 37° C., 1 atm, for tens or hundreds nanoseconds.

Structure Preparation

The open (PDB ID: 2Z0D) and closed (PDB ID: 2CY7) conformations of ATG4B feature two major distinctions: (A) in the closed form, the N-terminal tail of ATG4B folds in and covers the active site; in the open form, the tip of the LC3 C-terminus situated at the ATG4B active site and the N-terminus of ATG4B are held open by another crystallographically adjacent LC3 molecule. (B) In the closed form, the substrate-binding residue Trp142 forms close contacts with Pro260 in the regulatory loop (G257-A263), which makes the active site inaccessible to the substrate LC3. In the open form, Pro260 detaches from Trp142 and allows the LC3 C-terminus to dock. As a result, the open and closed conformations also suggest an "active" and "inactive" ATG4B, respectively.

ATG4 Reporter Assays

Biochemical ATG4 reporter assays were conducted as previously reported (Shu et al., 2010; Shu et al., 2011); recombinant ATG4B or ATG4A was mixed with substrate, 100 nM LC3B-PLA2 or GATE16-PLA2, in the presence or absence of tioconazole in the assay buffer. The fluorescence intensity was kinetically monitored for 1 h to determine the ATG4 activity at room temperature with excitation and emission wavelengths of 485 and 530 nm, respectively. Forty μl of the ATG4B reporter yeast cells previously described (Hayashi et al., 2009) were seeded in a 384-well white plate and grown on minimal synthetic dropout (SD) medium that contained 1% galactose, 0.2% raffinose, BU salts and Tryptophan for 24 h. Ten μl of Beta-Glo, a luminescent substrate for β-galactosidase, was added into each well to measure the β-galactosidase activity to reflect the ATG4B proteolysis activity. For the ATG4 cleavable reporter assay in mammalian cells, the N-terminus (NLuc, residues 2-416) and C-terminus (CLuc, residues 398-550) of the luciferase gene were constructed in the expression vector pcDNA3.0. The full length of LC3 was inserted to split NLuc and CLuc with two linkers (GGGGS)2 as shown in FIG. 1. The wild-type reporter vector was transfected into HEK293T cells in a 96-well white plate (Grinner) overnight and treated with tioconazole for 6 h. The luciferase activity was measured via One-Glo (Promega) according to the instruction manual. The non-cleavable mutant G120A was used to normalize the luminescent signal and determine the ATG4 activity.

Autophagic Flux and Immunoblotting

To monitor autophagy activity, the cells were treated with tioconazole (Sigma-Aldrich) in the presence or absence of 20 μM CQ (Sigma-Aldrich, C6628). The cells were briefly rinsed in PBS (Biological Industries, 02-023-1) and lysed with RIPA buffer (1% NP40 [MDBio, 101-9016-45-9], 50 mM Tris HCl, pH 7.5, 150 mM NaCl, 0.25% sodium deoxycholate [Sigma-Aldrich, D6750], 1% sodium dodecyl sulfate [SDS; Calbiochem, 428015], and protease inhibitor cocktail [Roche, 11873580001]). The cell lysates were used for immunoblotting with antibodies against the primary antibodies against ATG4B (A2981), LC3 (L7543), and ACTB (β-actin, A5441) (all purchased from Sigma-Aldrich). The differential accumulations of LC3 in cells with and without CQ were used to quantitate the autophagic flux (Mizushima et al., 2010). For cleavage of GABARAPL2-PLA2 and caspase-3 activation, reaction mixtures or cell lysates were immunoblotted with antibodies against Myc (Roche, 11667149001), caspase-3 (Cell Signaling, 9661), PARP (Cell Signaling, 9532) and GAPDH (Cell Signaling, 5174). The proteins were probed with an HRP-labeled secondary antibody (Santa Cruz, sc-2004 or sc-2005) and detected with an ECL reagent. The membrane was scanned and analyzed for the protein expression level with the ChemiDoc XRS Imaging System (Bio-Rad).

Tumor Xenograft

Human colorectal cancer HCT116 cells ($2 \times 10^6$) were mixed with Matrigel (1:1) and subcutaneously implanted into six-week old immunodeficient mice (nu/nu, female). Tioconazole (60 mg/kg) and Dox (1 mg/kg) were administered via intraperitoneal injection into the xenografted mice every other day starting at day 3 post-implantation. The tumor size in each mouse was measured every 3 to 4 days with vernier calipers, and the tumor volumes were calculated using the formula (larger diameter)×(smaller diameter)2× 7π/6. Tumors were further cut from euthanized mice and embedded in paraffin. The tumors were sectioned into 3 μm for antigen retrieval with EDTA buffer, pH 9.0, using a pressure cooker, followed by immunohistochemistry staining using an anti-LC3 monoclonal antibody (Nano Tools, 5F10, 1:50) and active caspase-3 (Asp175) (Cell signaling, 9661, 1:100), respectively. The protein levels in the tumor sections were determined using the UltraVision™ Quanto Detection System HRP DAB (Thermo Scientific) and observed under microscopy. All animal experiments were approved by the Institutional Animal Care and Use Committee at Kaohsiung Veterans General Hospital.

Bimolecular Fluorescence Complementation Assay

N- and C-terminal Venus expression plasmids, kindly provided by Gordon Mills (51), were used to construct the ATG4B and LC3 chimera genes, respectively. The plasmids (1 μg/well) were transfected with lipofectamine 2000 transfection reagent (Life Technologies, 11668-027) into HEK293T cells in a 6-well plate for 24 h. The cells were imaged via fluorescence microscopy or harvested to quantify the fluorescence intensity via a flow cytometer (Becton Dickinson).

Fluorescence Microscopy

Human glioma H4 cells that harbored GFP-LC3 were seeded onto 0.2% gelatin-coated glass dishes for 48 h and treated with tioconazole. The treated cells were fixed to observe the GFP-LC3 puncta via fluorescence microscopy. For protein colocalization, the H4 stable cells previously described were transfected with 1 μg plasmids Cherry tagged ATG4B or Lamp1-RFP (Addgene, 1817) for 36 h using Lipofectamine 2000 (Invitrogen). The cells transfected with ATG4B-Cherry or Lamp1-RFP were treated with tioconazole, fixed with 3.7% paraformaldehyde at room temperature for 15 min, and subsequently washed with PBS three times prior to observation using a confocal microscope.

Transmission Electron Microscopy (TEM)

HCT116 cells treated with T2 (40 µM), CQ (20 µM) for 8 h were rinsed with PBS once and fixed in 2% glutaraldehyde at room temperature for 30 min. The cells were harvested to postfix with 1% osmium tetroxide and stained with 2% uranyl acetate (Agar Scientific) at room temperature for 1 h. The cell pellets were embedded to obtain 80 nm sections with a diamond knife. The sections were stained with 2% uranyl acetate and 0.3% lead citrate (Agar Scientific) and imaged with a JEM1400 PLUS transmission electron microscope (JEOL).

Cell Viability Assay

Cells were seeded into a 384-well plate overnight and treated with various drugs for 24 h. CellTiter-Glo (Promega, Madison, Wis., USA) was subsequently added to the treated cells, and the luminescence was read using a Fluoroskan Ascent FL reader (Thermo Fisher Scientific). Alternatively, the cell viability was monitored with an impedance-based instrument system (iCELLigence, ACEA Biosciences) for live cells. Briefly, H4 cells, HCT116 cells and MDA-MB-23 cells ($4\times10^4$ cells/well) were seeded into electronic plates (E-Plates L8, ACEA Biosciences) with 400 µl of DMEM that contained 10% FBS and incubated for 30 h. The cells were pretreated with tioconazole (40 µM) for 1 h and subsequently treated with Dox (1 µM). The cellular impedance was periodically measured every 15 minutes until 80 h.

Real-Time PCR

The cells transfected with siRNA were used to extract the total RNA with TRIzol Reagent (Invitrogen, 15596-018). A total of 1 ng RNA was reverse-transcribed with SuperScript II RNase H-Reverse Transcriptase (Invitrogen, 18064-014) for cDNA synthesis. The amount of ATG4A, ATG4B, ATG4C and ATG4D mRNA relative to GAPDH was analyzed by real-time PCR performed in a StepOnePlus™ system (Applied Biosystems) with the SYBR Green Master Mix (Applied Biosystems, 4385612). The primers for the genes are as follows: ATG4A forward 5'-TGCTGGT-TGGGGATGTATGC-3' (SEQ ID NO: 1) and reverse 5'-GCGTTGGT ATTCTTTGGGTTGT-3' (SEQ ID NO: 2), ATG4B forward 5'-GATAGCGCAAATGGGAGTTGG-3' (SEQ ID NO: 3) and reverse 5'-CCACGTATCGAAGACA-GCAAG-3' (SEQ ID NO: 4), ATG4C forward 5'-TAGAG-GATCACGTAATTGCAGGA-3' (SEQ ID NO: 5) and reverse 5'-GTTGTCAAAGCTGAGCCTTCTAT-3' (SEQ ID NO: 6), and ATG4D forward 5'-GGAACAACGTCAAG-TACGGTT-3' (SEQ ID NO: 7) and reverse 5'-CTCGC CCTCGAAACGGTAG-3' (SEQ ID NO: 8) using GAPDH as normalization control.

Flow Cytometry for Mitochondrial Membrane Potential and Apoptosis

For the MMP analysis, the cells were treated with JC-1 (5,5,6,6-tetrachloro-1,1,3,3-tetraethyl-benzimidazolylcarbocyanine iodide, Invitrogen) at 37° C. for 20 min prior to harvesting. The JC-1 aggregates (red) and monomer (green) were used to determine the loss of MMP in cells following treatment. To determine the apoptotic cells, the cells were treated with Dox and tioconazole for 24 h and detached with accutase (eBioscience). The cells were stained with 5 µl of annexin V (AV)-fluorescein isothiocyanate (FITC) and 1 µl of propidium iodide (PI, 100 µg/ml) for 15 min according to the instruction manual (Invitrogen). The stained cells were analyzed for apoptosis and necrosis using FACScan (Becton Dickinson) and FlowJo (Tree Star) software.

Spheroid Cell Culture and Live/Dead Assay

The cells (4000 cells/well) were seeded into an ultra-low attachment, 96-well plate (Costar®, USA) and grown overnight to form spheroid cells. The cells were treated with tioconazole (40 µM) in the presence or absence of Dox (1 µM) for 48 h. The spheroid cells were stained with Calcein AM (1 µM) and Ethidium homodimer-1 (EthD-1, 2 µM) (LIVE/DEAD® Viability/Cytotoxicity Kit, ThermoFisher Scientific) for 30 minutes. The live (green) and dead (red) spheroid cells were imaged via fluorescence microscopy and quantitated using a Fluoroskan Ascent FL reader (Thermo Fisher Scientific) with excitation at 485 nm and emissions at 530 nm and 645 nm for calcein AM and EthD-1, respectively.

Statistical Analysis

All data are expressed as the mean±SEM from at least 3 individual experiments. The statistical analyses were performed using a nonparametric 2-tailed Student's t-test or an ANOVA with Tukey's post hoc test. P-values less than 0.05 were considered significant (*P<0.05, P<0.01, *P<0.001).

The following is a detailed description of the drawings.

Workflow of the in Silico Drug Screening for 1312 FDA-Approved Drugs.

FIG. 1 shows the workflow of the in silico drug screening for 1312 fda-approved drugs. The drugs were docked into the open form of ATG4B, and the results are sorted by clustered poses, distances between drugs and the active site, and the Vina-defined binding affinity. The top-ranked 100 drugs were further screened for their binding stability using 10 nanosecond explicit-solvent MD simulations at body temperature and subsequent MM/GBSA energy calculations.

Screening and Evaluation of Drugs for ATG4 Inhibition.

FIGS. 2-10 show the representative images of screening and evaluation of drugs for ATG4 inhibition. (FIG. 2) The ability of the 22 hits obtained from the in silico drug screening to inhibit ATG4 was evaluated using LC3-PLA2 biochemical assays (red dots) and ATG4 reporter yeast cells (green dots). EGTA (5 mM, red dot line) and NEM (10 mM, green dot line) were used as positive controls for biochemical and cellular ATG4 reporter assays, respectively. (FIG. 3) Tioconazole (Tc, 2.5 µM) was confirmed with ATG4 reporter yeast cells and LC3-PLA2 biochemical assay and counter assayed with caspase-1 reporter yeast cells for selectivity (left panel). Various concentrations of Tc were mixed with 0.5 nM caspase-3 and 100 µM Ac-DEVD-AFC to determine the effects of Tc on the caspase-3 activity (right panel). (FIG. 4) The activities of 2-fold serially titrated Tc and its analog miconazole on ATG4B were compared with an LC3-PLA2 assay. (FIG. 5) ATG4B (0.1 nM) or (FIG. 6) ATG4A (5 nM) was mixed with 2-fold serially diluted Tc and 100 nM GABARAPL2-PLA2 to determine the IC50 of Tc for ATG4 members. Quantitative results are shown in each panel (n=4). (FIG. 5) ATG4B (1 nM) or (FIG. 6) ATG4A (50 nM) was mixed with 10-fold serially diluted Tc and 500 nM GABARAPL2-PLA2 for 1 h. The cleavage of GABA-RAPL2-PLA2 was validated with immunoblotting using an anti-Myc antibody. (FIG. 7) The expression vector that encoded ATG4-cleavable luciferase was constructed with LC3 and a luciferase chimera gene, as shown in the schematic diagram (upper panel). HEK293T cells were transfected with scramble siRNA (siCtrl) or siRNA against ATG4B (siATG4B) for 48 h, followed by transfection with the ATG4 reporter vector for 24 h. The luciferase activity was measured with a luminescent reader (n=6), and the knockdown efficiency of ATG4B was determined using immunoblotting. (FIG. 8) HEK293T cells were transfected overnight with the ATG4 reporter vector as described in FIG. 10 and treated with Tc for 8 h to measure the luciferase activity (lower panel). The cleavage of LC3 and luciferase chimera protein by ATG4 in cells treated with Tc or untreated cells was verified via immunoblotting (upper panel). (FIG. 9) N-terminal Venus fused with ATG4B and C-terminal Venus fused with LC3 were co-transfected into HEK 293T cells. After overnight culture, the cells were fixed to observe Venus complementary under fluorescence microscopy (right panel). Bar: 100 μm. (FIG. 10) The transfected cells were treated with Tc for 8 h and fixed for flow cytometry to quantify Venus fluorescence using GFP as a counter assay. The results are expressed as the mean±SEM from at least 3 individual experiments. *p<0.05; p<0.01; *p<0.001.

Docking and MD Simulations for Tioconazole Binding to ATG4.

Figure 11:
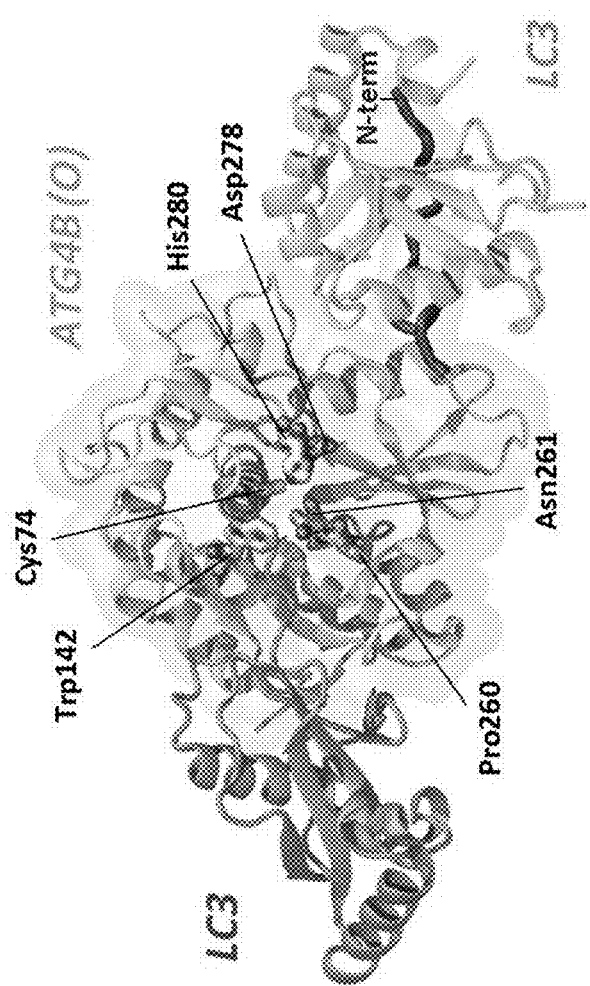
FIGS. 11-16 show the docking and MD simulations for tioconazole binding to ATG4.
Figure 12:
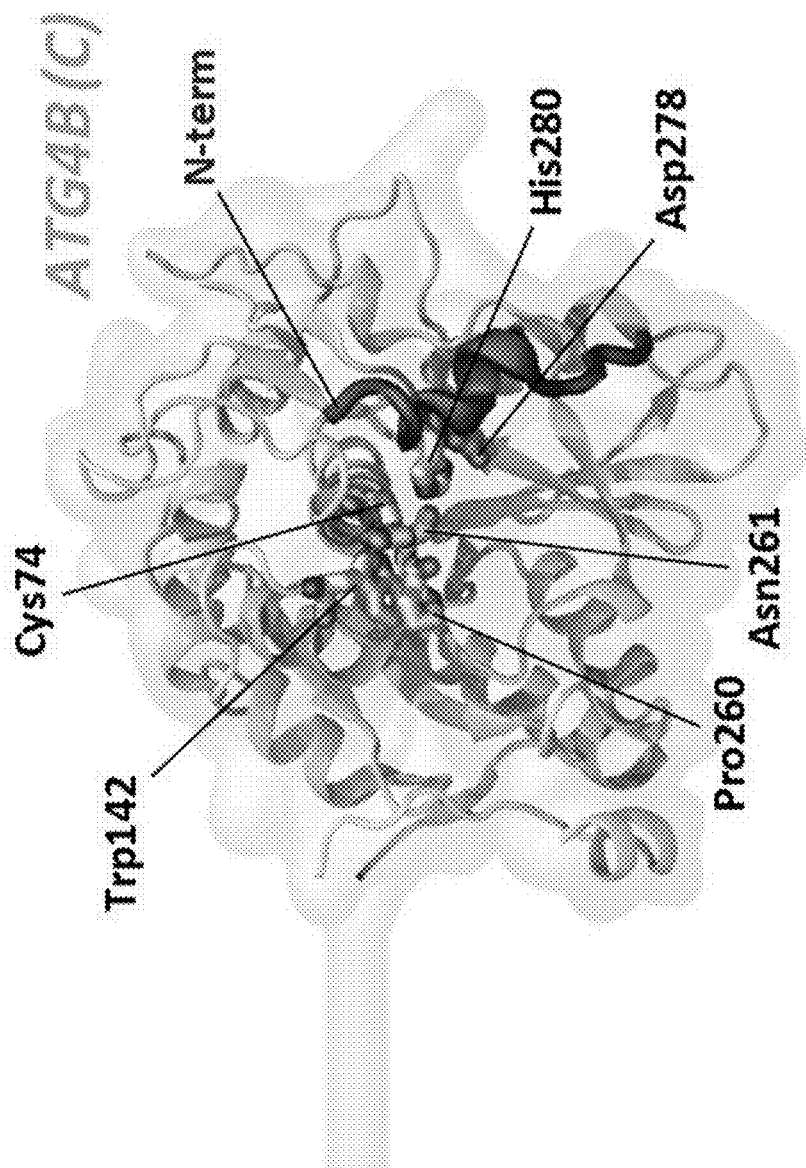
Figure 13:
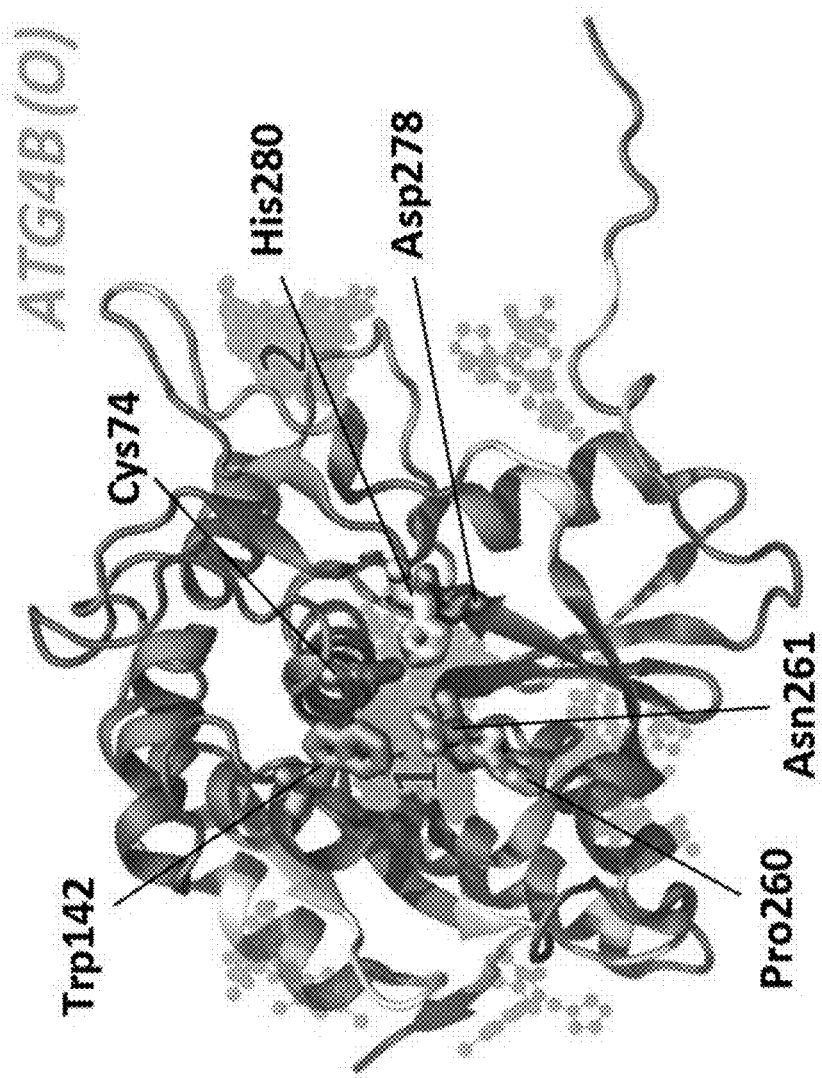
Figure 14:
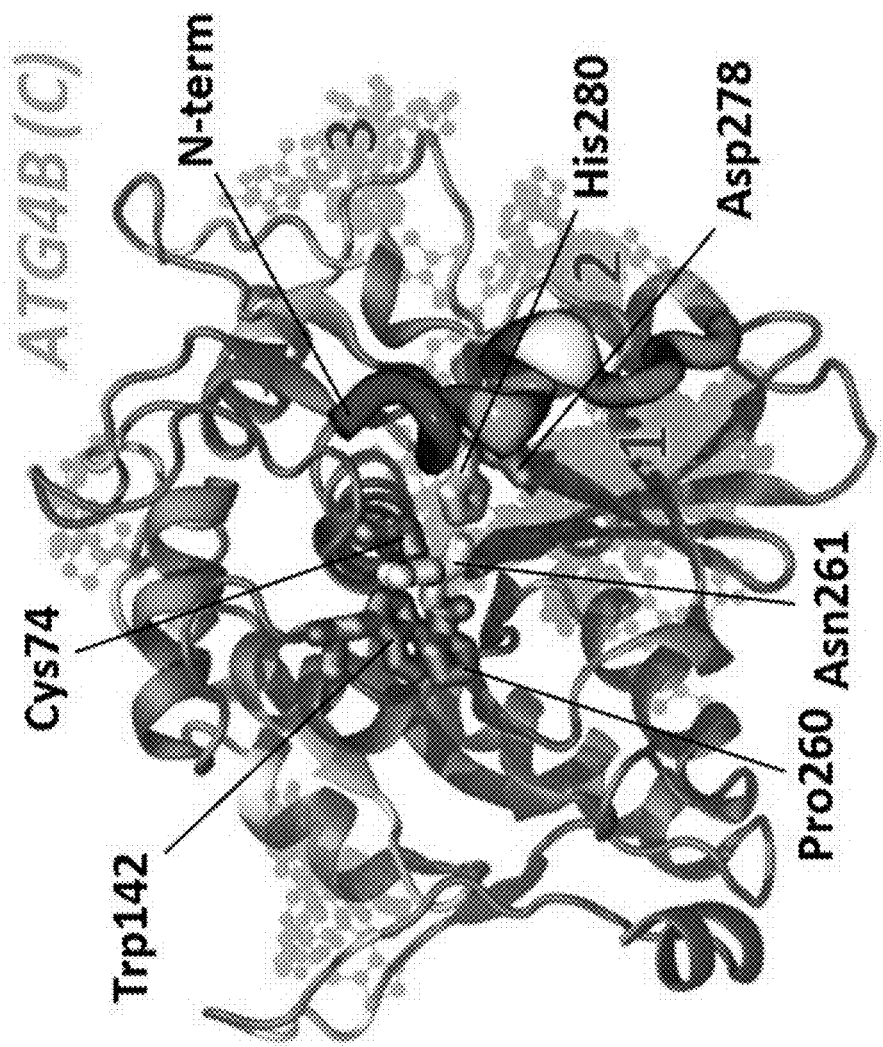
Figure 15:
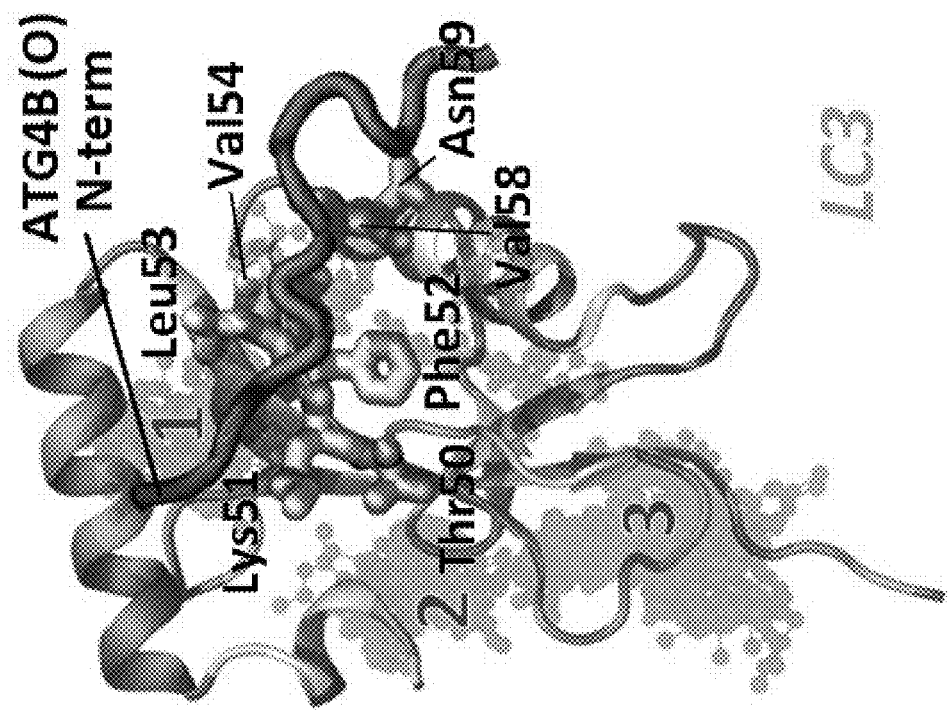
Figure 16:
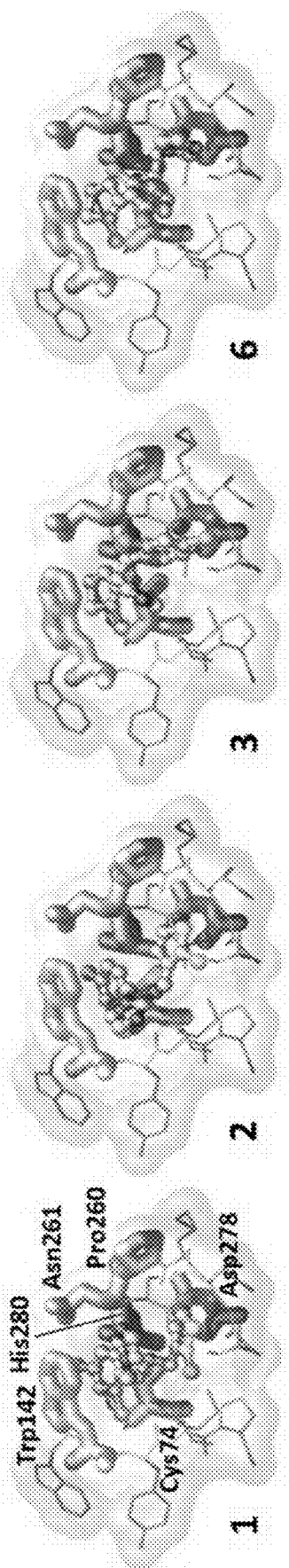

FIGS. 11-16 show the docking and md simulations for tioconazole binding to ATG4. (FIG. 11) The structures of the open/active (PDB code: 2Z0D, ATG4B (0)) and closed/inactive (PDB code: 2CY7, ATG4B (C)) forms of ATG4B are shown in FIG. 11 and FIG. 12 (in white), respectively. Together with the open form, LC3 with a cleaved C-terminus docked into the active site (red protein) and LC3 from one of the adjacent crystallographic unit cell (green protein) are shown. The active site of ATG4B consists of the residues Cys74 (the catalytic cysteine), Asp278 and His280, shown in licorice. The adjacent residues, Trp142, Pro260 and Asn261 (in licorice), form a substrate-binding cavity, with the latter two resides located at a regulatory loop that spatially flanks the cavity. Note the differences in the N-terminus positions in the open and closed forms of ATG4B. Panels C, D and E show the 100 docking poses obtained from AutoDock for the active (FIG. 13) and inactive (FIG. 14) forms of ATG4B as well as LC3 (FIG. 15). The residues of LC3 that interact with the N-terminal tail of ATG4B, observed via crystallography and later confirmed by NMR [35], are shown in thick licorice. Tioconazole is shown as a transparent green ball-and-stick structure, and residues in proteins are color-coded in blue (infrequent)→white→red (frequent) by the number of times they are in contact with ligands for the examined 100 docking poses (within 4 Å). The spatial "regions" that indicate the locations of clustered poses identified by AutoDock (see the rightmost column in Tables 1) are numbered in red. The docking results for clusters 1, 2, 3 and 6, rank-ordered, are shown in panel (FIG. 16). Tioconazole is shown as a ball-and-stick structure, and the active site residues Cys74, Asn278, and His280 as well as the adjacent residues Trp142, Pro260 and Asn261 are presented in thick licorice. Surrounding residues with atoms in close contact (<4 Å) with tioconazole are shown in thin licorice. Transparent clouds are colored in blue→white→red to show atoms with an increased frequency of contacts with tioconazole, summing all 100 docking poses. Also see FIG. 60-65.

Effects of Tioconazole on Autophagic Activity in Cancer Cells.

FIGS. 17-26 show the effects of tioconazole on autophagic activity in cancer cells. (FIG. 17) Human glioma H4 cells that stably express GFP-LC3 were transfected with 5 nM non-targeting siRNA (Ctrl) or siRNA against ATG4 family members (ATG4) for 48 h, and the knockdown efficiency of ATG4 was verified with real time PCR. (FIG. 18) The knockdowned cells were fixed for observation via fluorescence microscopy, and the number of GFP-LC3 puncta is quantified in the right panel. Bar: 20 μm. (FIG. 19) The cells that stably express GFP-LC3 were treated with tioconazole for 8 h and fixed to observe the GFP-LC3 puncta, which were (FIG. 20) quantified via fluorescence microscopy. The autophagy inhibitor CQ was used as a positive control. Bar: 20 μm. (FIG. 21) HCT16 cells treated with tioconazole (Tc, 40 μM) or CQ (20 μM) for 6 h were fixed and imaged with TEM. Representative autophagic vacuoles (AVs) are shown. Arrowhead: autophagosome. Bar: 200 nm. (FIG. 22) The numbers of AVs for each optical section (9 m$^2$) are quantified (n=8). (FIG. 23) HCT116 cells expressing GFP-LC3 and RFP-Lamp1 were treated with Tc for 6 h and fixed to observe colocalization of GFP-LC3 and RFP-Lamp1 with confocal microscopy. GFP-LC3 that had colocalized with or was surrounded by RFP-Lamp1 was identified as fusion between autophagosomes and lysosomes. The colocalization coefficients of images were quantified by the Ziess LSM 710 Software and are shown in the right panel. Bar: 20 m. (FIG. 24) HCT16 cells were transfected with siRNA (5 nM) for 66 h and then treated with CQ (20 μM) for 2 h. Cells were harvested for immunoblotting using antibodies against LC3, ATG4B or ACTB, and autophagy flux was quantified in untreated cells and cells treated with CQ based on changes in LC3-II. (FIG. 25) H4, HCT116 or MDA-MB-231 cells were treated with Tc for 6 h in the presence (+) or absence (−) of CQ (20 VM) and harvested for immunoblotting. (FIG. 26) The autophagic flux was quantified as described in FIG. 25. Representative data are shown, and the quantified results are expressed as the mean±SEM from at least 3 individual experiments. *p<0.05; p<0.01; *p<0.001.

Tioconazole Sensitizes Cancer Cells to Starvation and Chemotherapeutic Drugs.

FIGS. 27-36 show that tioconazole sensitizes cancer cells to starvation and chemotherapeutic drugs. (FIG. 27) H4, (FIG. 28) HCT116 or (FIG. 29) MDA-MB-231 cells were starved in FBS-free media or EBSS in the presence or absence of tioconazole (40 μM) for 24 h. The cytotoxicity of these treatments was assessed using CellTiter-Glo. (FIG. 30) H4, (FIG. 31) HCT116 and (FIG. 32) MDA-MB-231 cells were treated with the anticancer drug CPT (1.5 μM) or Dox (1 μM) for 24 h in the presence or absence of tioconazole, and cell viability was measured with CellTiter-Glo. The immunoblotting results of LC3-II and SQSTM1 for the cells as aforementioned were shown in each panel. (FIG. 33) HCT116 cells were cultured in electronic plates and treated with Dox (1 μM) in the presence or absence of Tc (40 μM) to monitor cell viability in live cells with an impedance-based system. (FIG. 34) HCT116 cells treated with Tc or (FIG. 35) its analog Mc in the presence or absence of Dox (1 μM) for 24 h were harvested for FACS-based cell cycle distribution analysis or to quantify the subG1 population with FlowJo. (FIG. 36) HCT116 cells were transfected with 5 nM scramble siRNA (siCtrl) or siRNA against ATG4 (siATG4) for 56 h. The transfected cells were treated with Dox or Tc for 24 h, and the cell viability was measured with CellTiter-Glo. The knockdown efficiency of siRNA against ATG4 was confirmed by immunoblotting in cells transfected with HA-tagged ATG4 members. The results are expressed as the mean±SEM from 3 individual experiments. n.s., p>0.05; *p<0.05; p<0.01; *p<0.001.

Effects of Tioconazole on Chemotherapy-Induced Apoptosis in Cancer Cells.

FIGS. 37-43 show the effects of tioconazole on chemotherapy-induced apoptosis in cancer cells. (FIG. 37) HCT116, (FIG. 38) H4 and (FIG. 39) MDA-MB-231 cells were treated with Dox (1 µM) for 24 h in the presence or absence of tioconazole (Tc, 40 µM), and apoptotic cells were stained with PI/AV. The apoptotic cells were analyzed and quantified with Prism 5.0. (FIG. 40) The treated cells as (A) were stained with JC-1 to determine the mitochondrial membrane potential. The representative data and quantitative results are shown in the left and right panels, respectively. (FIG. 41) Untreated HCT116 cells or HCT116 cells treated with zVAD-FMK (50 µM) as described in FIG. 37 were harvested to assess caspase-3 activation with Caspase-Glo 3/7 luminescent assay. (FIG. 42) HCT116 cells treated as FIG. 39 were harvested for immunoblotting using antibodies against caspase-3 or PARP. (FIG. 43) H4, HCT116 and MDA-MB-231 cells were pretreated with zVAD-FMK (50 µM), Tc (40 µM) or CQ (20 µM) prior to treatment with Dox (1 µM) for 24 h, and the cell viability was measured. The results are expressed as the mean±SEM from at least 3 individual experiments. *$p<0.05$; $p<0.01$; *$p<0.001$.

Effects of Tioconazole on Chemosensitivity in Tumor Spheroid Culture and Xenograft Mouse Model.

FIGS. 44-54 show the effects of tioconazole on chemosensitivity in tumor spheroid culture and xenograft mouse model. (FIG. 44) HCT116 cells were cultured in an ultra-low attachment dish for 24 h to form spheres. The cells were treated with Dox (1 µM) in the presence or absence of Tc (40 µM) for 48 h and stained with Hoechst 33342 (1 µg/ml) to image the spheres. Scale bar: 400 µm. (FIG. 45) The relative sphere volume was quantified using DMSO-treated cells as the normalized control. (FIG. 46) HCT116 sphere-forming cells treated as (A) were lysed to measure ATP levels and assess cell viability. (FIG. 47) HCT116 cells harboring shRNA against ATG4B, ATG5 or ATG7 formed spheres and were treated with Tc (40 µM) or CQ (20 µM) in the presence or absence of Dox (1 µM) for 48 h. The viable and dead spheres were imaged with a LIVE/DEAD staining kit. The knockdown efficiency of ATG genes was verified by immunoblotting (left panel) (FIG. 48) The red fluorescence of the spheres in FIG. 47 was quantitated with a reader to assess the dead cell population (n=6). The quantified results are expressed as the mean±SEM from 3 individual experiments. (FIG. 49) Mice injected with $2\times10^6$ human colorectal cancer HCT116 cells were treated with Tc (60 mg/kg) in the presence (+) or absence (−) of Dox (1 mg/kg) every other day. The tumor volume (circle) in each mouse was measured every 3 to 4 days (5 per group). The p values were determined with an ANOVA. (FIG. 50) The representative pictures of the xenograft tumors and tumor weight at day 21 after injection were shown in the left and right panel, respectively. Scale bar: 1 cm. (FIG. 51) The xenografted tumor was harvested and embedded for immunohistochemistry using an antibody against LC3. Arrow: cells with LC3 puncta. Scale bar: 40 µm. (FIG. 52) The number of LC3 puncta in each cell was counted for at least 150 cells and quantified. (FIG. 53) The level of cleaved caspase-3 in sections prepared as FIG. 51 was determined with immunohistochemistry as shown in the left panel. Arrow: apoptotic cell. Scale bar: 20 µm. n.s. (FIG. 54) The cleaved caspase-3-positive cells with condensed nuclei were counted as apoptotic cells. The quantified results were obtained from at least 1500 cells and are shown in the right panel. $p>0.05$; *$p<0.05$; $p<0.01$; *$p<0.001$.

Characterization of Yeast Based ATG4B Reporter Assay for HTS.

FIGS. 55-58 show the characterization of yeast based ATG4B reporter assay for hts. (FIG. 55) Two-fold serial titrated yeast that harbored the LC3 reporter with wild type ATG4B (WT) or catalytic mutant (C74A) expression vector and reporter vector were seeded into a 384-well plate for 24 or 48 h. The substrate of β-galactosidase X-gal (80 µg/ml) was included in the SD medium for the colorimetric assay. (FIG. 56) Beta-Glo was added into each well as (A) at 24 or 48 h to optimize the yeast concentration for the luminescent substrate. (FIG. 57) Yeast that harbored the wild type (WT) ATG4B and catalytic mutant (C74A) were used to determine the ratio of signal (WT)/background (C74A) and compare the sensitivity between the colorimetric and luminescent substrates. (FIG. 58) Forty L1 of yeast reporter cells (1.5× $10^4$ cells/ml) as previously described were seeded into a 384-well white plate for 24 h. Ten µl of the luminescent substrate Beta-Glo was added to each well, and the luminescent signal was read to determine the ATG4B activity. The luminescent signal between the wild type (WT) ATG4B and catalytic mutant (C/A) was used to determine the assay robustness (Z' factor: 0.78). The results are expressed as the mean±SEM from 3 individual experiments.

Tioconazole Interferes with Interaction of ATG4 and LC3.

Figure 59:
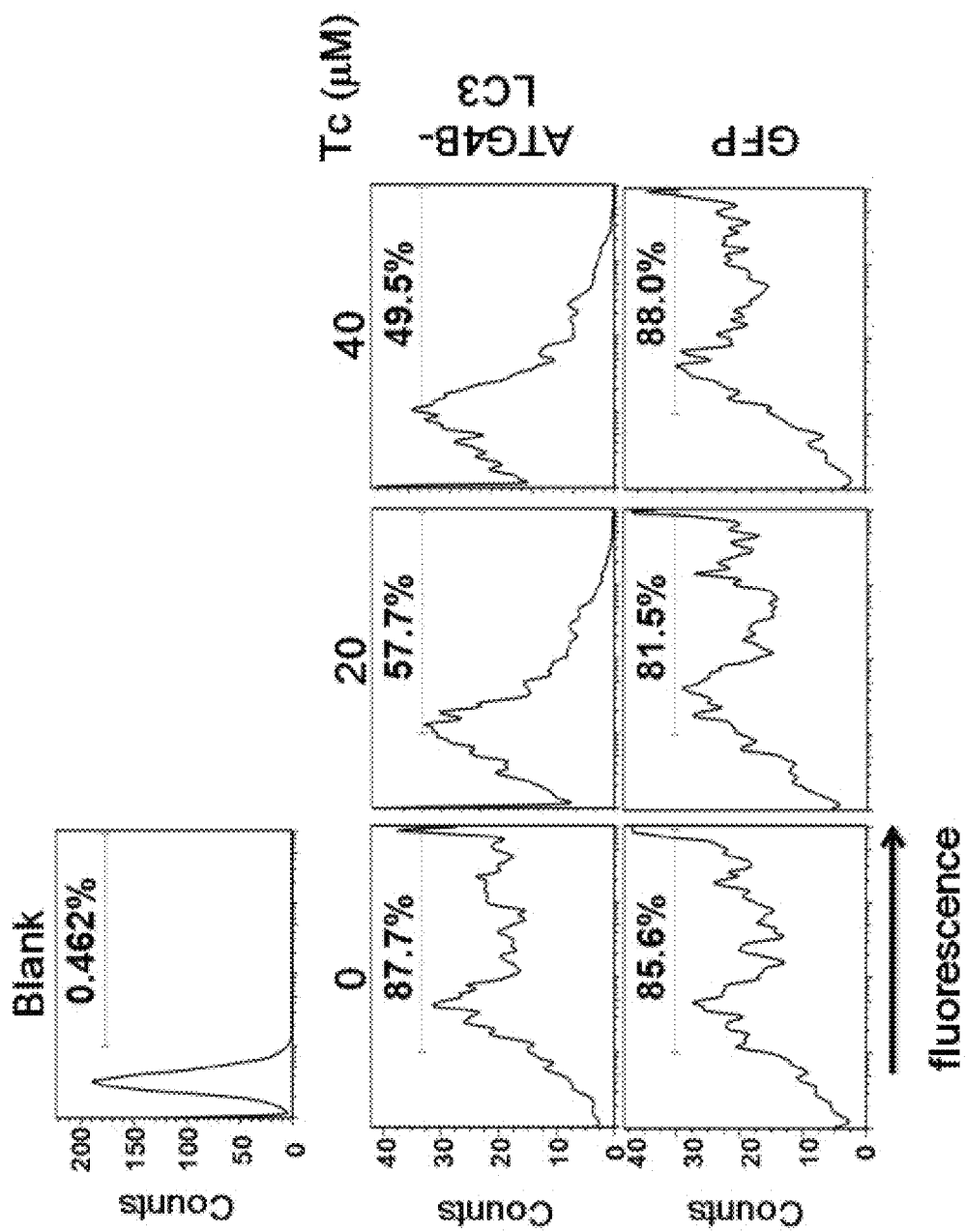
FIG. 59 shows that tioconazole interferes with interaction of ATG4 and LC3.

FIG. 59 shows that tioconazole interferes with interaction of ATG4 and LC3. N-terminal Venus fused with ATG4B and C-terminal Venus fused with LC3 were used to co-transfect into HEK 293T cells overnight and were treated with Tc for 8 h. The cells were fixed to determine Venus complementation with flow cytometry and quantitated with FlowJo. HEK 293T cells transfected with or without GFP expression vector were used as the blank and counter controls, respectively. The results are expressed as the mean±SEM from 3 individual experiments.

Tioconazole Also Docks into the Active Site of ATG4A.

Figure 60:
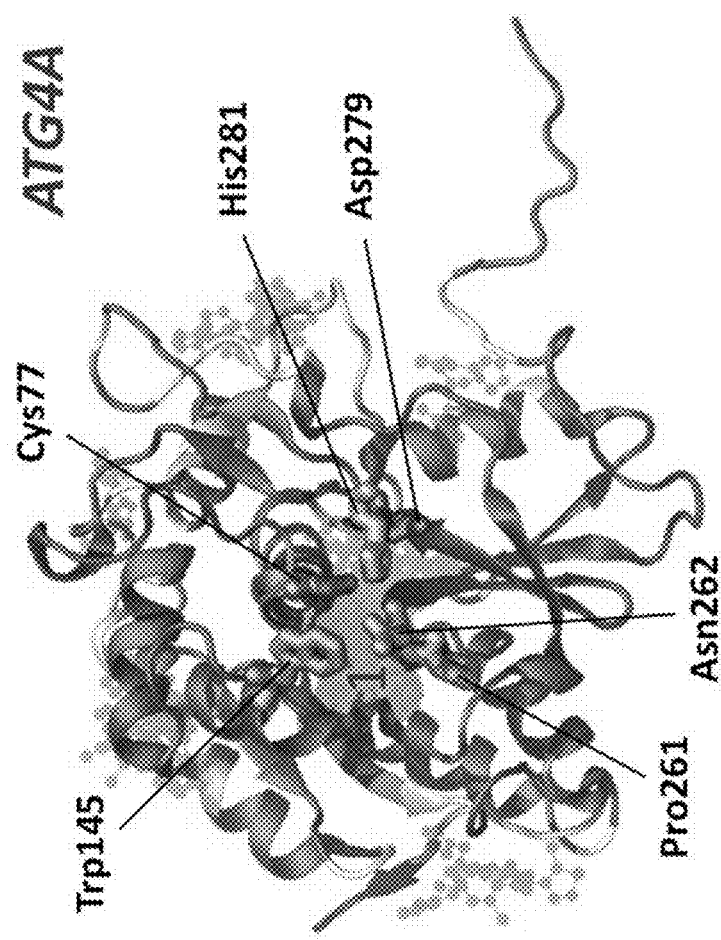
FIGS. 60-61 show that tioconazole also docks into the active site of ATG4A.
Figure 61:
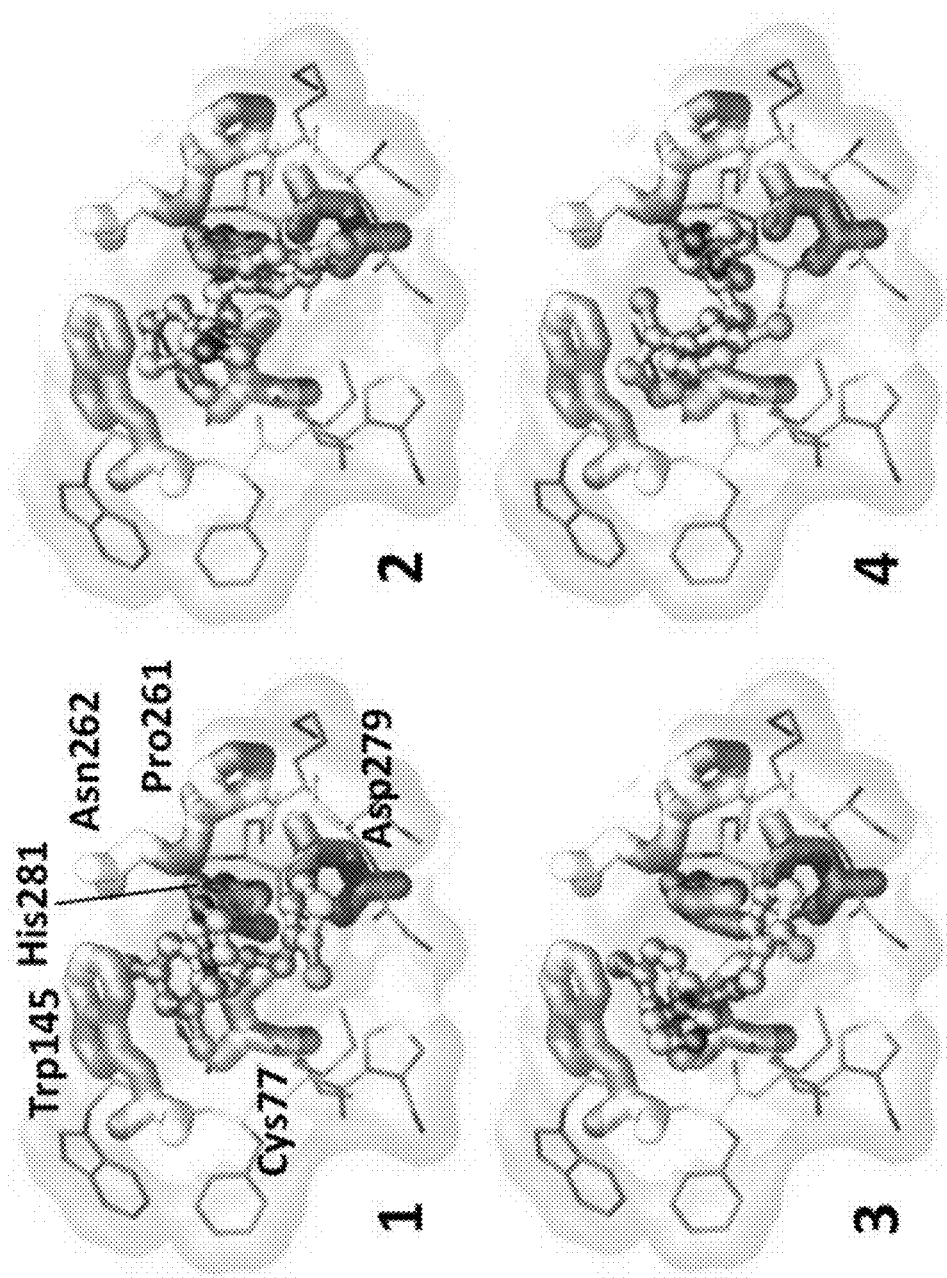
Figure 62:
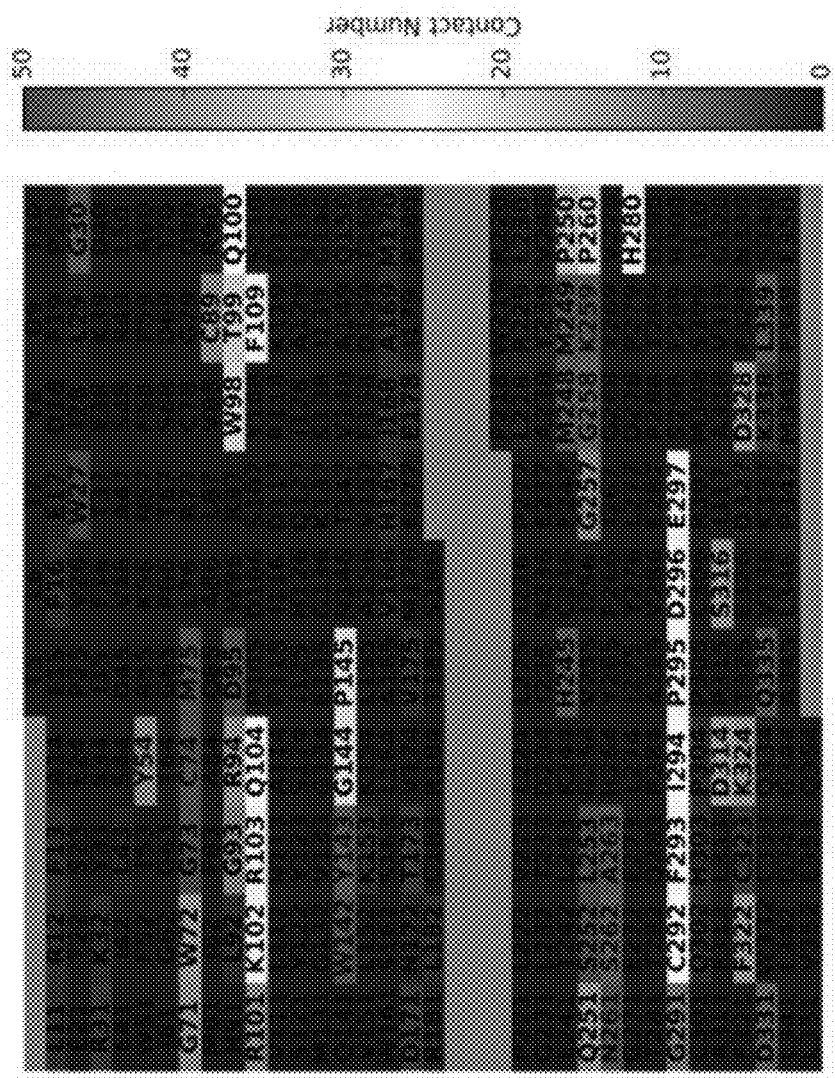
FIGS. 62-65 show the heat map of residue contact frequencies by tioconazole.
Figure 63:
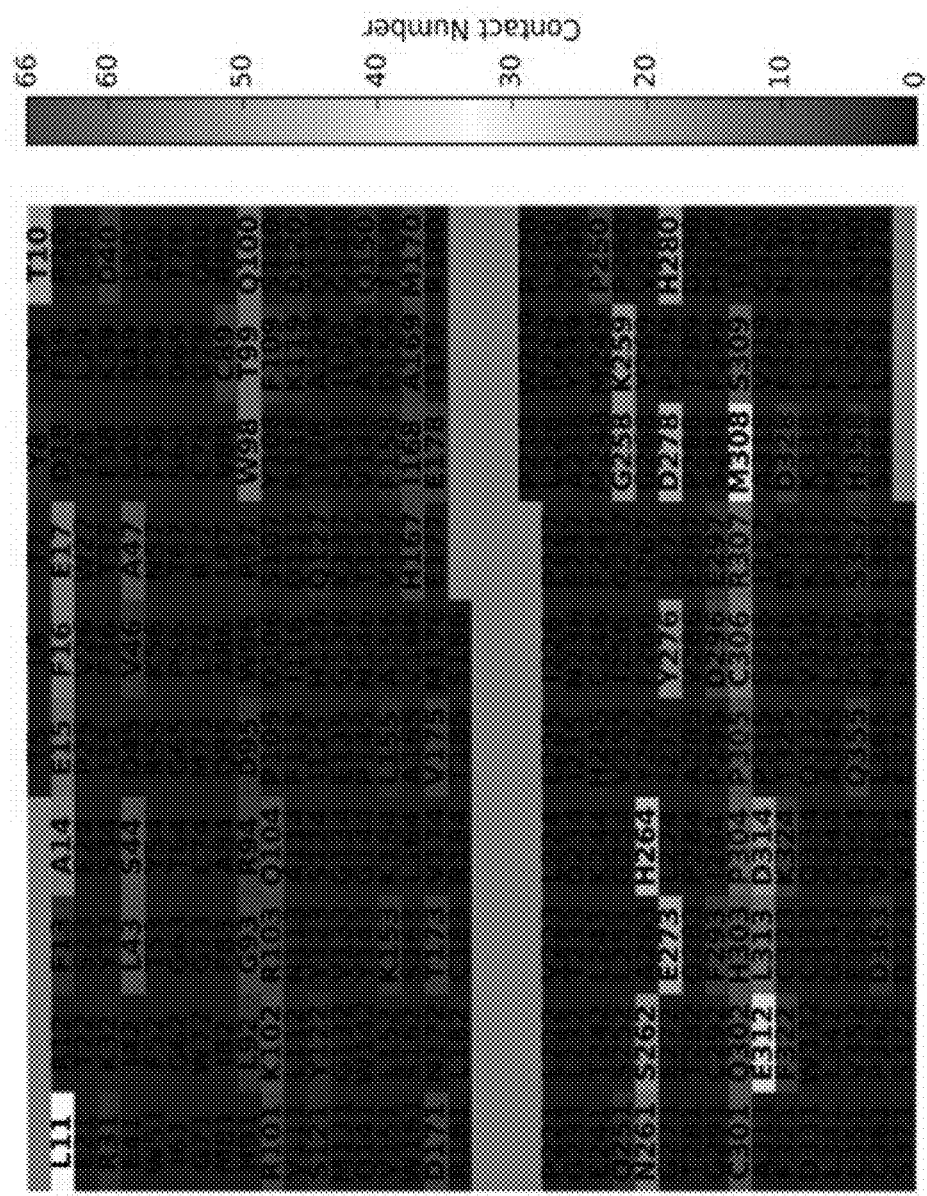
Figure 64:
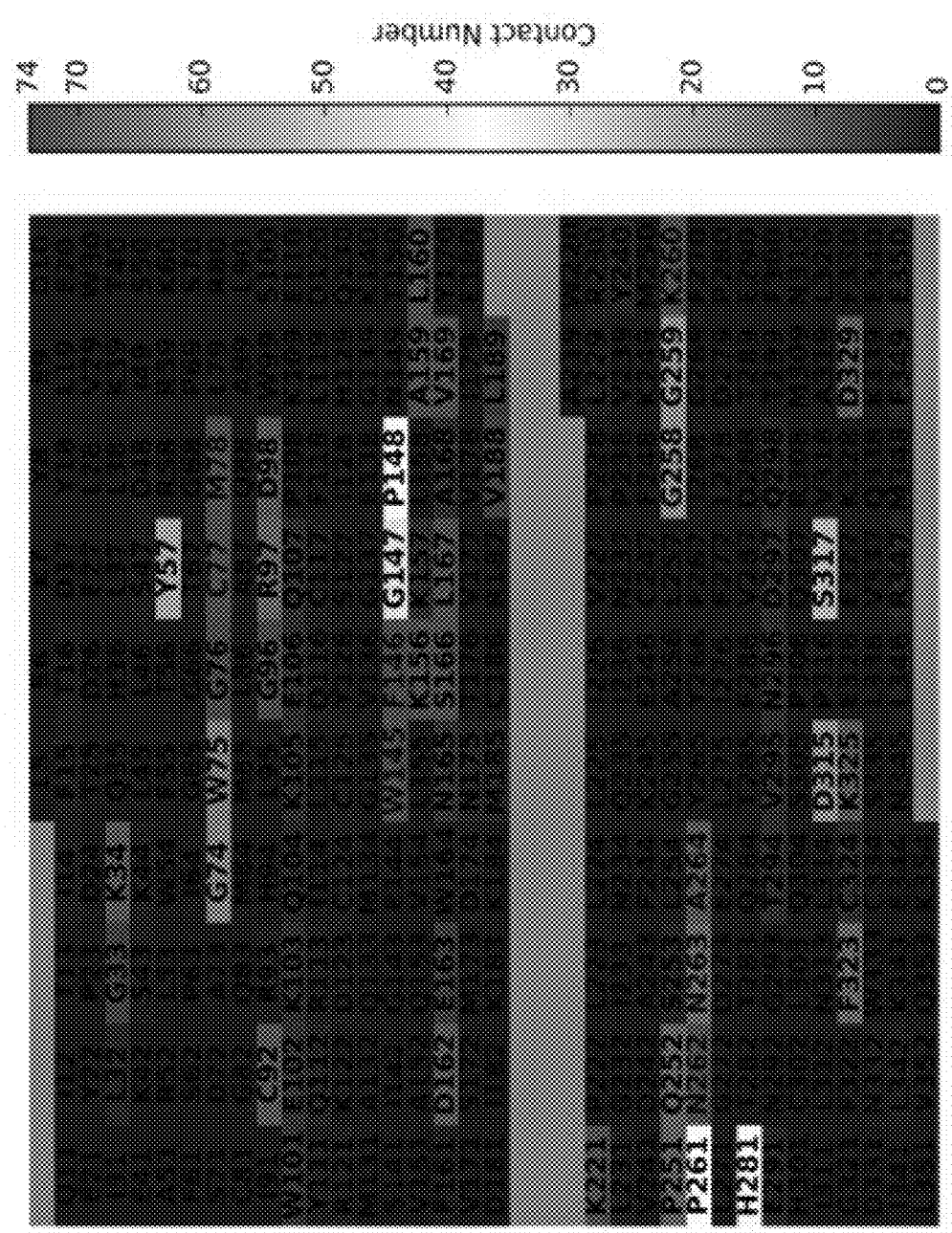

FIGS. 60-61 show that tioconazole also docks into the active site of ATG4A. The 100 docking poses in the open/active structure of ATG4A are obtained from AutoDock (FIG. 60), and the lowest energy pose in each of the four highest scored clusters (rank-ordered by their lowest energy pose) is shown in (FIG. 61). The spatial "regions" that indicate the locations of the clustered poses identified by AutoDock (Tables 1) are labeled (red number). The open/active forms of the ATG4A structure are constructed by the SWISS-MODEL web server (Biasini et al., 2014) using the ATG4B open form (PDB: 2Z0D) as the structural template. The color scheme is the same as shown in FIG. 2-10. Note that pose 1 here is almost in the same orientation as pose 1 (FIG. 16) for the open form of ATG4B. We selected the highest ranked four poses shown in FIG. 61 for further MD simulations. The results demonstrate that the ligands of poses 1, 3 and 4 remain at the binding pocket throughout the entire 100 ns of simulations. The docking pose for the pose 1 ligand after the 61st ns of the simulation resembles pose 2 in the simulation for ATG4B (0) except for a different direction where the imidazole ring points. For pose 2, the ligand leaves the binding pocket after 75.8 ns. For pose 4, although the ligand stays around the binding pocket throughout the 100 ns simulations, it notably changed its binding orientation and position.

Heat Map of Residue Contact Frequencies by Tioconazole.

Figure 65:
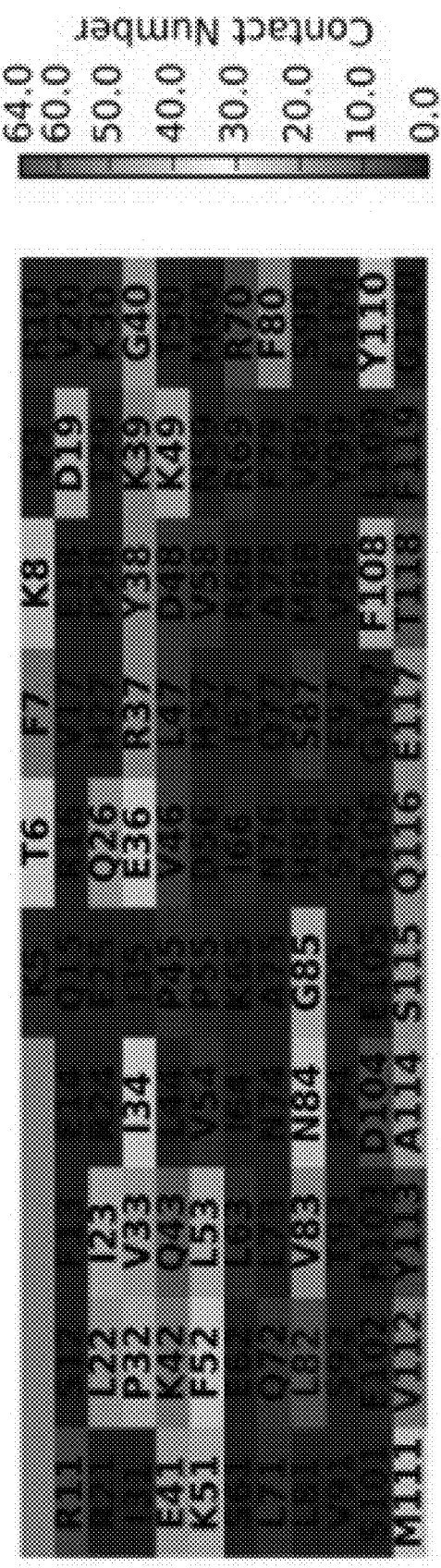

FIGS. 62-65 show the heat map of residue contact frequencies by tioconazole. Residue contact frequencies are calculated for the open/active (ATG4B (0), FIG. 62) and closed/inactive (ATG4B (C), FIG. 63) forms of ATG4B, and the open/active form of ATG4A (FIG. 64) and LC3 (FIG. 65). Frequency for each residue, colored blue→white→red in increasing order of contacts, is calculated by summing the number of poses (from 100 overall) in which tioconazole remains within 4 Å from a specific residue. Gray areas represent missing residues that are not included in the docking experiment.

Effects of Tioconazole on Fusion Between Autophagosome and Lysosome.

Figure 66:
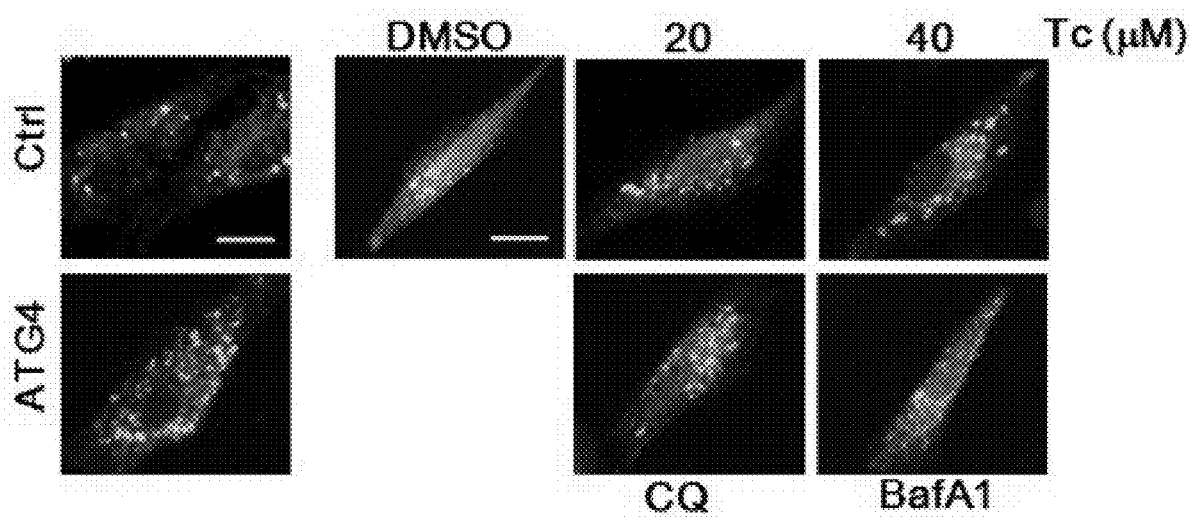
FIG. 66 shows the effects of tioconazole on fusion between autophagosome and lysosome.
Figure 66:
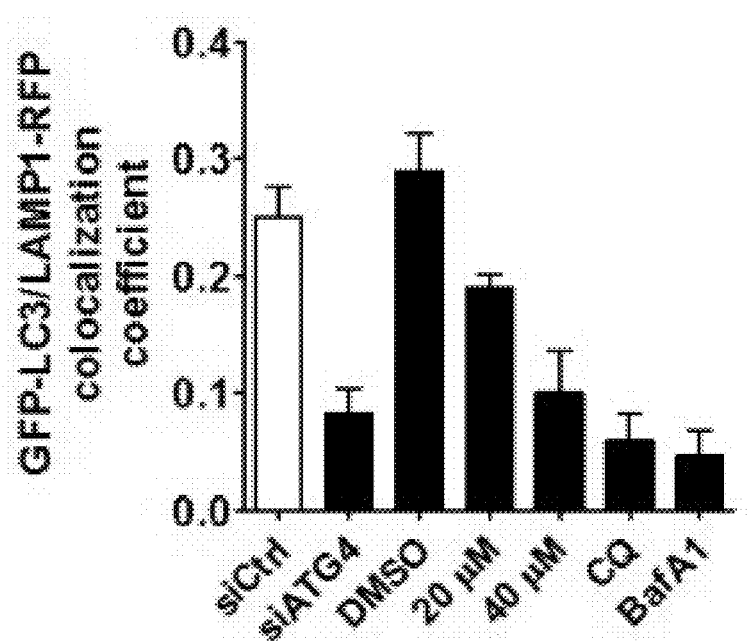

FIG. 66 shows the effects of tioconazole on fusion between autophagosome and lysosome. H4 cells expressing GFP-LC3 and RFP-Lamp1 were treated with Tc for 6 h and fixed to observe colocalization of GFP-LC3 and RFP-Lamp1 with confocal microscopy. The GFP-LC3 colocalized or surrounded by RFP-Lamp1 was identified as fusion between autophagosomes and lysosomes. The colocalization coefficients of images were quantified by the Ziess LSM 710 Software and shown in right panel. Bar: 20 µm.

Tioconazole Enhanced Dox-Induced Apoptosis in Cancer Cells.

Figure 67:
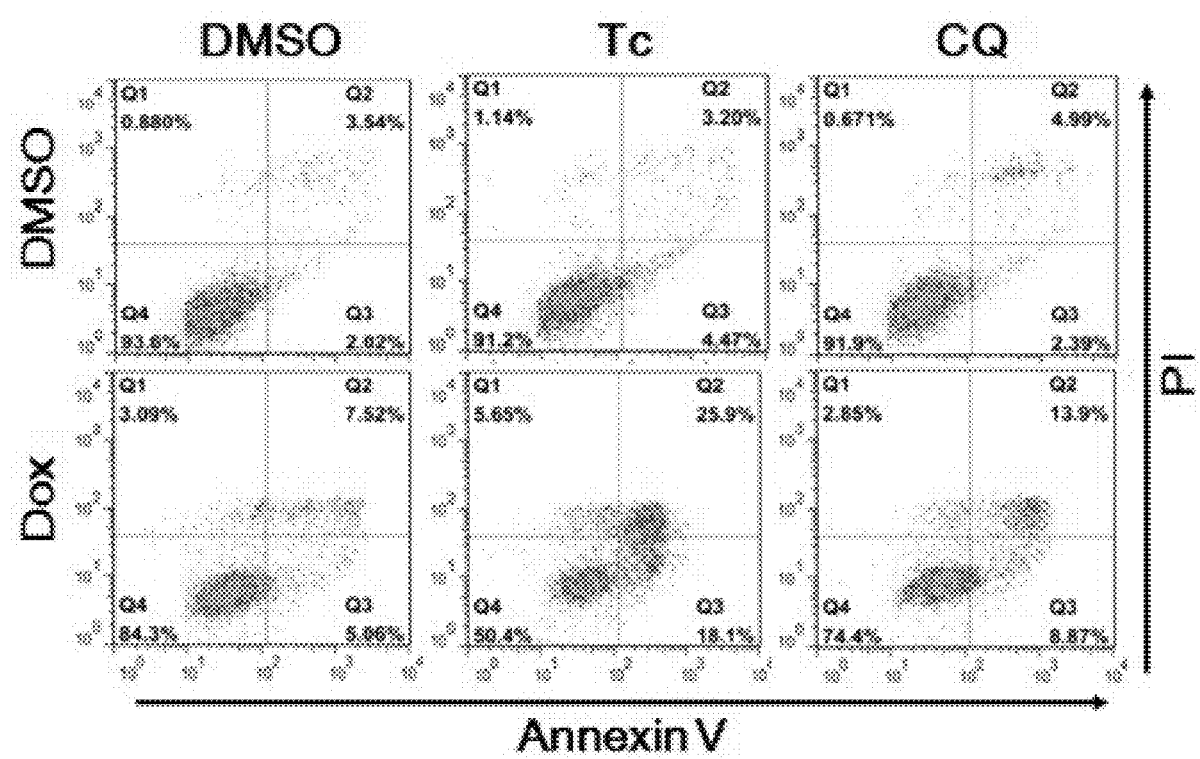
FIGS. 67-69 show that tioconazole enhanced Dox-induced apoptosis in cancer cells.
Figure 68:
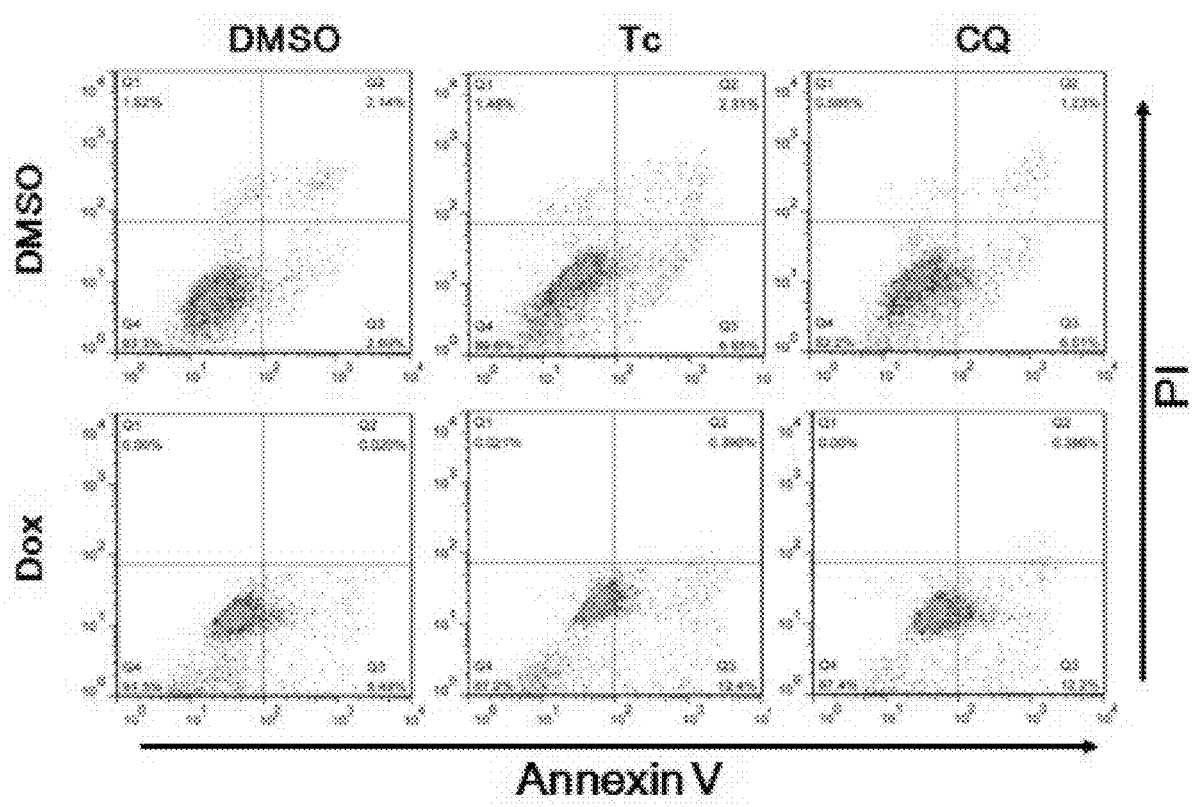
Figure 69:
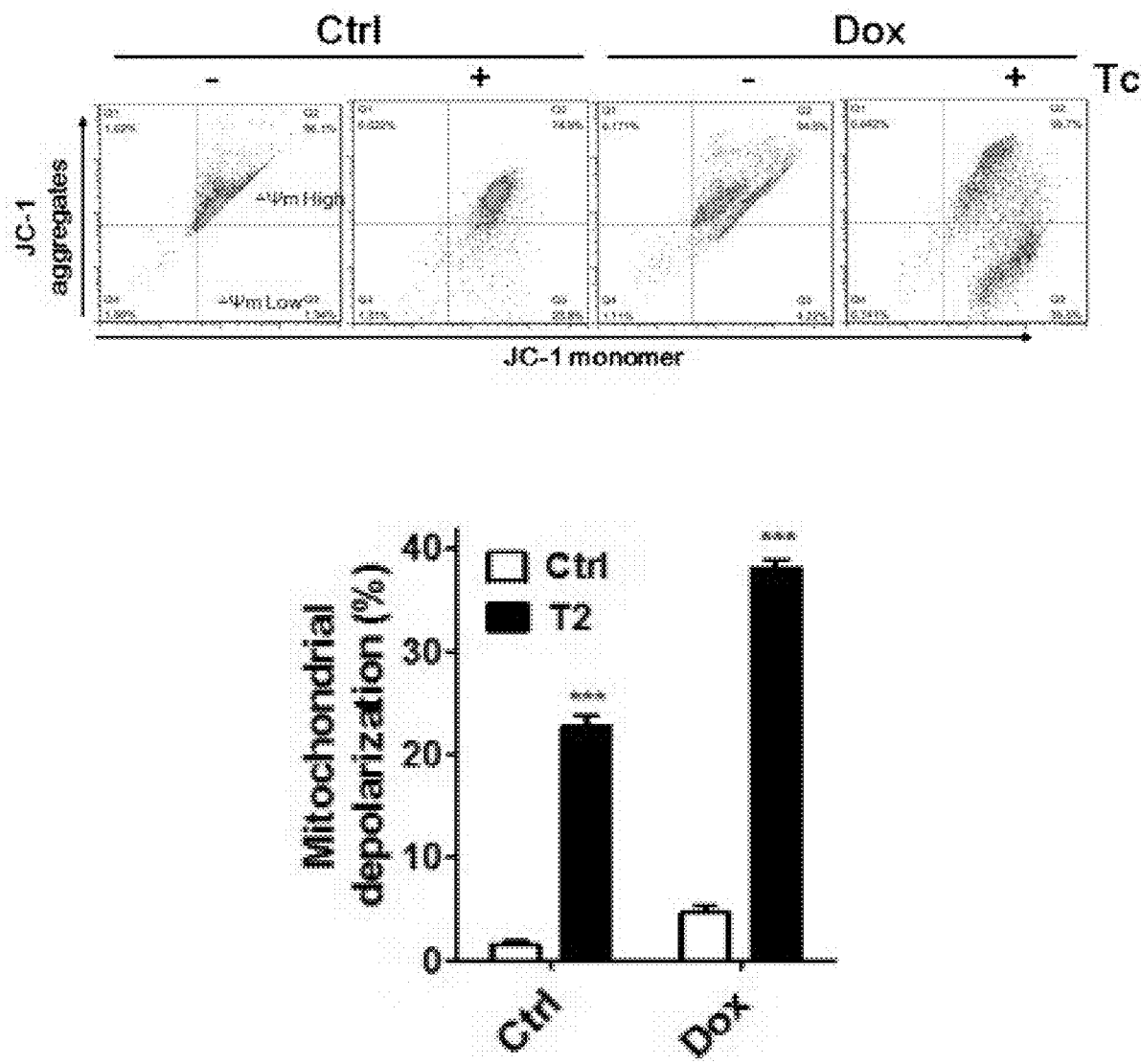

FIGS. 67-69 show that tioconazole enhanced dox-induced apoptosis in cancer cells. (FIG. 67) H4 and (FIG. 68) MDA-MB-231 cells treated with Dox (1 µM) for 24 h in the presence or absence of TC (40 µM) were harvested and stained with PI/AV. The early (PI$^-$/AV$^+$) and late (PI$^+$/AV$^+$) apoptotic cells were analyzed via flow cytometry. (FIG. 69) H4 cells were treated with Dox (1 µM) for 24 h in the presence or absence of Tc (40 µM) and stain with JC-1. The JC-1 stained cells were utilized to determine the mitochondria membrane potential with flow cytometry. The representative data and quantitative results are shown in the left and right panels, respectively. The results are expressed as the mean±SEM from 3 individual experiments.

The Effects of Silencing ATG4 and Tioconazole on Cathepsin B Activity.

Figure 70:
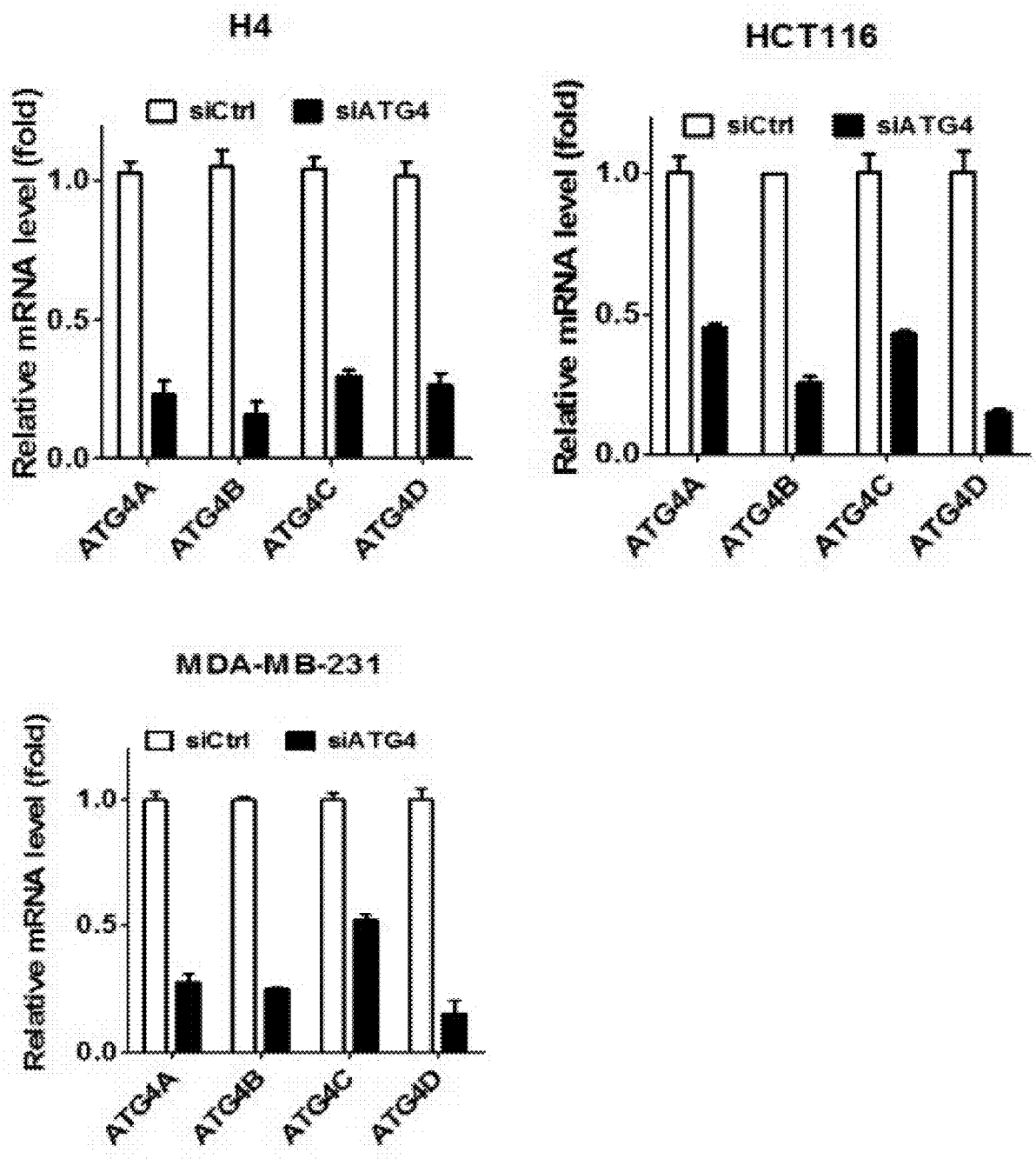
FIGS. 70-72 show the effects of silencing ATG4 and tioconazole on cathepsin b activity.
Figure 71:
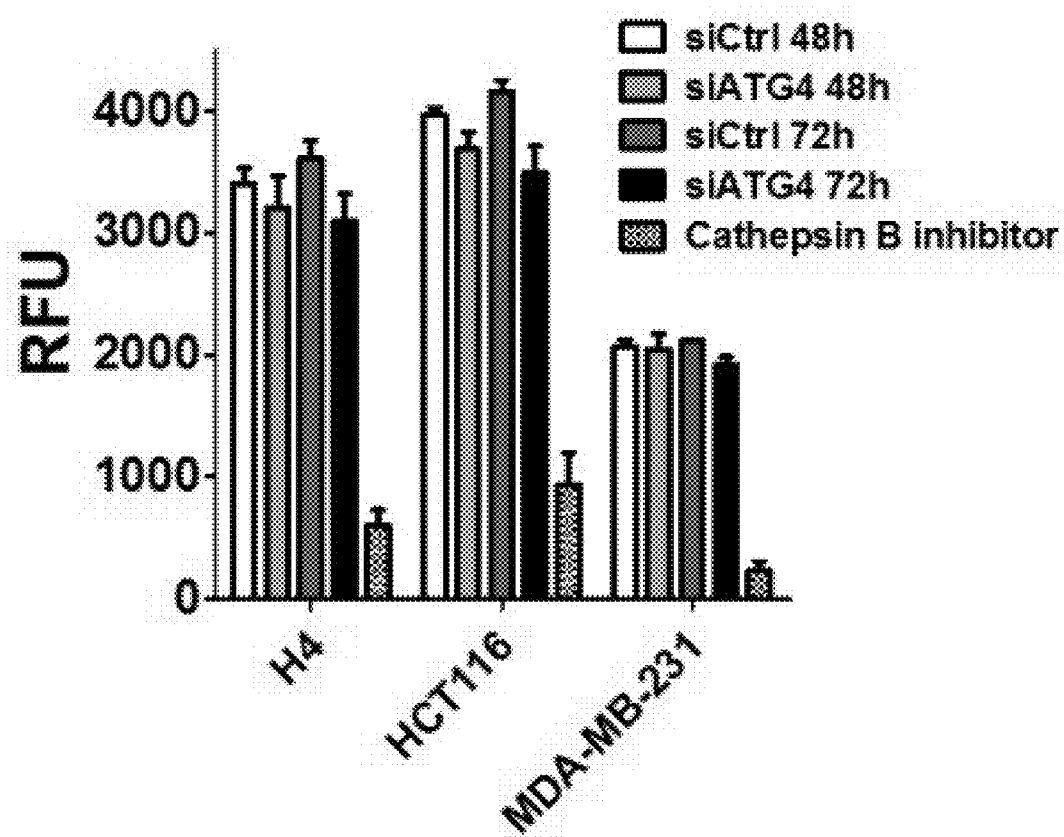
Figure 72:
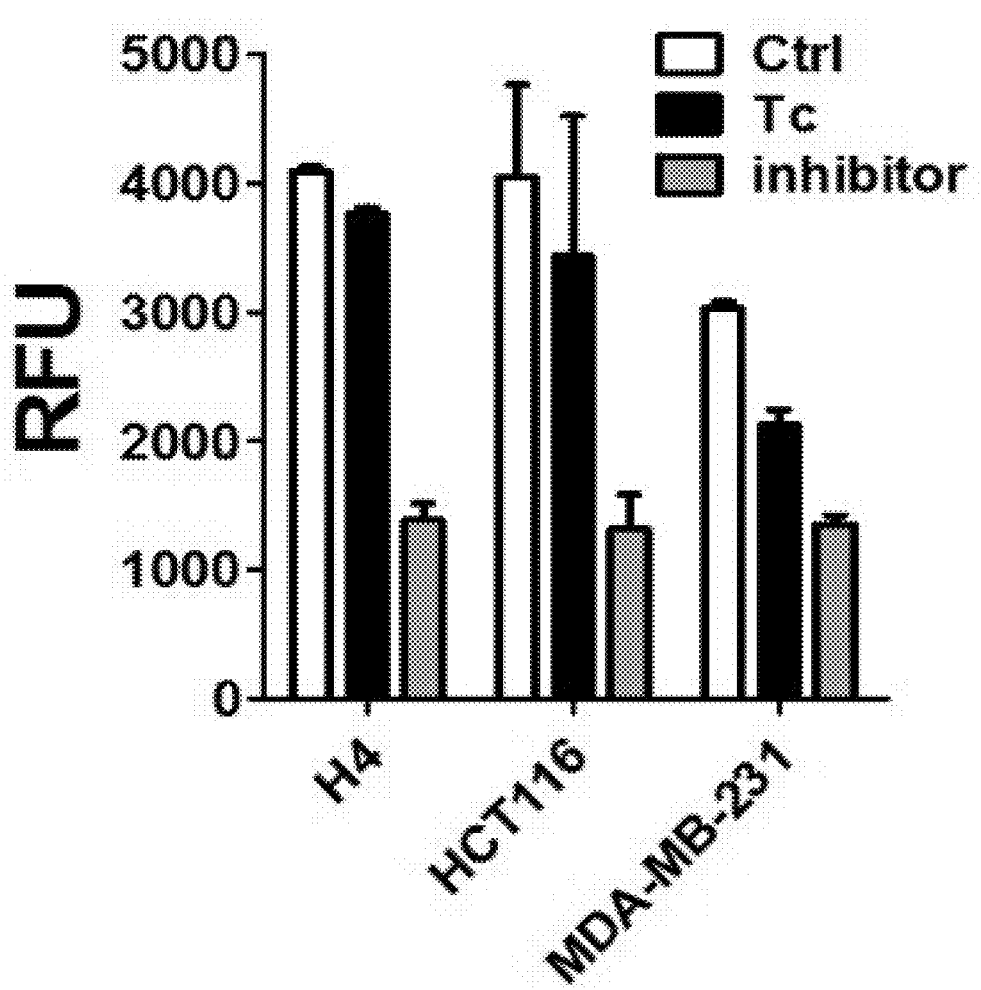
Figure 73:
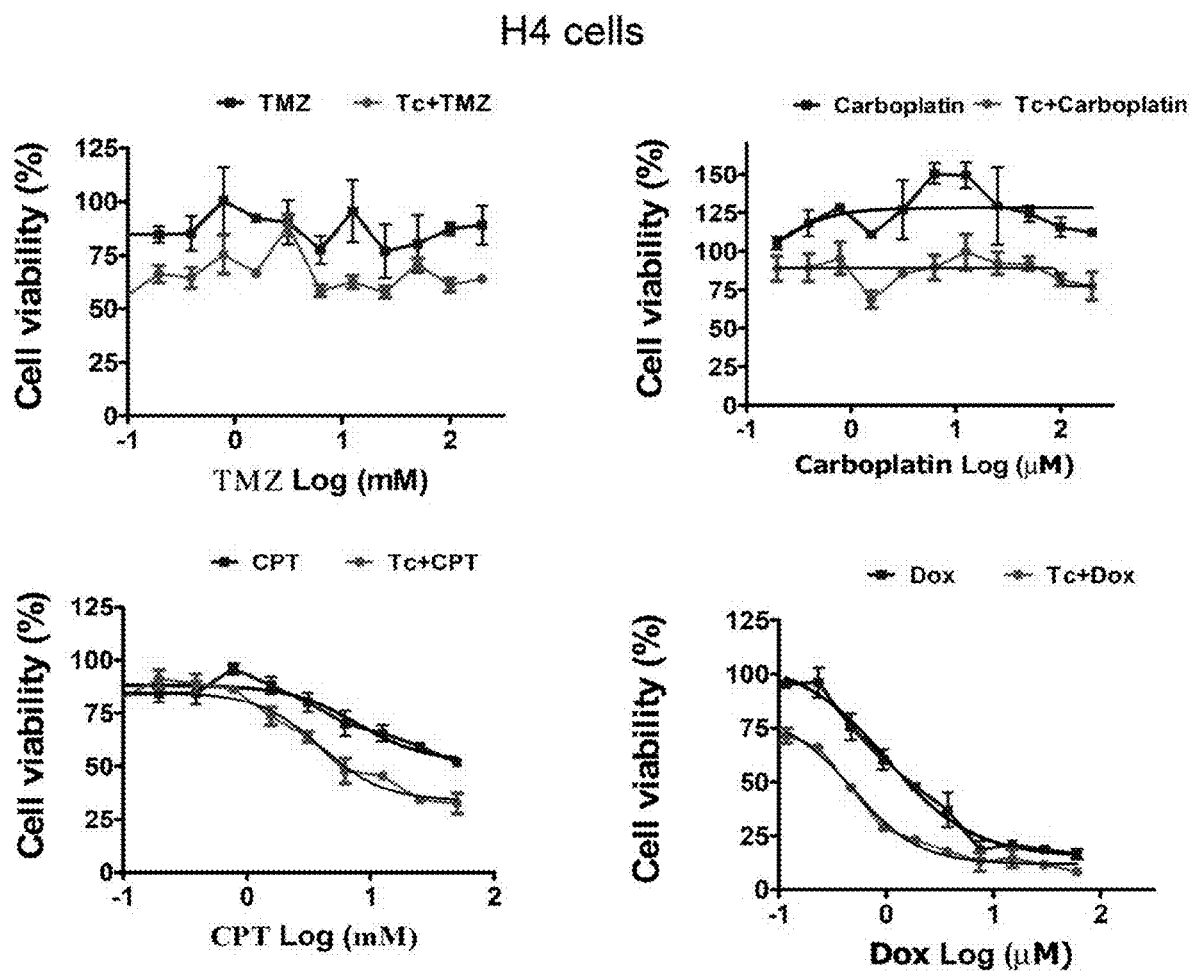
FIGS. 73-76 show that tioconazole sensitizes cancer cells to chemotherapeutic drugs.
Figure 74:
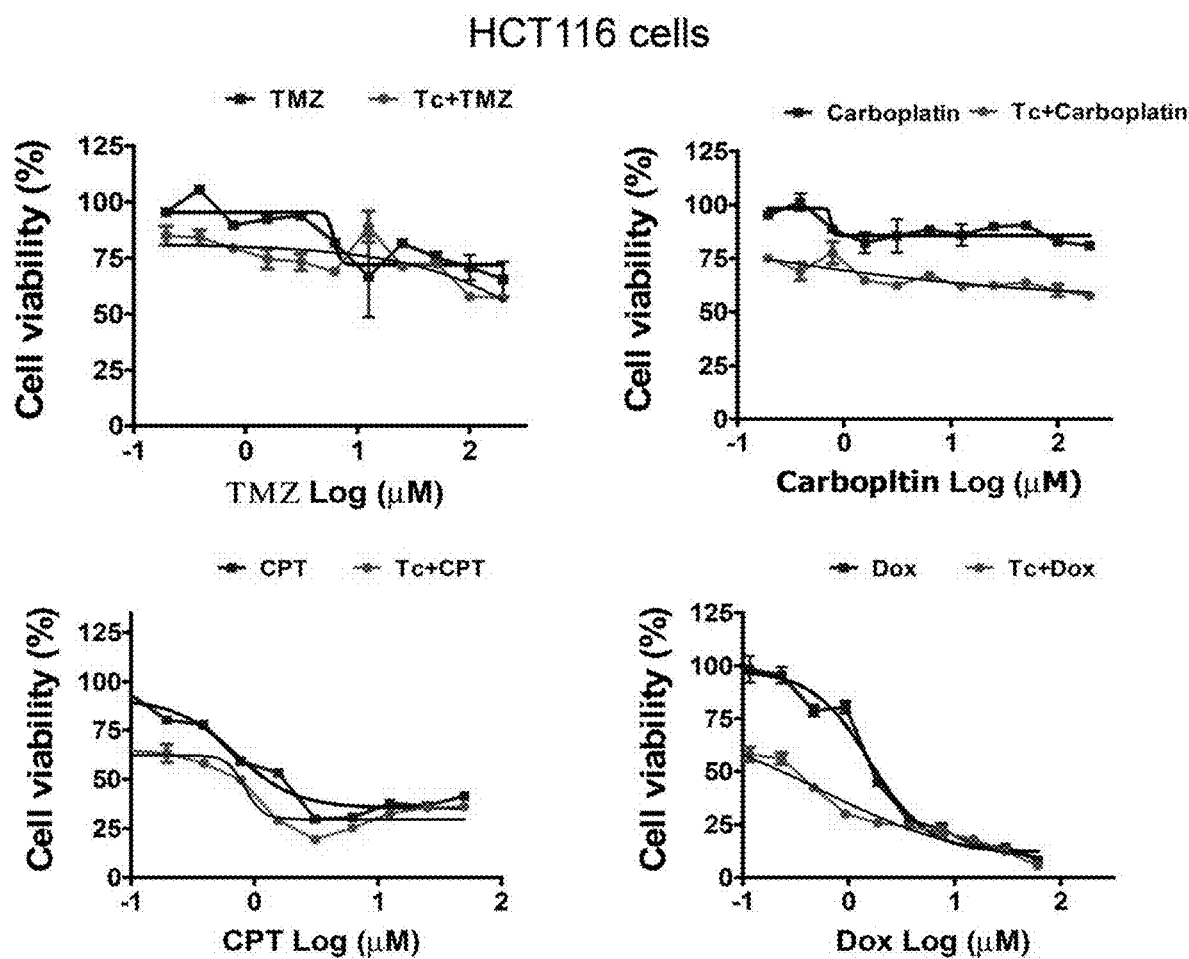
Figure 75:
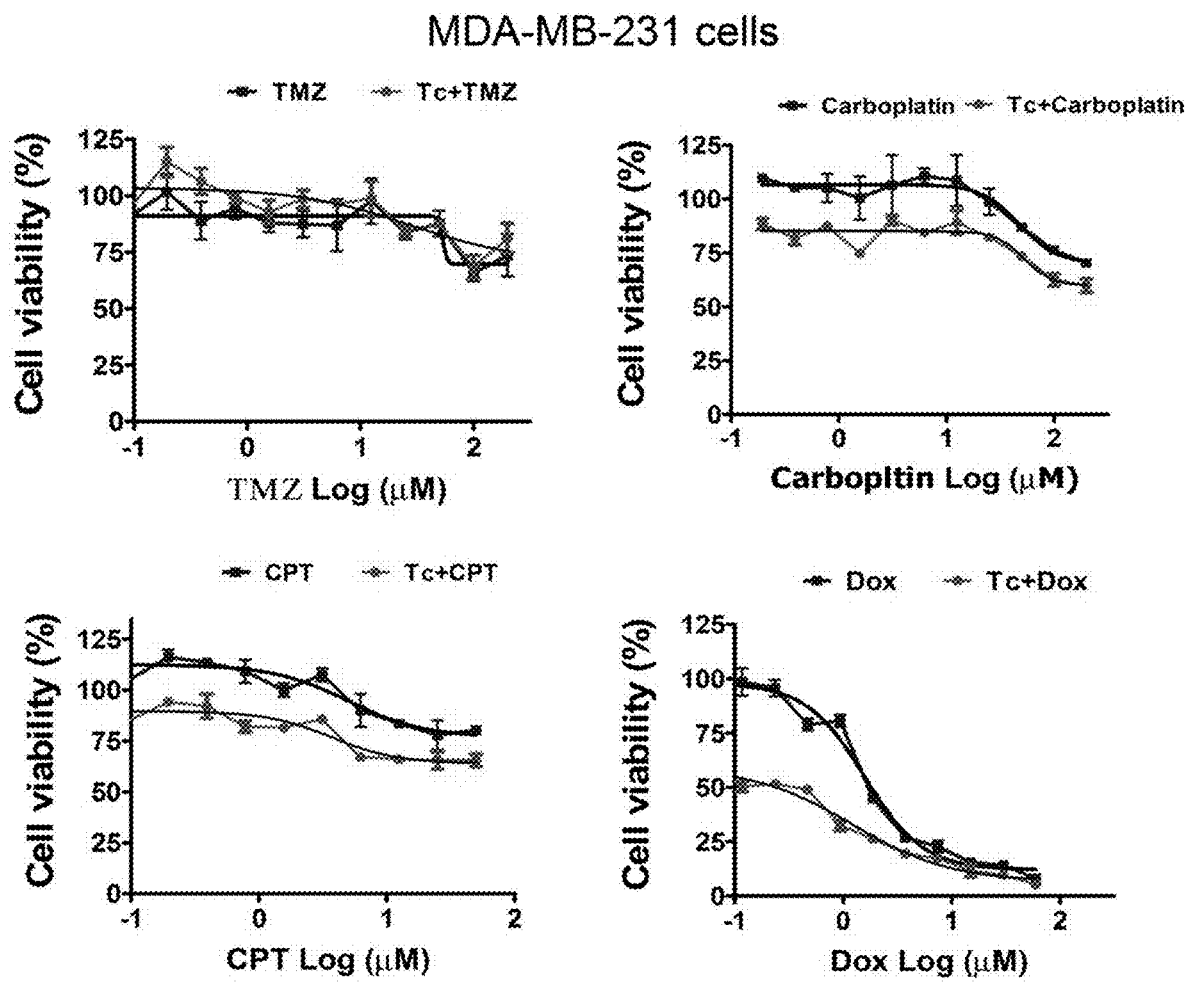
Figure 76:
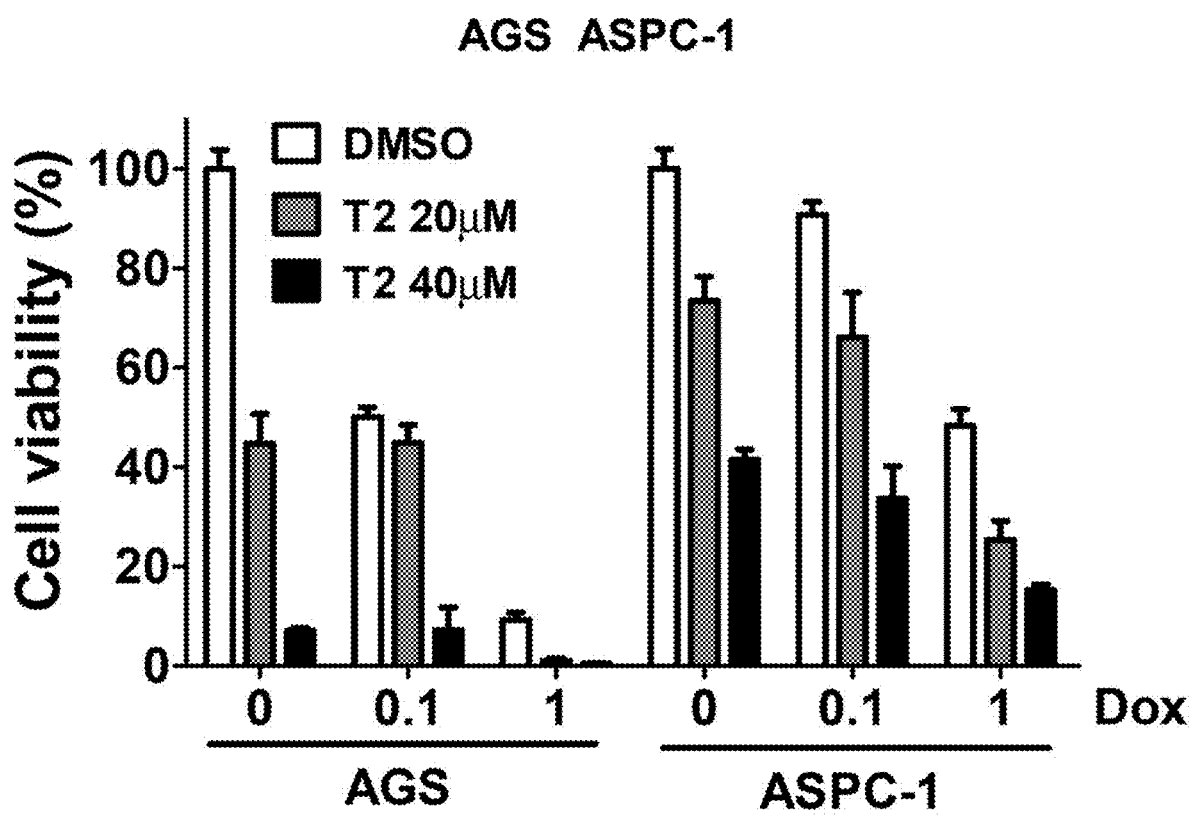

FIGS. 70-72 show the effects of silencing ATG4 and tioconazole on cathepsin b activity. (FIG. 70) H4, HCT116 and MDA-MB-231 cells were transfected with 5 nM non-targeting siRNA (Ctrl) or siRNA against ATG4 family members (ATG4) for 48 h. The knockdown efficiency of ATG4 was verified with real time PCR. (FIG. 71) $10^5$ of the ATG4 silenced cells were lysed to measure cathepsin B activity. Cathepsin B inhibitor is used a control. (FIG. 72) H4, HCT116 and MDA-MB-231 cells were treated with tioconazole (40 µM) for 6 h and equal amount cells were lysed to measure cathepsin B activity.

Tioconazole Sensitizes Cancer Cells to Chemotherapeutic Drugs.

FIGS. 73-76 show that tioconazole sensitizes cancer cells to chemotherapeutic drugs. (FIG. 73) H4, (FIG. 74) HCT116 or (FIG. 75) MDA-MB-231 cells were treated with the anticancer drug 2-fold serial titrated Temozolomide (TMZ), Carboplatin, Camptothecin (CPT) or Doxorubicin (Dox) for 24 h in the presence or absence of tioconazole (40 µM), and cell viability was measured with CellTiter-Glo. (FIG. 76) Gastric cancer AGS or pancreatic cancer ASPC-1 cells were treated with Dox (0.1 or 1 µM) in the presence or absence of Tc (20 or 40 µM) for 96 h. The cell viability was accessed with CellTiter-Glo.

Example 1: In Silico Drug-Repurposing Screening to Identify Tioconazole as an ATG4 Inhibitor Taking the open form of ATG4B structure as the drug target, we used the docking software Vina [20] and AMBER16 package with ff14SB force field to screen a library of 1312 FDA-approved drugs in silico. Vina provided at most 20 docking poses for each drug, which resulted in a total of 26,227 poses. To consider the important entropic effect [21], we clustered the poses in similar loci and binding orientations and prioritized drugs whose largest cluster contained more than 8 poses. Subsequently, we selected the poses that were sufficiently close to the active site (1613 poses of 242 unique drugs) and exhibited favorable Vina-defined binding energy to obtain 142 poses with the most favorable binding mode for each of the 142 unique drugs. The top-ranked 100 drugs with the best binding affinity were subjected to further body-temperature, explicit-solvent MD simulations for stability and binding free energy evaluations based on MM/GBSA [22], and the most favorable and purchasable 22 drugs were obtained for the subsequent biochemical and cellular assays to confirm their inhibitory efficacy (FIG. 1).

Figure 4:
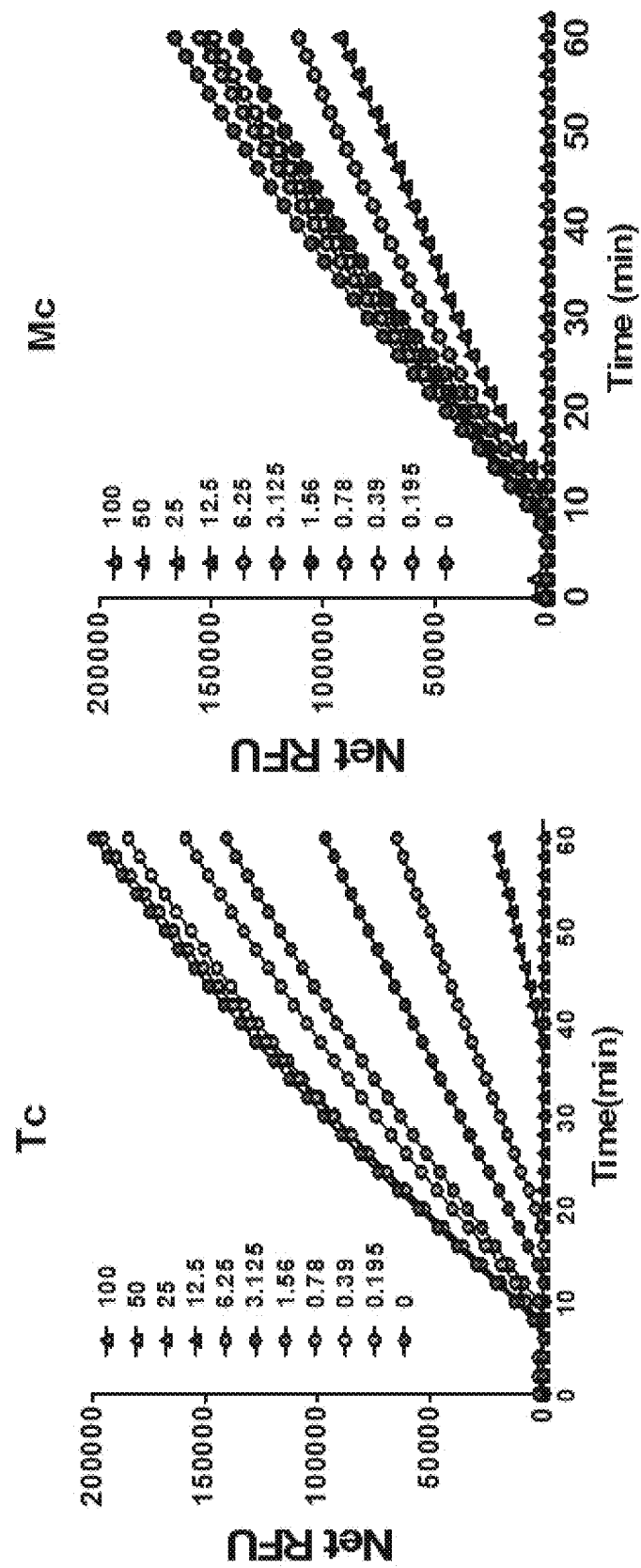

LC3-PLA2 and the LC3 cleavable transcription factor were used as ATG4 reporter substrates for biochemical and yeast cell-based assays, respectively, as previously reported [18, 23]. The yeast cell-based assay was initially improved with luminescent substrate and optimized for the robustness of the screening (FIG. 55-58). Four of the 22 drugs screened from the computational platform inhibited the activity of ATG4B by >70% (red points<30% in FIG. 2) in the biochemical reporter assays: Tolfenamic acid, Mefenamic acid, Tioconazole, and Entacapone. The rankings for these four drugs predicted by using only docking results were 30, 36, 82, and 60, which were notably improved to 14, 11, 48, and 1 after further examination by MD simulations and MM/GBSA calculations for binding stability. Tioconazole is the only one of these four compounds to also exhibit strong inhibition in the yeast cell-based assay (FIG. 2-10). To avoid interference due to antifungal effects in the yeast-based assay, a low dose of tioconazole was subjected to further validation using caspase-1 yeast cell-based assay and caspase-3 biochemical assay as counter screens (FIG. 3) (caspases belong to another class of cysteine proteases), and the results of these assays further suggested that tioconazole selectively inhibited ATG4B. A highly similar analog of tioconazole, miconazole, that originally ranked 83 based on MD simulations (MM/GBSA+ligand RMSF) was failed to exhibit as good inhibitory effect on ATG4B as tioconazole (FIG. 4). Entacapone, the highest-ranked drug based on computation, was as effective as tioconazole in the biochemical reporter assay but not cellular assay (FIG. 2), possibly due to its limited membrane permeability.

Figure 5:
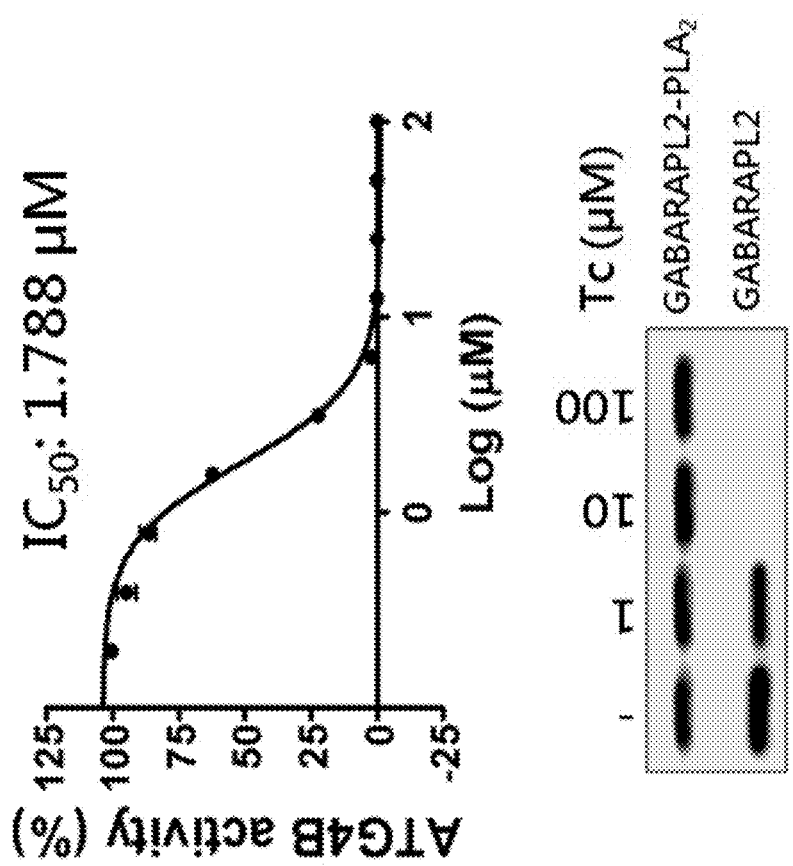
Figure 6:
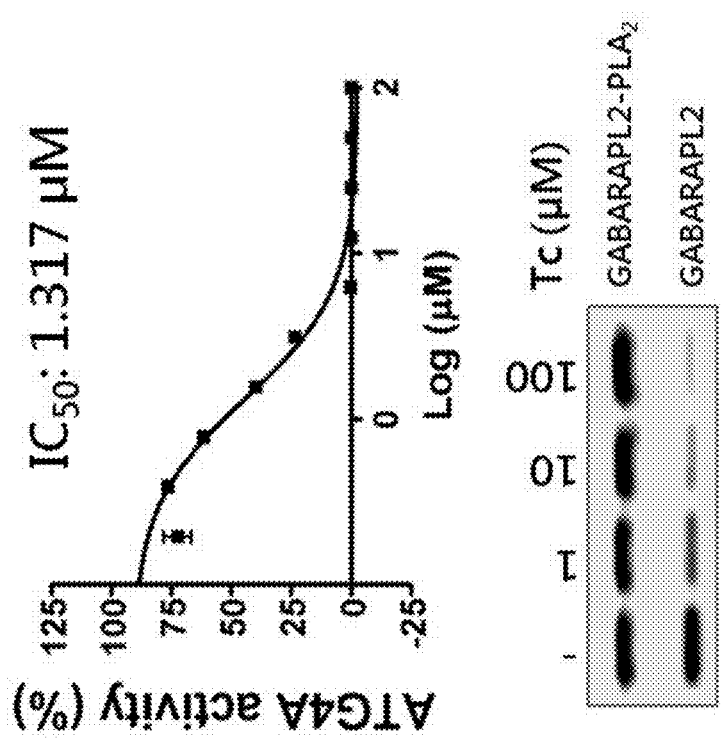

The ability of tioconazole to inhibit ATG4B and ATG4A proteolytic activity were assessed with a biochemical assay using GABARAL2-PLA2 as a common substrate reporter for both ATG4B and ATG4A (FIGS. 5 and 6). The half-maximal inhibitory concentrations (IC50) of tioconazole for ATG4B and ATG4A were 1.8±0.16 and 1.3±0.18 µM, respectively, which indicates that tioconazole is approximately 30-fold more potent than currently reported ATG4 inhibitors [24]. Moreover, immunoblotting results confirmed that tioconazole blocked the cleavage of GABA-RAL2-PLA2 by ATGA and ATG4B (FIGS. 5 and 6).

Figure 7:
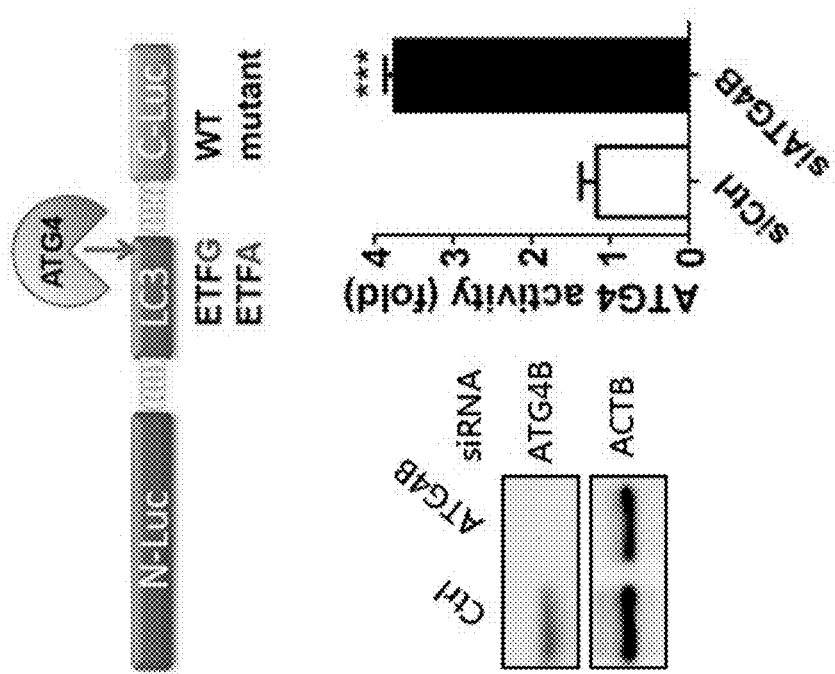
Figure 8:
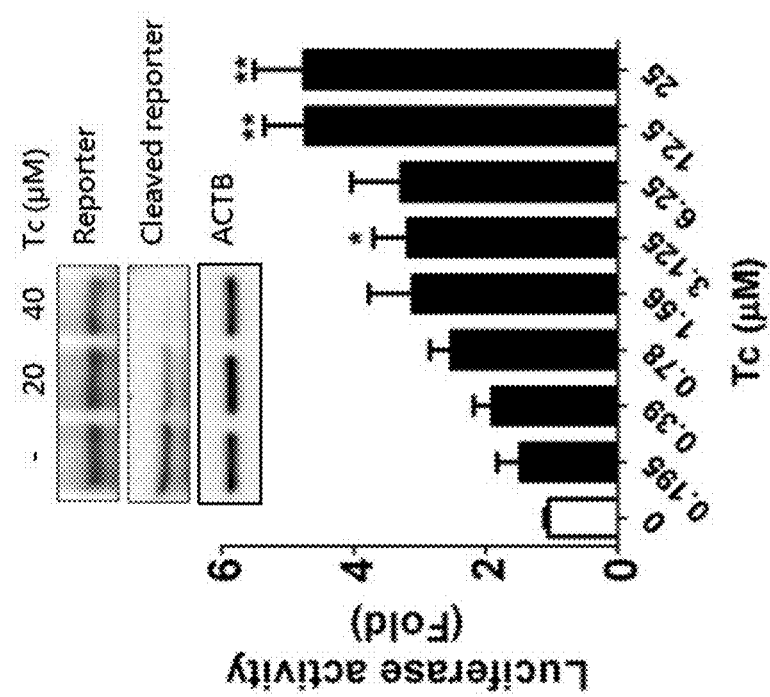
Figure 9:
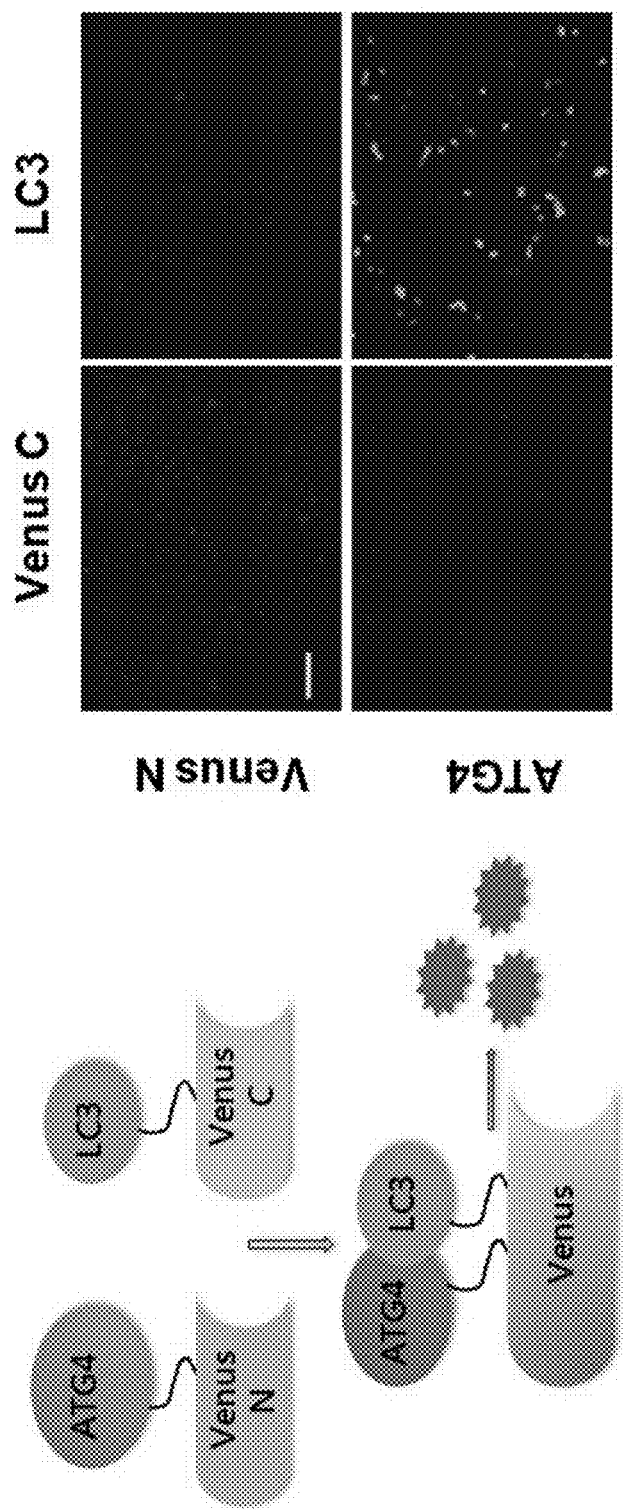

Next, the ability of tioconazole to inhibit ATG4 proteolysis in mammalian cells was examined using ATG4 cleavable luciferase assay (FIG. 7). Briefly, LC3 was constructed to split N-terminal and C-terminal luciferase in a mammalian expression vector, as indicated (FIG. 7). Silencing ATG4B and treatment with tioconazole increased the luciferase activity and attenuated the cleavage of chimera luciferase in the reporter cells (FIG. 8), which suggests that tioconazole might inhibit ATG4 in mammalian cells.

Figure 10:
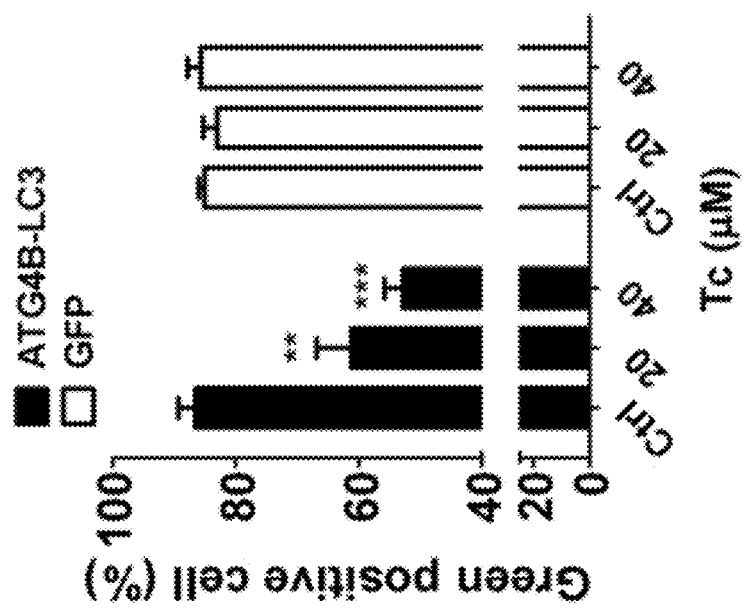

To further examine the effects of tioconazole on the binding of ATG4 to LC3, the Venus N-terminal-ATG4B and Venus C-terminal-LC3 chimera expression vectors were transfected into HEK293T cells (FIG. 9), and the interaction between ATG4B and LC3 in the presence or absence of tioconazole was assessed using flow cytometry (FIG. 10). The bimolecular fluorescence complementation (BiFC) results indicated that tioconazole reduced the fluorescence emitted from the formation of the ATG4B and LC3 complex and did not affect GFP fluorescence (FIG. 10), which suggests that tioconazole interfered with the binding between ATG4 and LC3 in living cells.

Example 2: Docking and MD Simulation Further Support that the Direct Blockage of the ATG4B Active Site is the Primary Inhibitory Effect of Tioconazole To investigate the molecular origin of the tioconazole-mediated inhibition of ATG4 proteolysis, we conducted further docking experiments for both the open (active, FIG. 11, PDB code 2Z0D) and closed (inactive, FIG. 12, PDB code 2CY7) forms of ATG4B using Autodock 4.0 [25]; the results are shown in FIG. 11-16. Tioconazole, which consists of 3-, 5- and 6-membered rings, namely, dichlorophenyl, chlorothiophenyl and imidazole rings (PubChem CID: 5482), has been shown to preferably dock at the active site of the open form of ATG4B (ATG4B (O), FIG. 13). Similar results were obtained for the modeled open form of ATG4A (FIG. 59), which confirms the previously demonstrated specificity. We also found that tioconazole was able to interact with Asp278, a key catalytic residue, even in the closed form of ATG4B (FIGS. 14 and 59), when most of the active site is shielded by the enzyme's N-terminus. This finding is consistent with the previously reported ability of several lead compounds to interact with part of the active site, even in the closed state of ATG4B [24]. However, most interactions were predicted to occur in a canyon flanked by the N-terminus and the main body of ATG4B toward the root of the N-terminus (FIG. 14). The top-ranked docking poses (Tables 1) and the contact frequency of a ligand with each residue (FIG. 59) are summarized in SI. Interestingly, we also identified highly scored docking poses in a cluster that occupies the binding site for ATG4B's N-terminus in LC3 (FIG. 15). LC3's seizure of ATG4B's N-terminus helps maintain the enzyme in an open form and consequently active state. Hence, moderately populated tioconazole in the N-term binding site of LC3 could possibly impair the stabilization of an active enzyme by the substrate and consequently reduce its proteolytic activity.

The stability of several highly ranked docking poses (in terms of the binding free energy and the size of the cluster) in ATG4B(O) was subsequently assessed using MD simulations. The highest scored poses (ranks 1, 2, 3 and 6) suggested that tioconazole blocked the entry of the C-terminus of LC3 into the catalytic pocket and most frequently contacted the catalytic Cys74 and Trp142 residues via its dichlorophenyl or chlorothiophenyl rings (FIG. 16). MD simulations demonstrated that the ligands of ranks 1 and 2 remained with the enzyme at the active site throughout the entire 100 ns simulation, whereas the ligands of ranks 3 and 6 left the enzyme at 23.3 and 10.5 ns, respectively. Interestingly, the imidazole ring of tioconazole in rank 1 swung to the opposite side of the active site at 2.8 ns and subsequently mimicked the rank 2 pose. Conversely, ligands in the rank 1 pose in the "closed" ATG4B and that in LC3's N-terminal binding site left the binding site after 8.5 ns and 13.0 ns, respectively, suggesting that binding was only transient. Based on these findings, we conclude that tioconazole primarily inhibits proteolytic function by directly blocking the active site in the open form of ATG4B.

TABLES 1

Top ten ranked clusters of docking poses for the 'open' ATG4B (ATG4B (O)).

| Cluster rank Energy | Lowest Binding ΔG (kcal/mol) | Mean binding energy ΔG (kcal/mol) in the cluster | Number of conformations | Region |
|---|---|---|---|---|
| 1 | −9.69 | −9.15 | 11 | 1 |
| 2 | −9.11 | −8.52 | 8 | 1 |
| 3 | −9.06 | −8.54 | 9 | 1 |
| 4 | −8.81 | −8.70 | 3 | 1 |
| 5 | −8.73 | −8.73 | 1 | 1 |
| 6 | −8.43 | −8.22 | 11 | 1 |
| 7 | −8.31 | −7.69 | 5 | 2 |
| 8 | −8.21 | −8.03 | 2 | 1 |
| 9 | −8.13 | −8.13 | 1 | 1 |
| 10 | −8.01 | −8.01 | 1 | 1 |

Top ten ranked clusters of docking poses for the 'closed' ATG4B (ATG4B (C)).

| Cluster rank Energy | Lowest Binding ΔG (kcal/mol) | Mean binding energy ΔG (kcal/mol) in the cluster | Number of conformations | Region |
|---|---|---|---|---|
| 1 | −8.15 | −7.75 | 23 | 1 |
| 2 | −7.75 | −7.35 | 9 | 1 |
| 3 | −7.67 | −7.46 | 3 | 1 |
| 4 | −7.47 | −7.43 | 2 | 1 |
| 5 | −7.45 | −7.24 | 2 | 1 |
| 6 | −7.41 | −6.98 | 4 | 2 |
| 7 | −7.31 | −7.27 | 2 | 1 |
| 8 | −7.26 | −7.26 | 1 | 3 |
| 9 | −7.25 | −7.25 | 1 | 3 |
| 10 | −7.23 | −7.19 | 2 | 1 |

Top ten ranked clusters of docking poses for LC3.

| Cluster rank Energy | Lowest Binding ΔG (kcal/mol) | Mean binding energy ΔG (kcal/mol) in the cluster | Number of conformations | Region |
|---|---|---|---|---|
| 1 | −7.52 | −7.16 | 3 | 1 |
| 2 | −7.44 | −7.21 | 3 | 1 |
| 3 | −7.28 | −6.89 | 11 | 2 |
| 4 | −7.04 | −6.98 | 3 | 1 |
| 5 | −6.95 | −6.69 | 30 | 3 |
| 6 | −6.88 | −6.54 | 4 | 3 |
| 7 | −6.81 | −6.47 | 3 | 1 |
| 8 | −6.70 | −6.70 | 1 | 2 |
| 9 | −6.64 | −6.64 | 1 | 1 |
| 10 | −6.59 | −6.48 | 6 | 2 |

Top ten ranked clusters of docking poses for the open/active form of ATG4A.

| Cluster rank Energy | Lowest Binding ΔG (kcal/mol) | Mean binding energy ΔG (kcal/mol) in the cluster | Number of conformations | Region |
|---|---|---|---|---|
| 1 | −9.70 | −9.17 | 15 | 1 |
| 2 | −9.10 | −8.60 | 3 | 1 |
| 3 | −9.01 | −8.60 | 8 | 1 |
| 4 | −8.96 | −8.63 | 27 | 1 |
| 5 | −8.69 | −8.66 | 3 | 1 |
| 6 | −8.47 | −8.17 | 8 | 1 |
| 7 | −8.34 | −8.08 | 5 | 1 |
| 8 | −8.23 | −8.23 | 1 | 1 |
| 9 | −8.13 | −8.13 | 1 | 1 |
| 10 | −8.11 | −8.11 | 1 | 1 |

Clusters are ranked by the lowest binding energy ΔG (kcal/mol) in each cluster. The mean binding energy ΔG (kcal/mol) is calculated by averaging the binding energy of all poses in a cluster. The spatial "regions" that indicate the locations of the individual clusters are labeled in FIGS. 13, 14, 15, 60, and 61.

Figure 17:
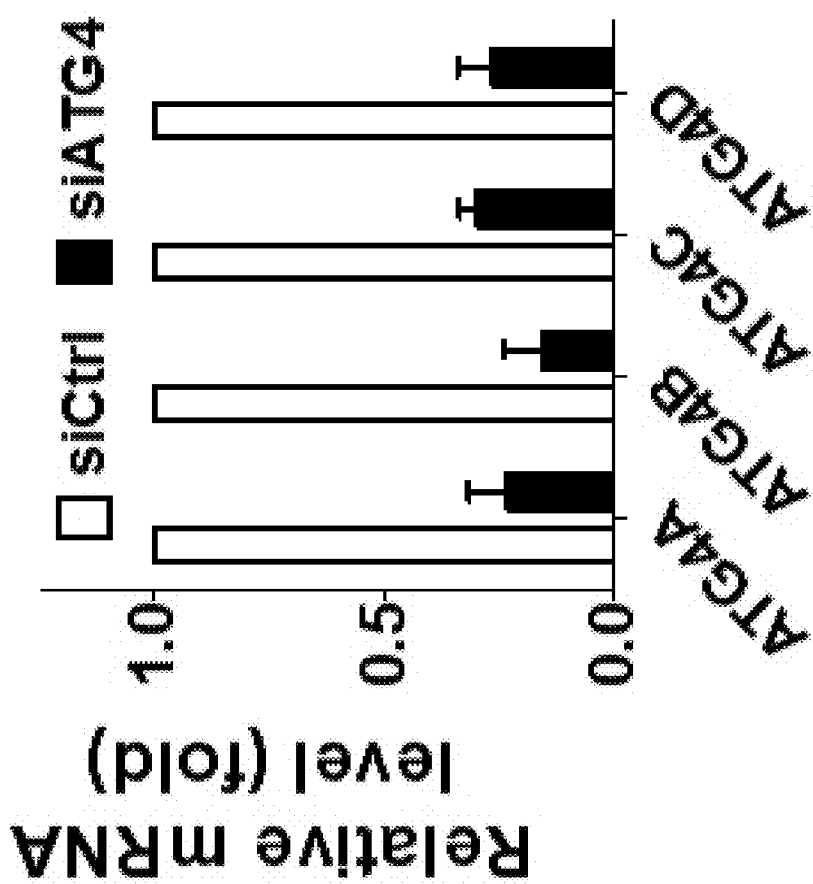
FIGS. 17-26 show the effects of tioconazole on autophagic activity in cancer cells.
Figure 18:
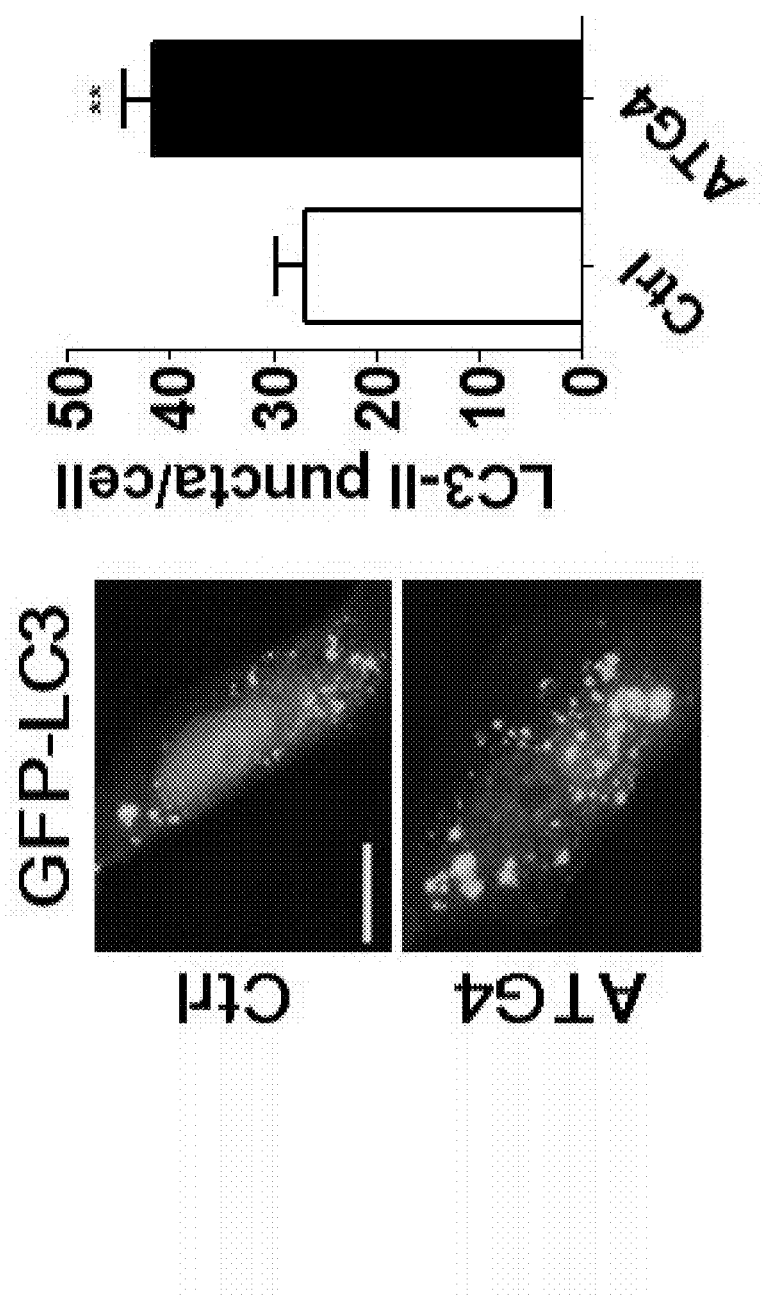
Figure 19:
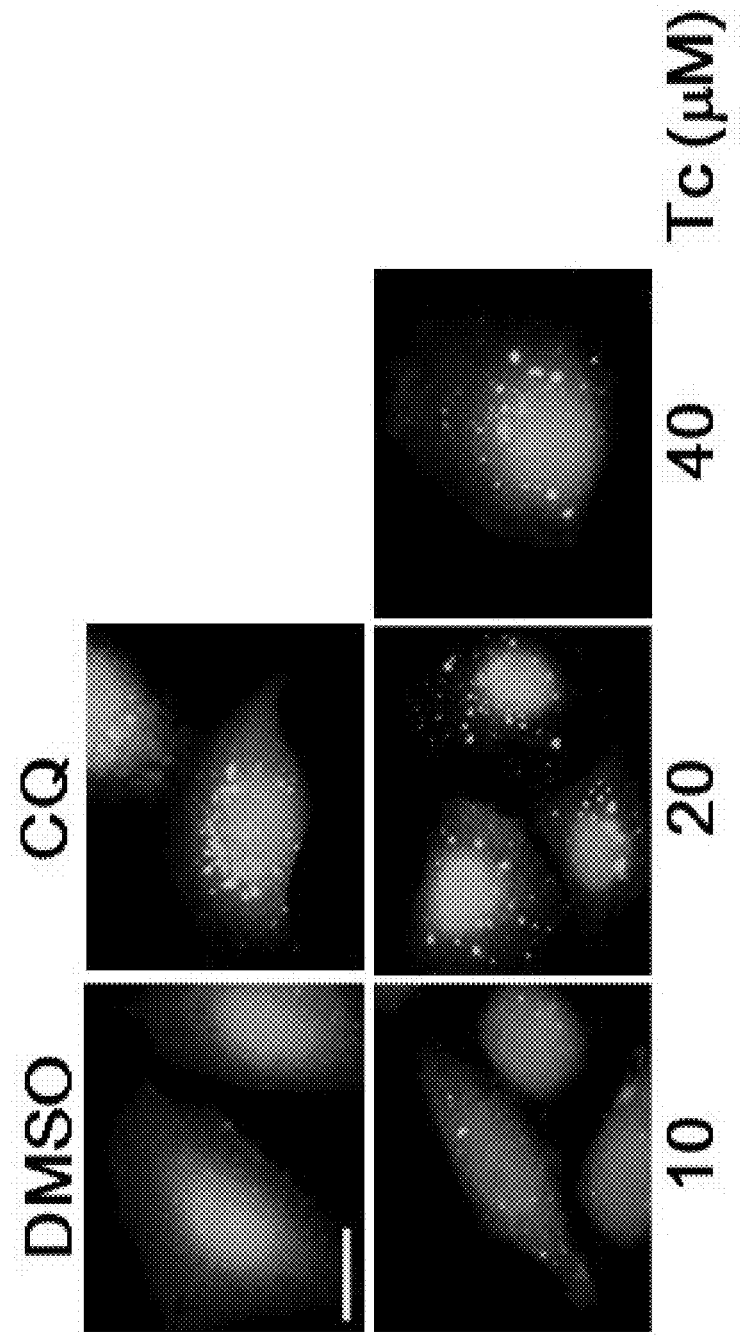
Figure 20:
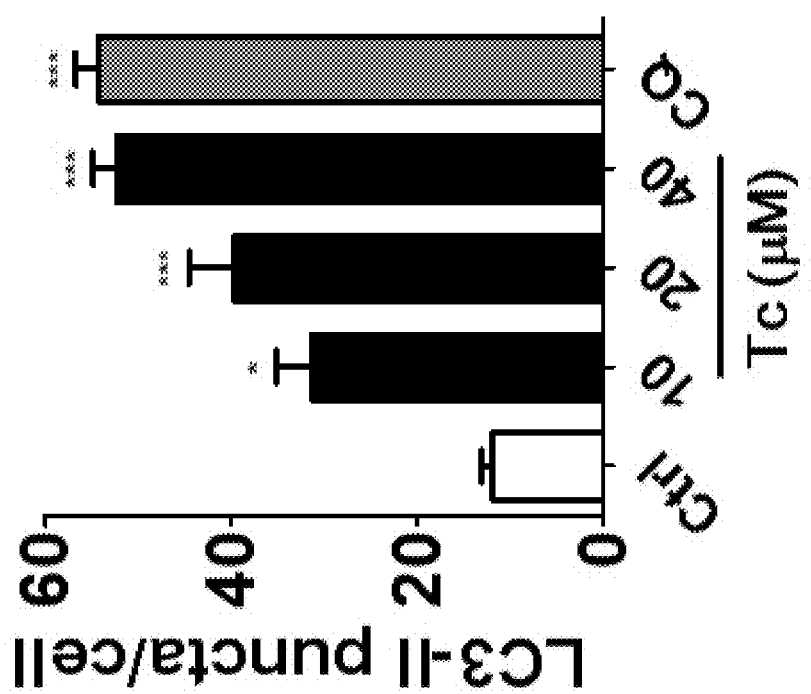
Figure 21:
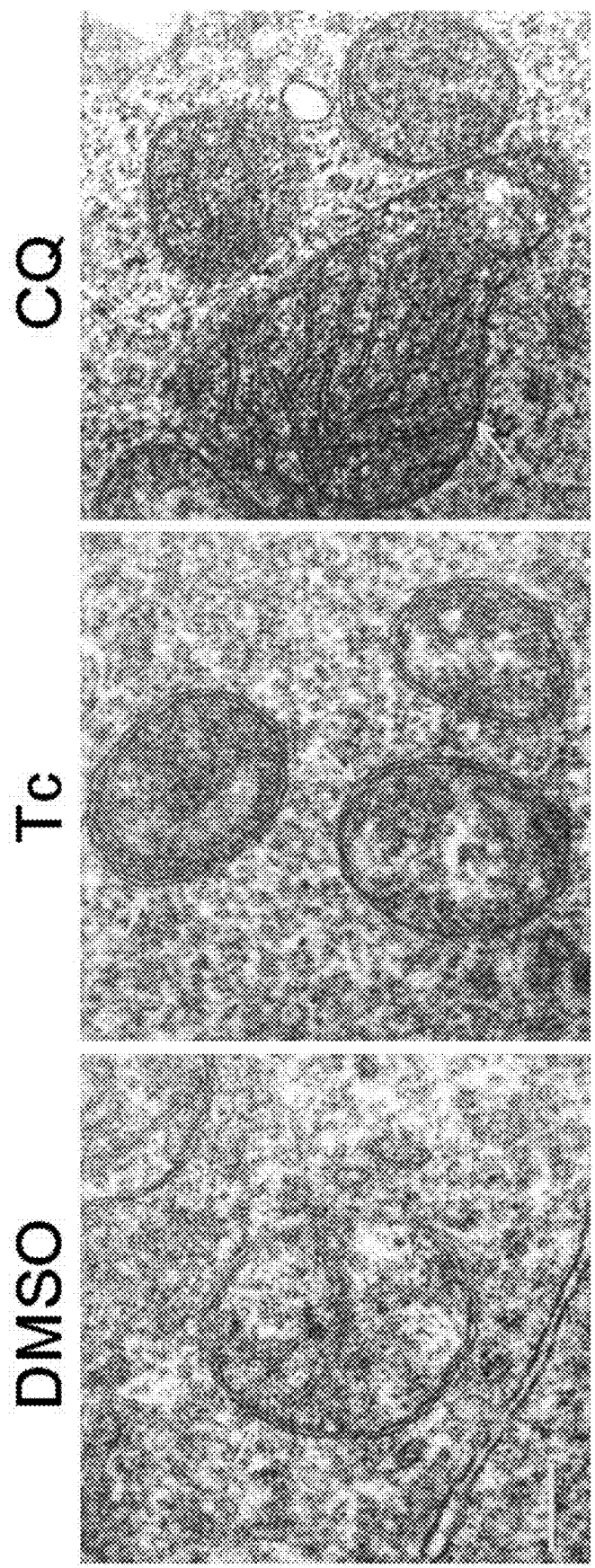
Figure 22:
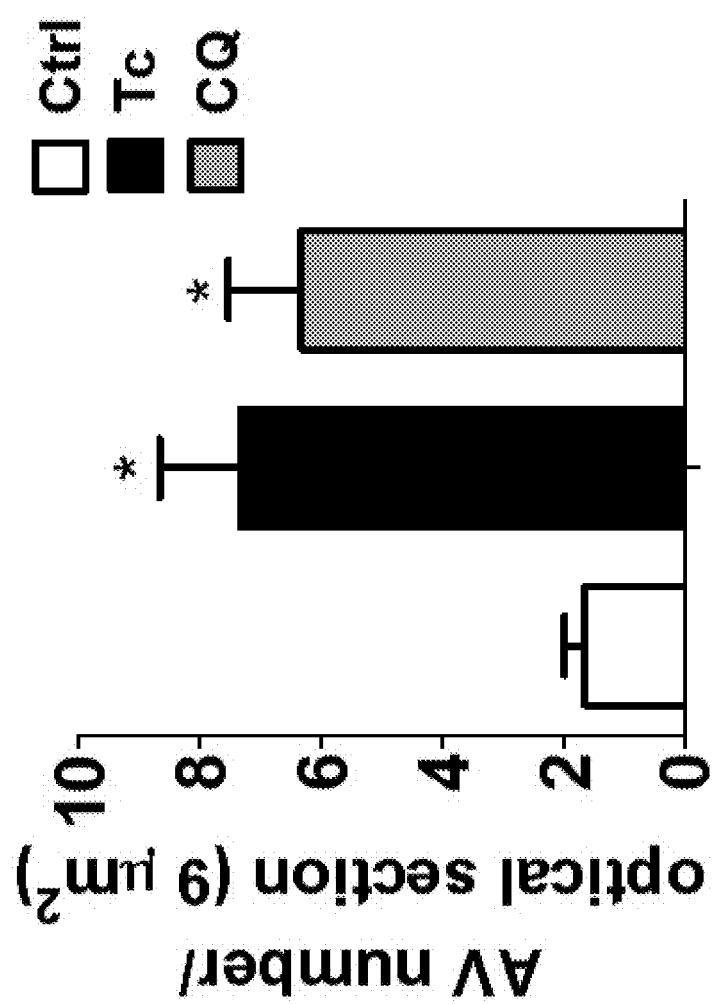

Example 3: Tioconazole Accumulates Autophagosomes and Diminishes Autophagic Flux in Cancer Cells Inhibiting ATG4 may increase or decrease LC3 association with the autophagosome because ATG4 plays a dual role: it first mediates conjugation of LC3 to lipids and subsequently deconjugates LC3-II by acting as a hydrolase to remove the lipids [26, 27]. We found that the siRNA-mediated silencing of ATG4 family members or treatment with tioconazole resulted in the accumulation of GFP-LC3-II puncta (FIGS. 17 and 18). Similarly, transmission electron microscopy results showed that the number of autophagosomes was increased in the tioconazole-treated cells, whereas very few autophagosomes were observed in untreated cells (FIGS. 21 and 22).

Figure 23:
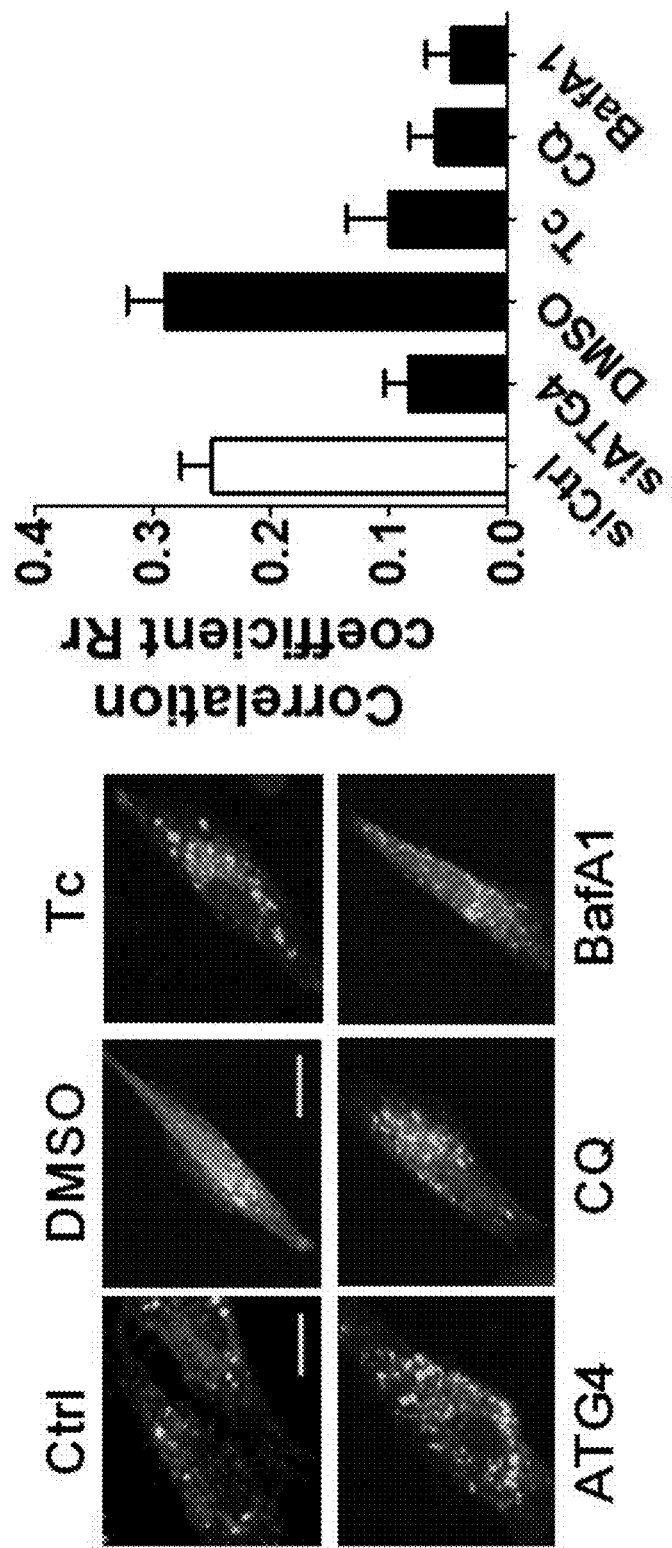
Figure 24:
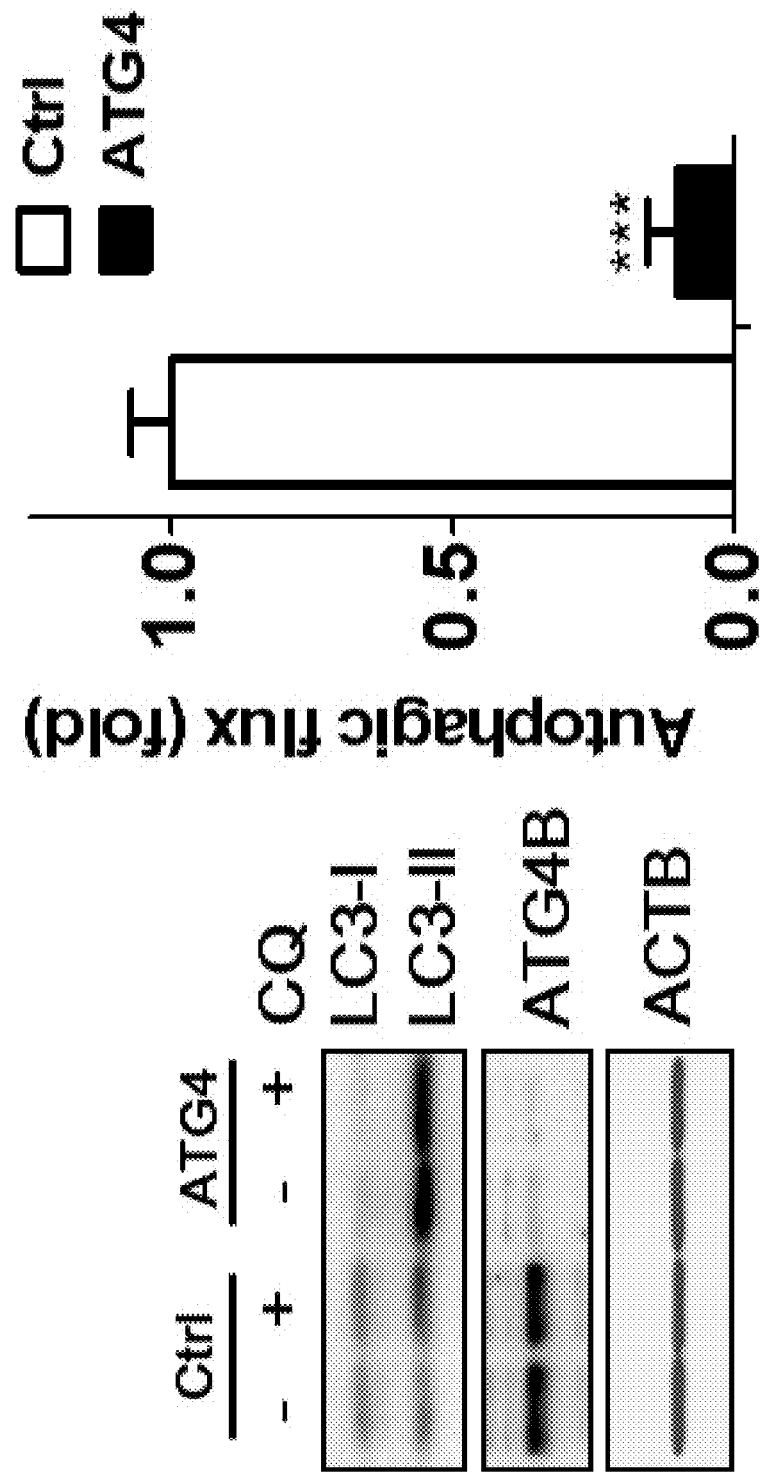
Figure 25:
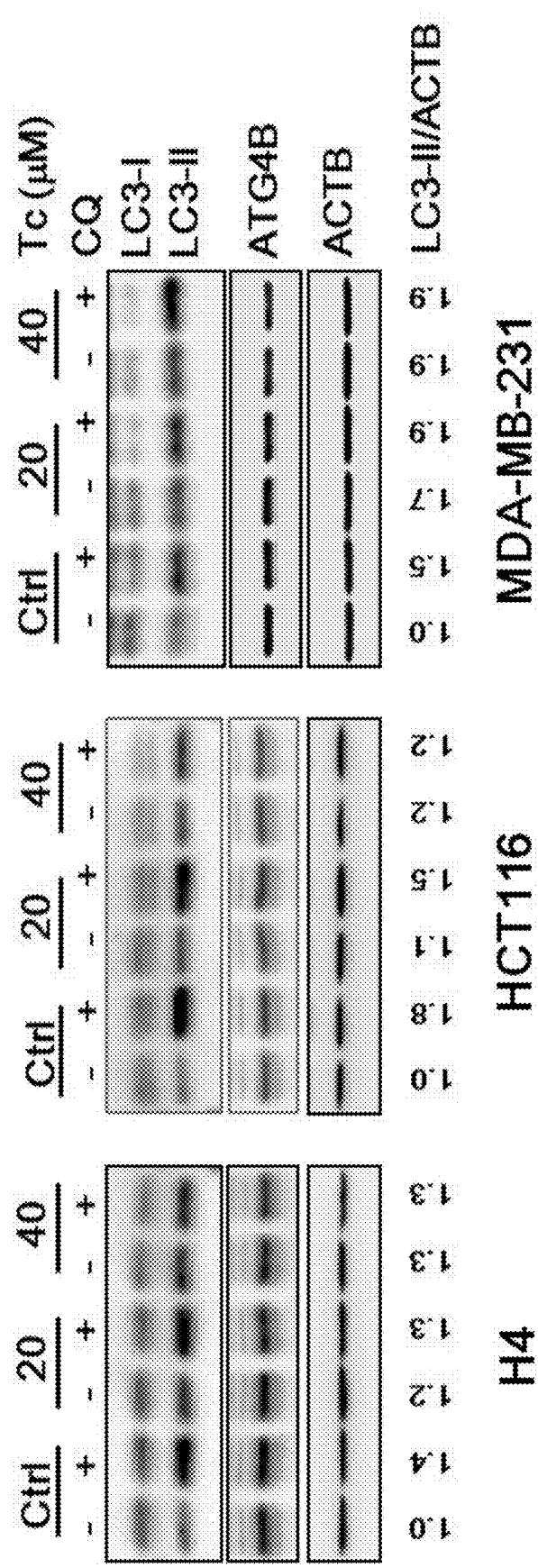
Figure 26:
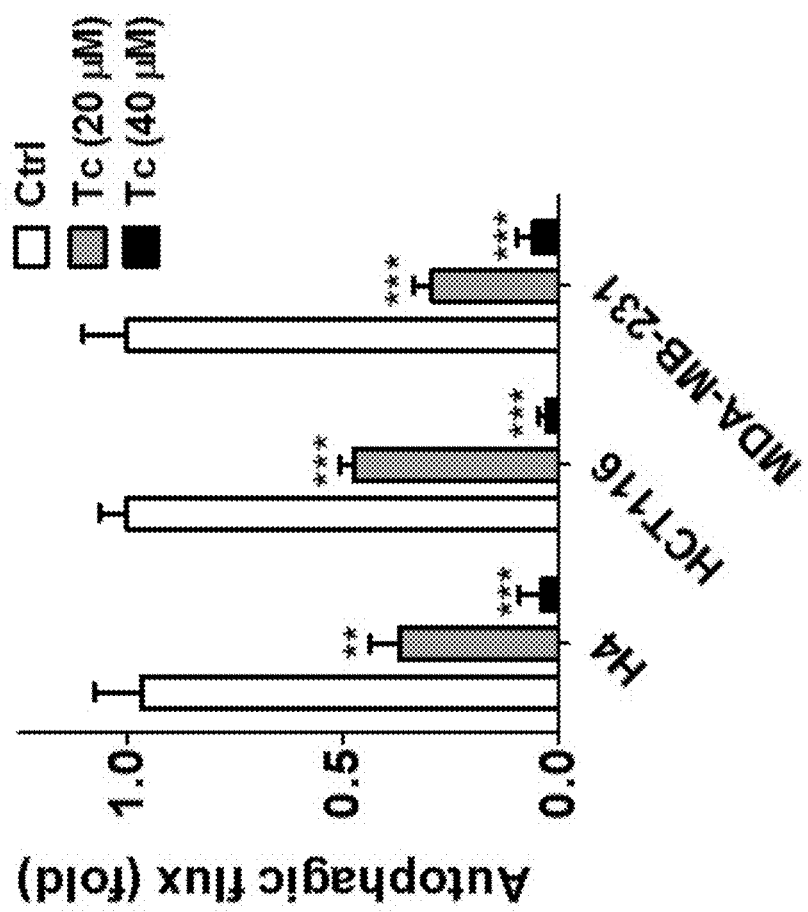
Figure 27:
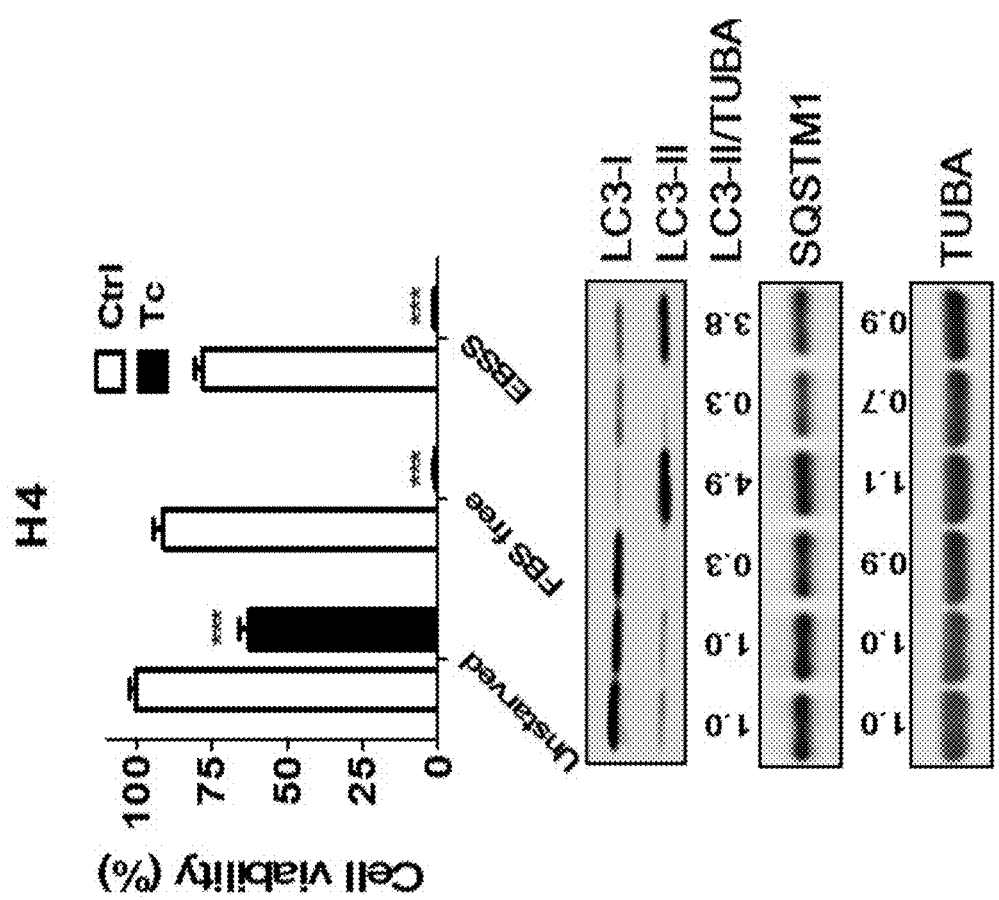
FIGS. 27-36 show that tioconazole sensitizes cancer cells to starvation and chemotherapeutic drugs.
Figure 28:
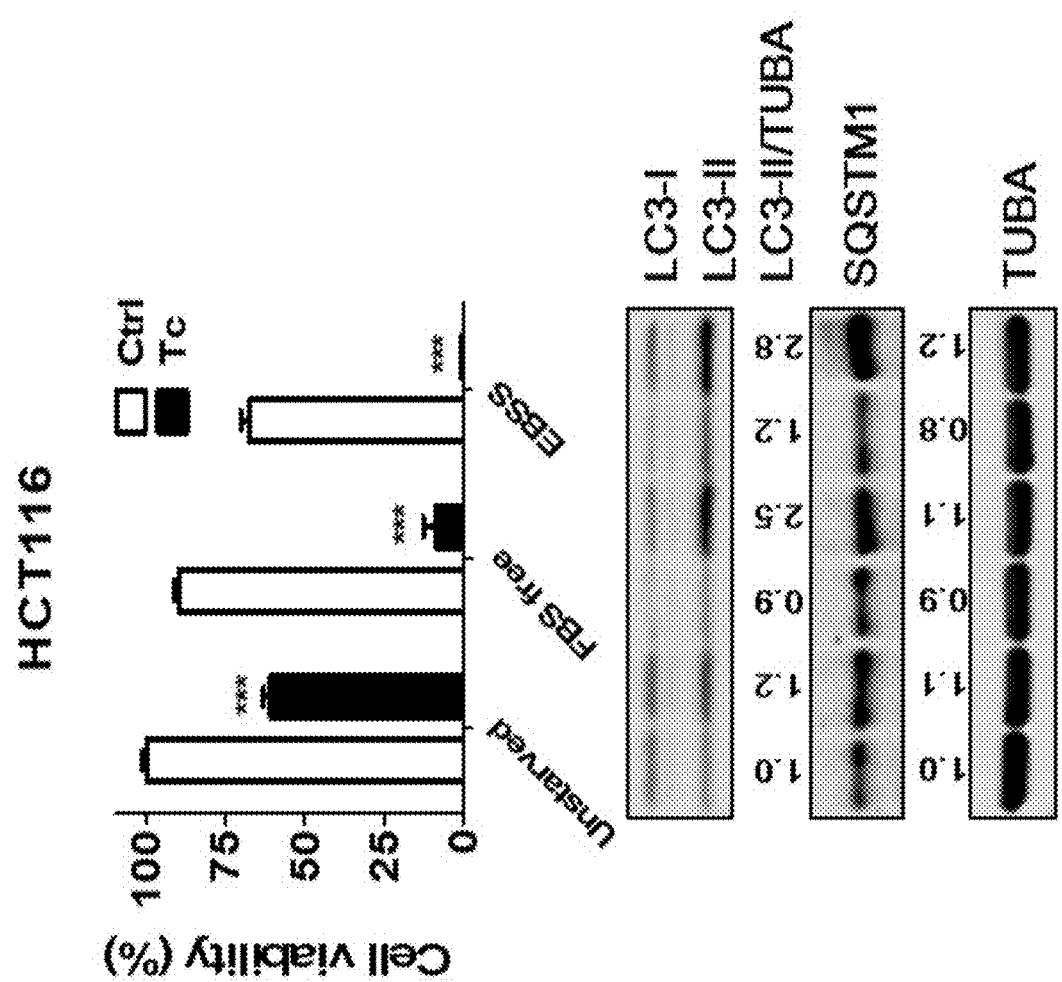
Figure 29:
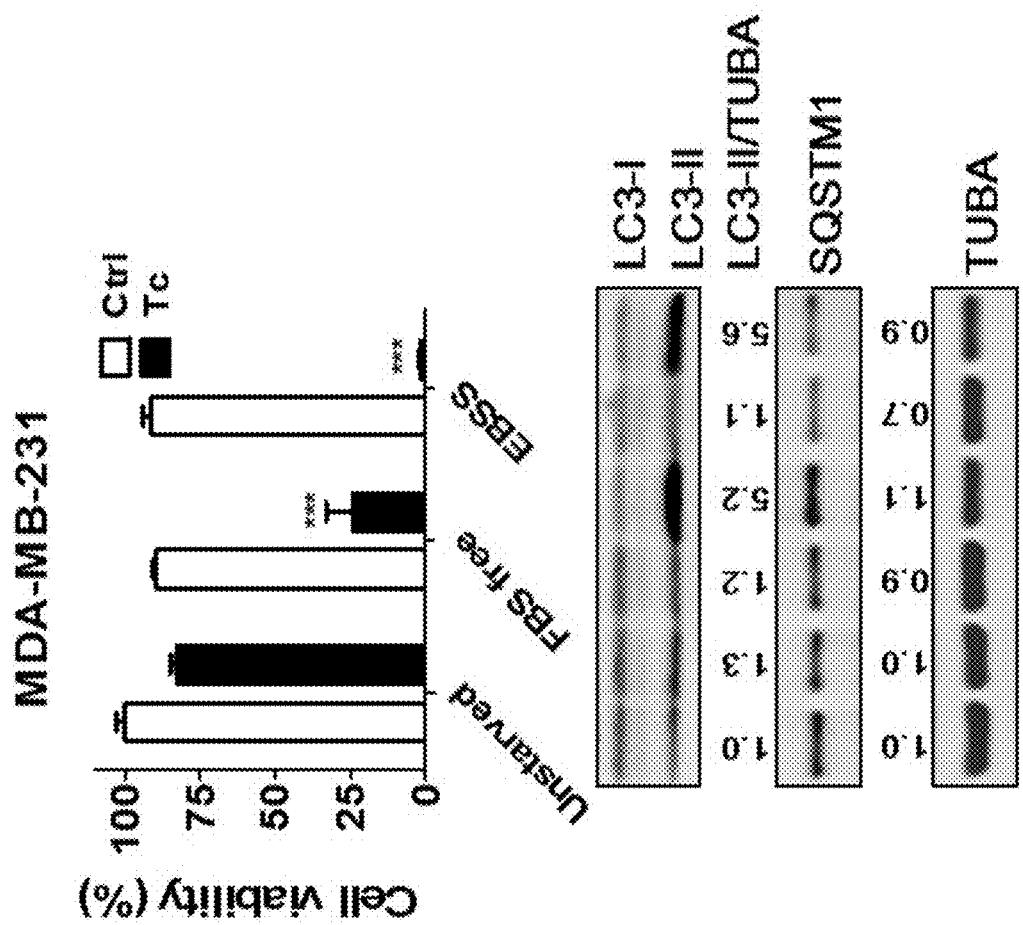
Figure 30:
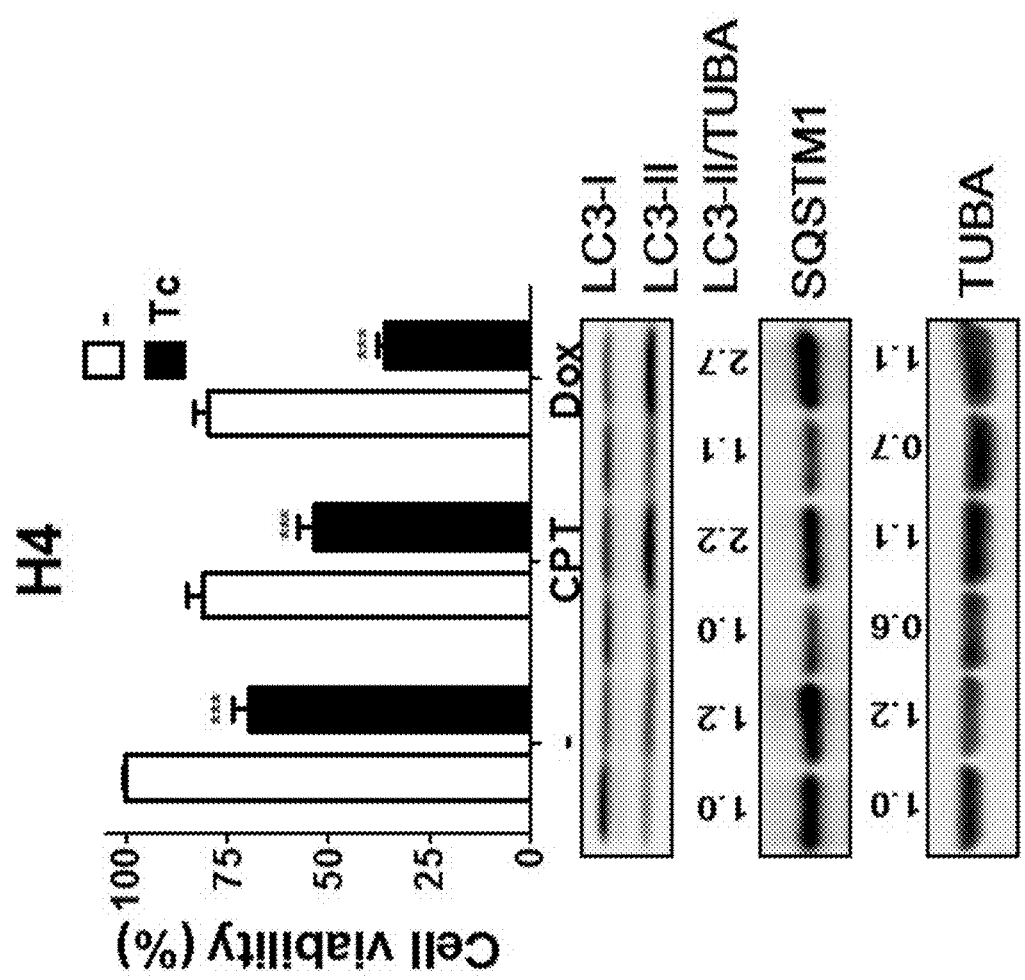
Figure 31:
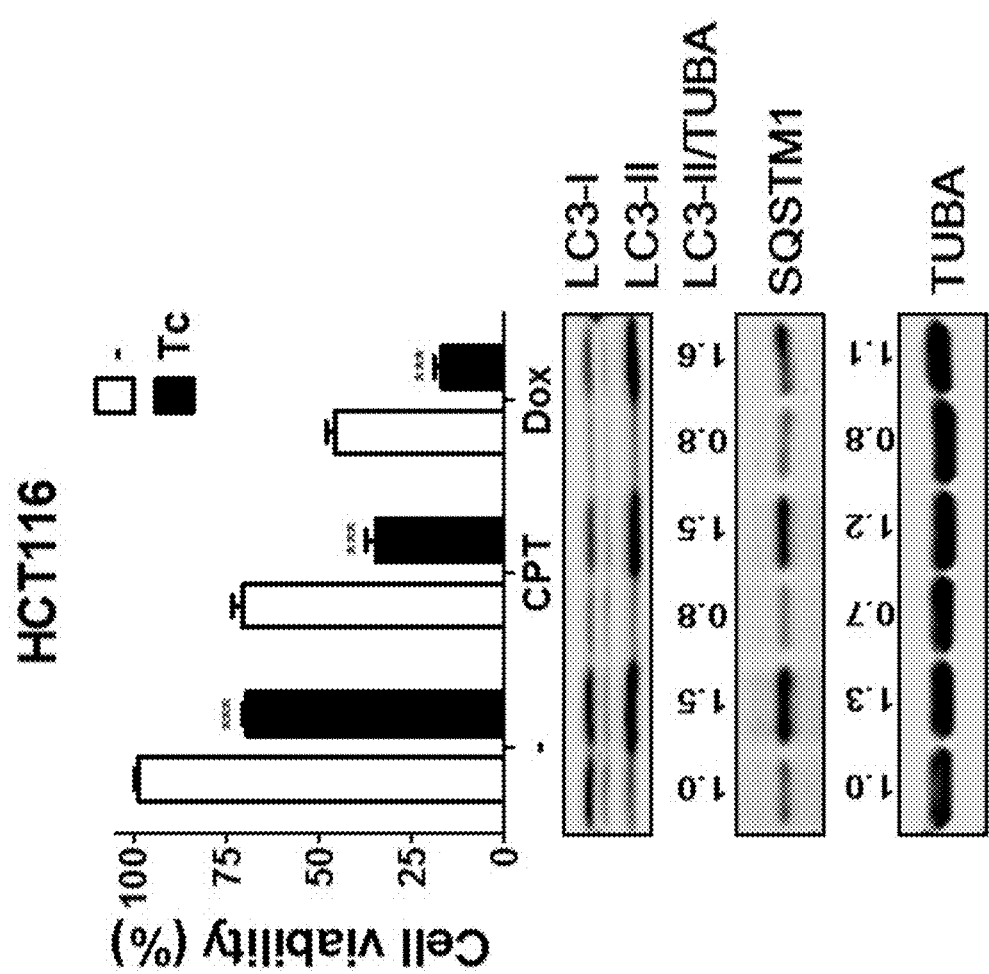
Figure 32:
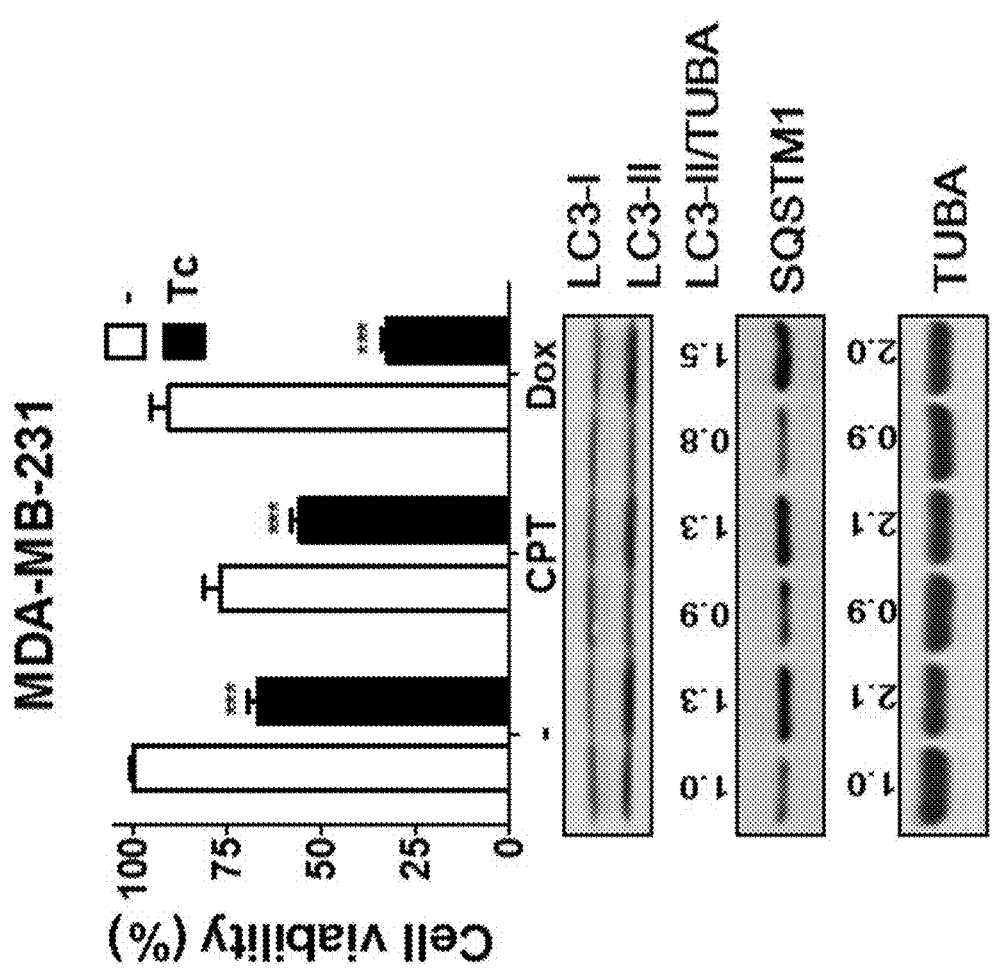

Moreover, ATG4 deconjugates LC3-II from the autophagosome to facilitate autophagosome maturation for fusion with lysosomes in cells [14, 28]. Likewise, silencing ATG4 and treatment with tioconazole decreased the co-localization of LC3 and LAMP1, which are typical markers of autophagosomes and lysosomes, respectively (FIGS. 23, 60 and 61). In addition, since both autophagy inducers and a block in downstream steps increases the levels of LC3-II and autophagosomes, the differential amount of LC3-II between cells with and without autophagy inhibitor CQ was used to precisely measure LC3-II turnover [29], which is defined as autophagic flux. Immunoblotting results showed that silencing ATG4 or treatment with tioconazole significantly attenuated autophagic flux in cells, as indicated by decreases in the accumulation of LC3-II compared to cells without administrating with siATG4 or tioconazole (FIGS. 24-26). These results indicate that tioconazole may inhibit ATG4 to result in the accumulation of LC3-II and impair the fusion of autophagosomes and lysosomes, which, in turn, diminishes autophagic activity.

Figure 33:
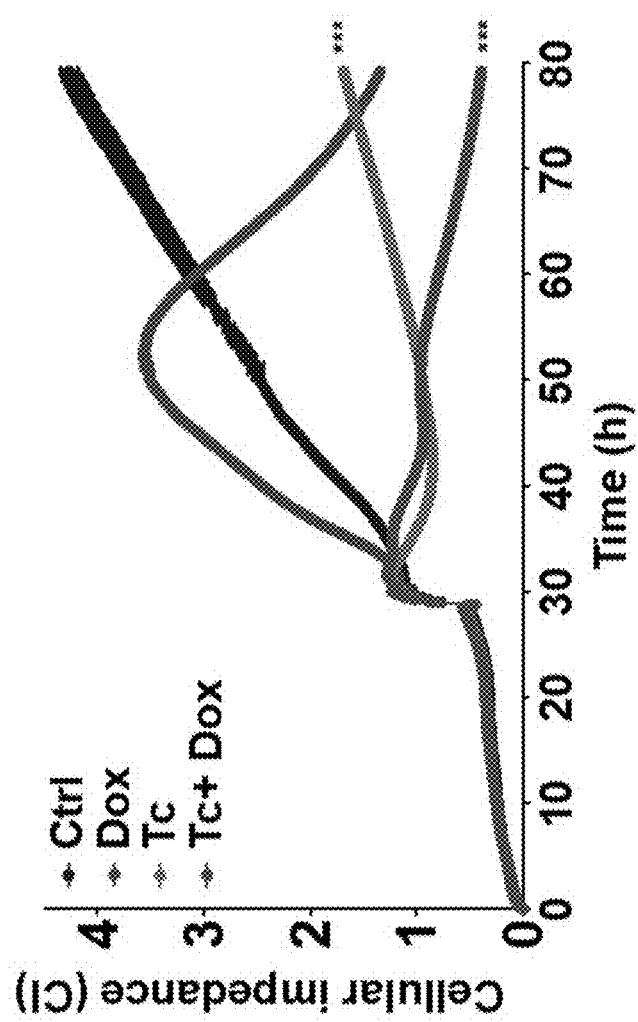
Figure 34:
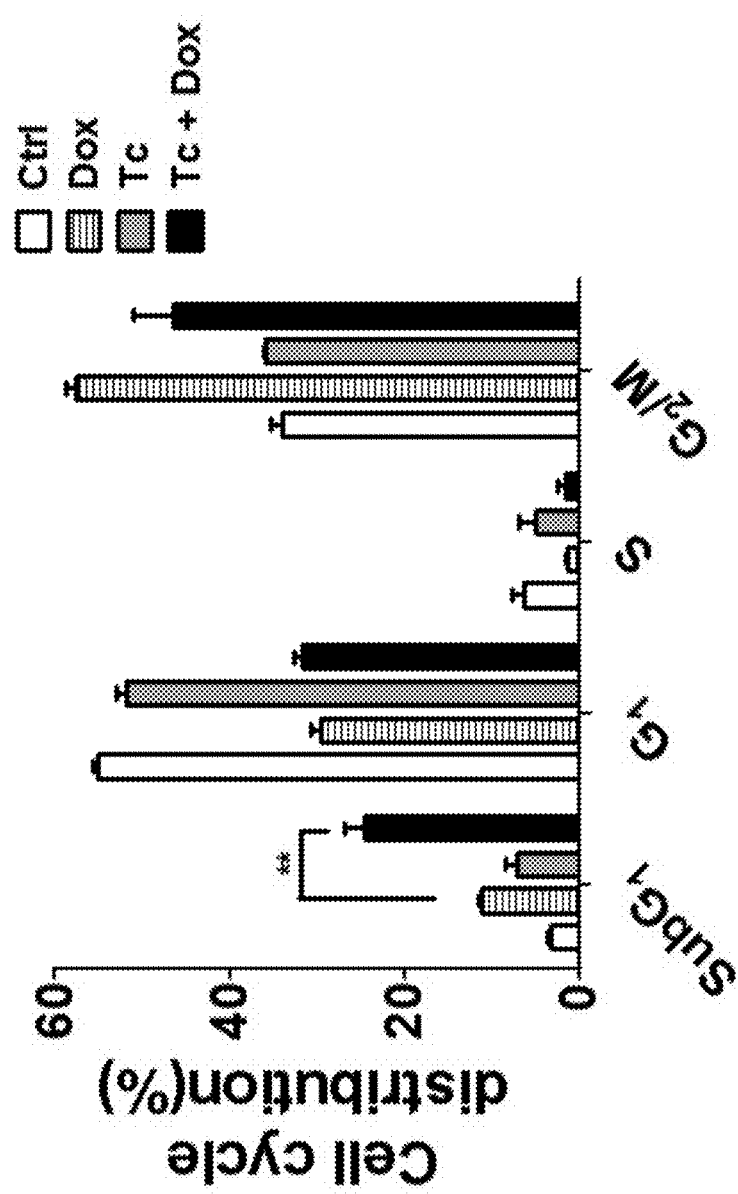
Figure 35:
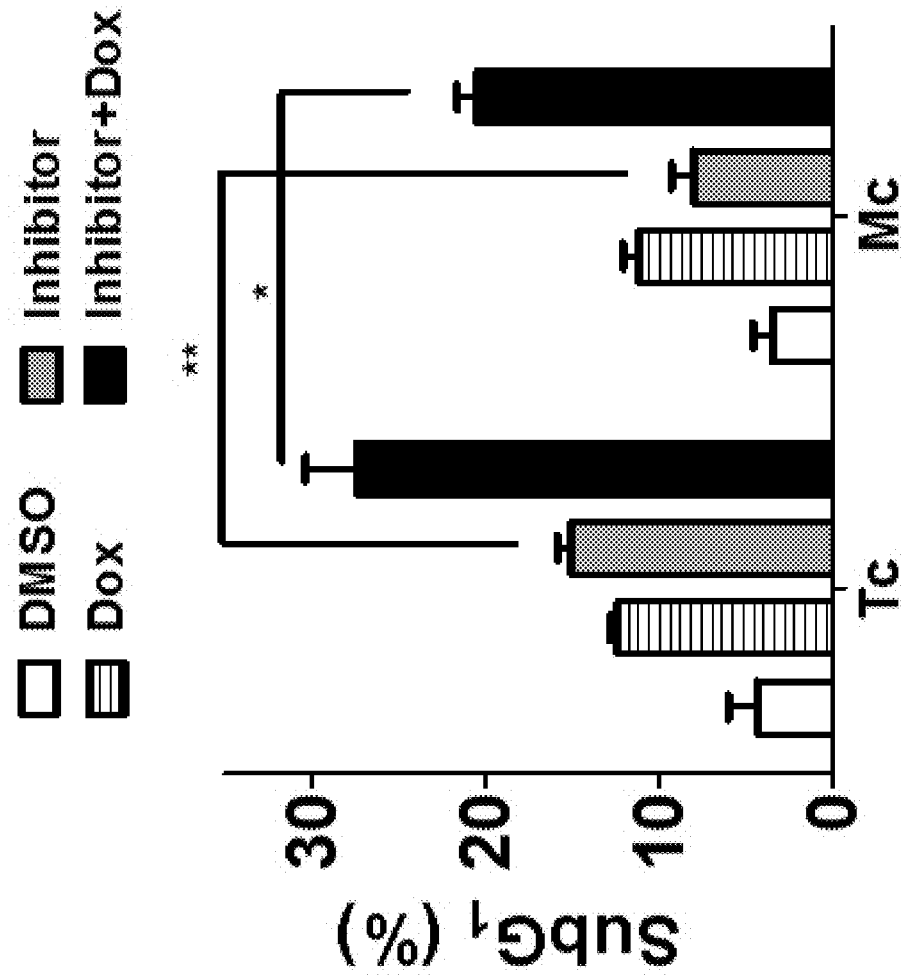
Figure 36:
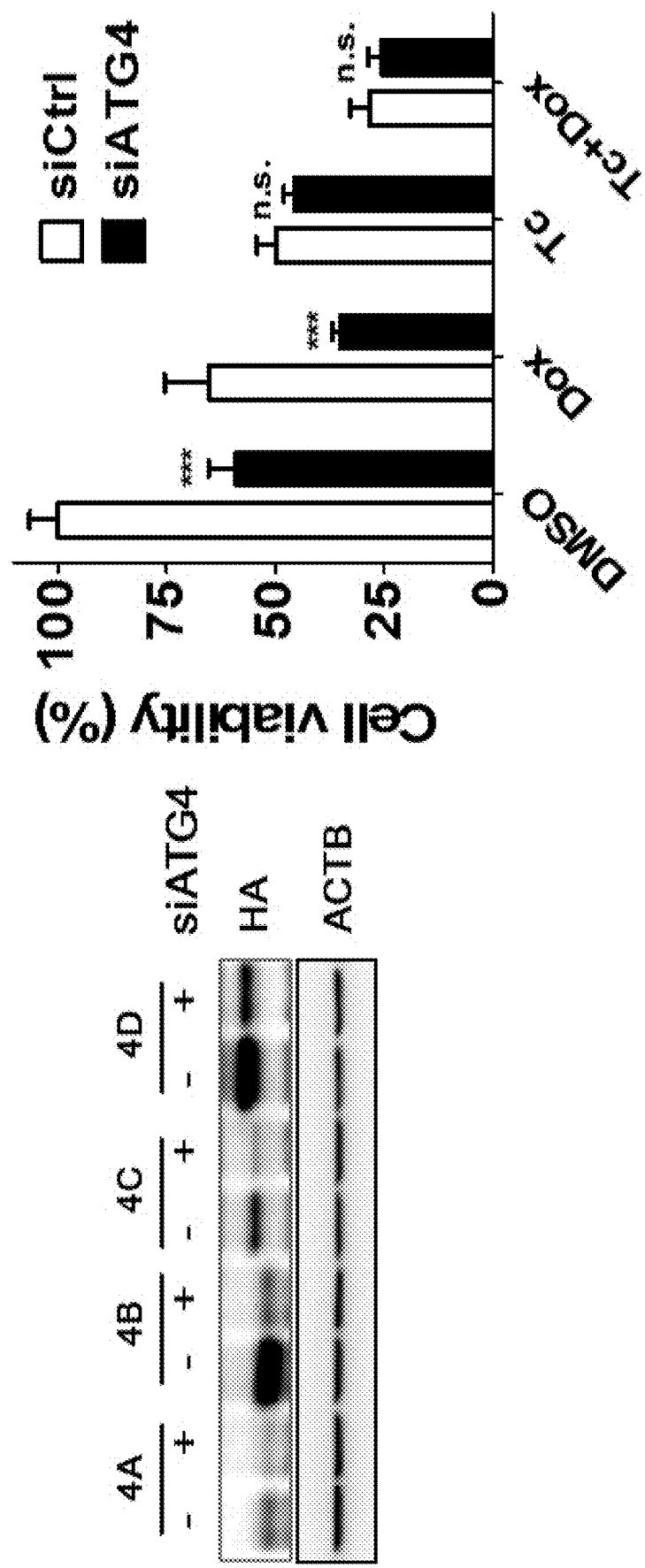
Figure 37:
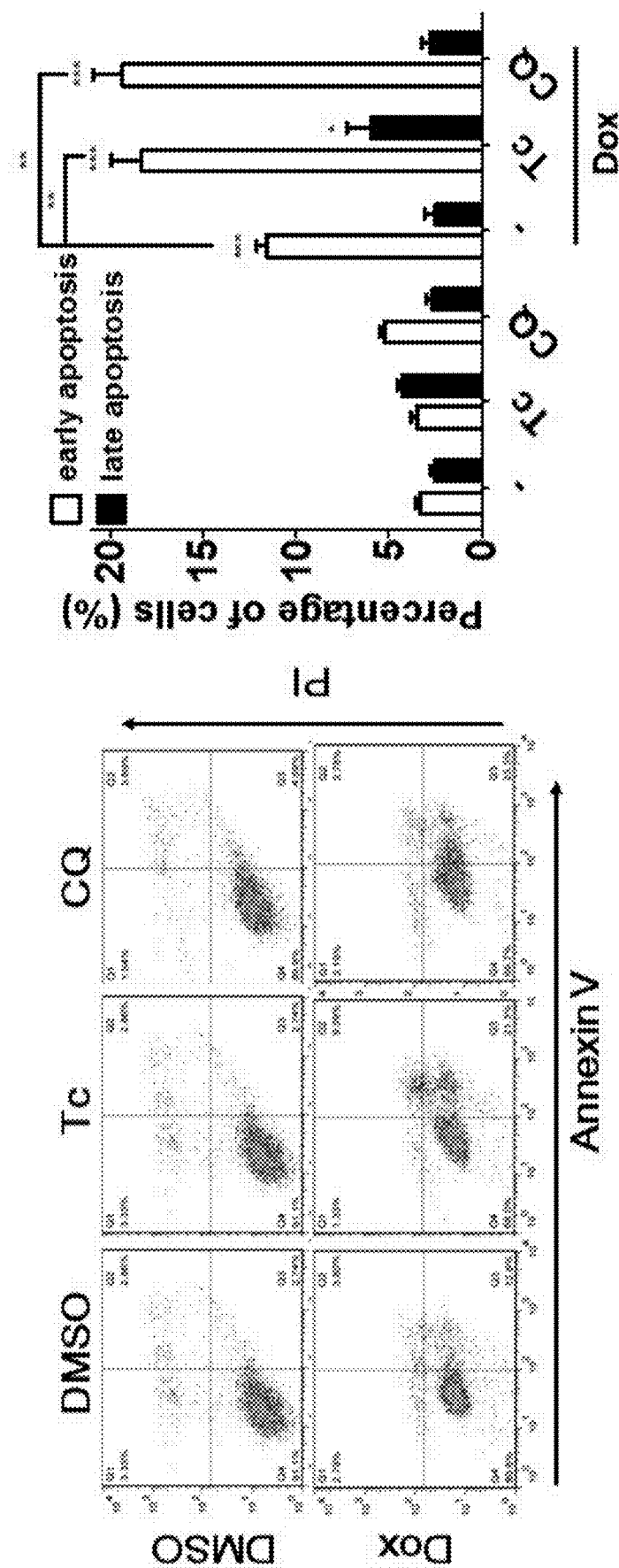
FIGS. 37-43 show the effects of tioconazole on chemotherapy-induced apoptosis in cancer cells.
Figure 38:
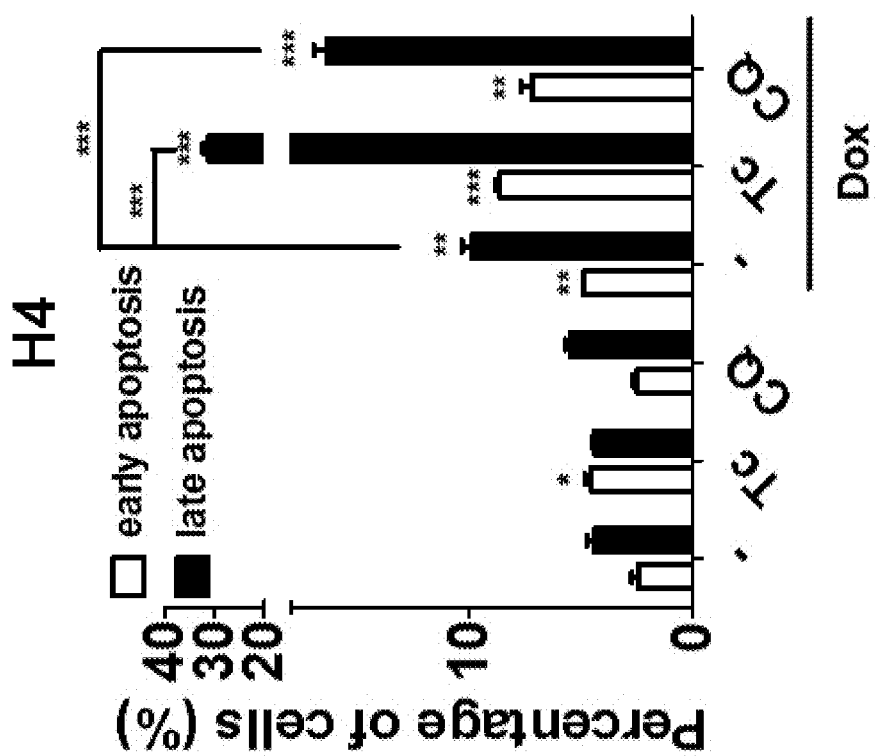
Figure 39:
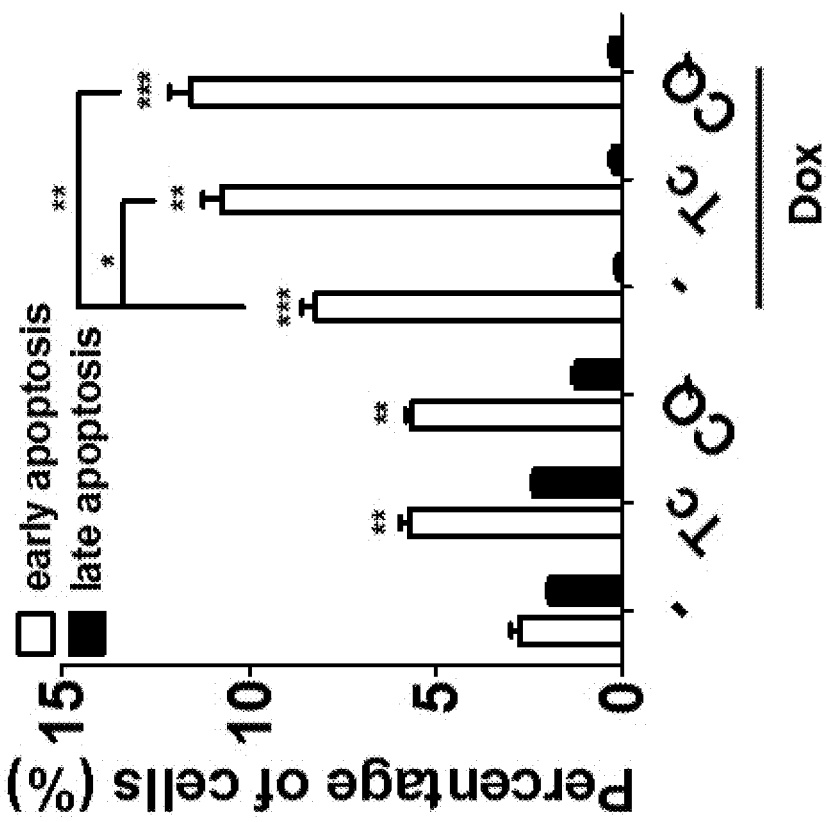

Example 4: Tioconazole Sensitizes Cancer Cells to Starvation and Chemotherapeutic Drugs Induced autophagy plays an important role in the resistance to starvation and chemotherapy in cancer cells [6, 30, 31]. To assess the effects of tioconazole on the autophagy inhibition and cytotoxicity in cancer cells during treatment of starvation or chemotherapeutic drugs, the levels of autophagy maker LC3-II and adaptor sequestosome-1 (SQSTM1, also known as p62) were examined by immunoblotting (FIG. 27-32) and cell viability was estimated based on the cellular ATP levels (FIGS. 27-32 and 73-76) or cellular impedance (FIG. 33). Tioconazole blocked LC3-II turnover and SQSTM1 degradation, which was triggered by starvation and chemotherapeutic drugs in cancer cells (FIG. 27-32). Tioconazole significantly reduced the cell viability and enhanced the cytotoxic effects of starvation and chemotherapy in cancer cell lines (FIGS. 27-33 and 73-76). Combined treatment with tioconazole and Dox synergistically increased cell death compared with cells treated with either Dox or tioconazole alone, as indicated by the subG1 proportion (FIG. 34). As observed for tioconazole and its analog miconazole in vitro (FIG. 4), miconazole less potently synergized with Dox to result in tumor cell death (FIG. 35). Moreover, silencing ATG4 using siRNA reduced tumor viability and synergistically enhanced Dox-induced cell death, whereas it did not further enhance the effects of tioconazole (FIG. 36).

Figure 40:
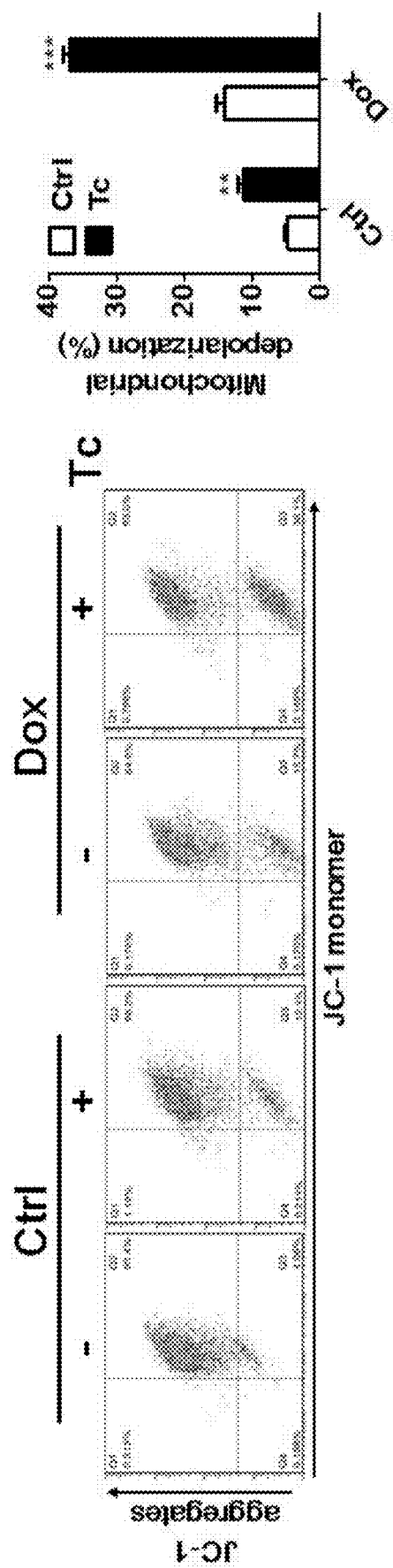
Figure 41:
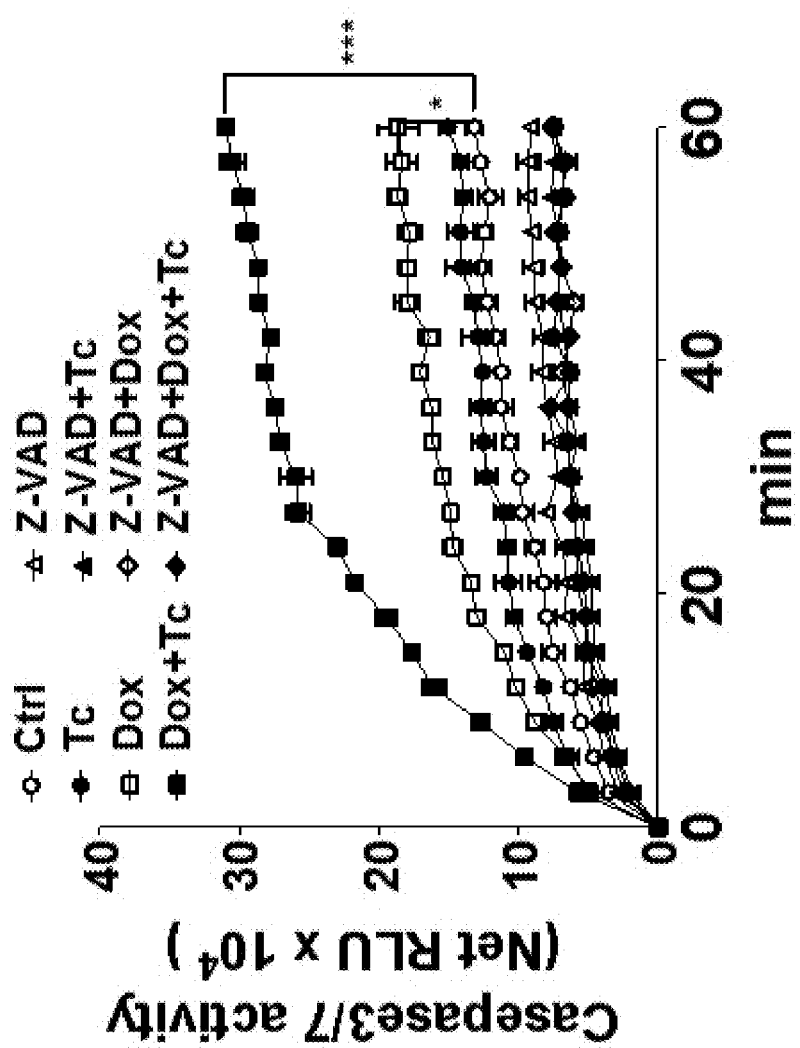
Figure 42:
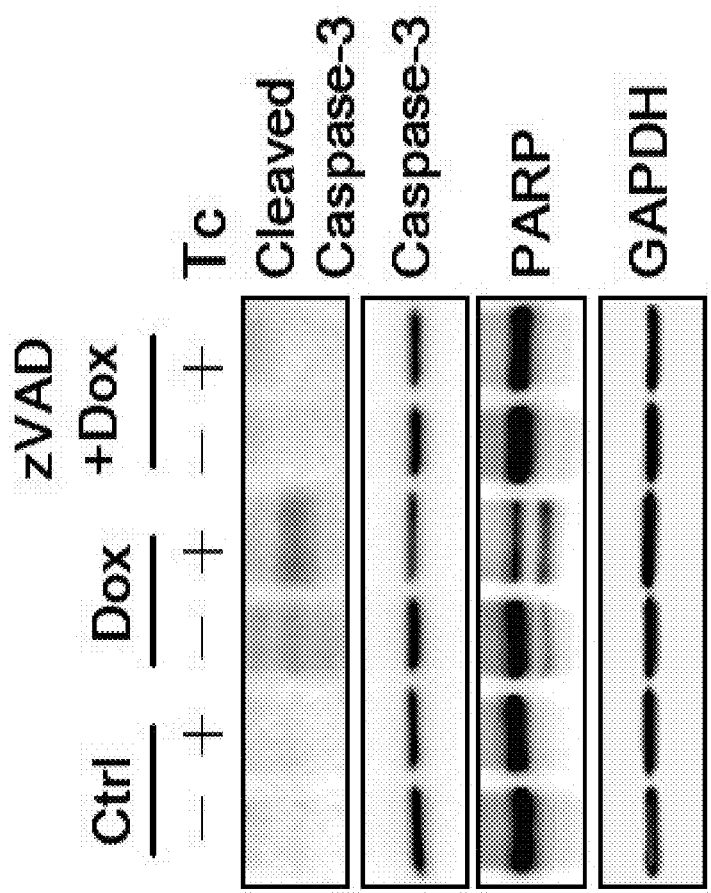
Figure 43:
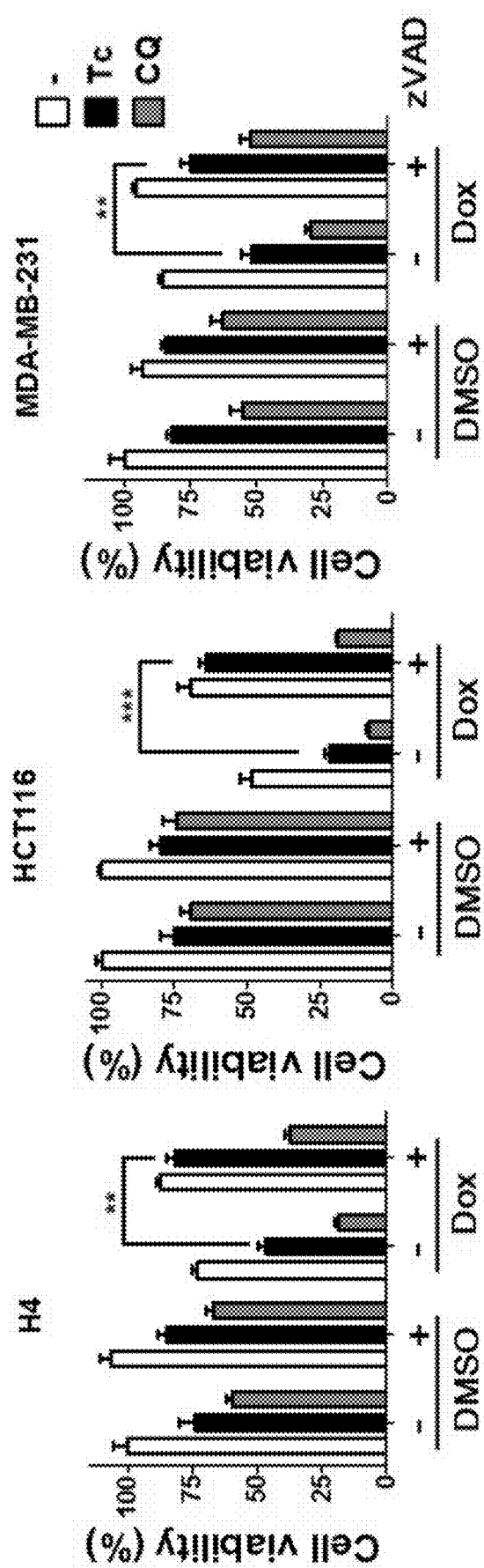

Autophagy serves as a defense mechanism in cancer cells in response to chemotherapy-induced apoptosis. Thus, we further examined the effect of tioconazole on apoptosis in cancer cells treated with Dox. Similar to the autophagy inhibitor CQ, tioconazole increased the percentage of early apoptotic (AV+PI−) in the Dox-treated HCT116, MDA-MB-231 and H4 cells (FIGS. 37-39 and 67-69), likely due to reduction of mitochondrial membrane potential (MMP) in these cells (FIGS. 40 and 69). In addition, caspase-3/7 activity and cleavage of caspase-3 and its substrate poly (ADP-ribose) polymerase (PARP) were significantly elevated in cells exposed to Dox alone or co-treated with tioconazole (FIG. 41-42). Pretreatment with z-VAD-fmk blocked caspase-3 activation and rescued the apoptotic effects in tumor cell cultures treated with tioconazole and Dox (FIG. 43). Overall, these results indicated that tioconazole sensitizes tumor cell lines to chemotherapeutic drug-induced apoptosis.

Figure 44:
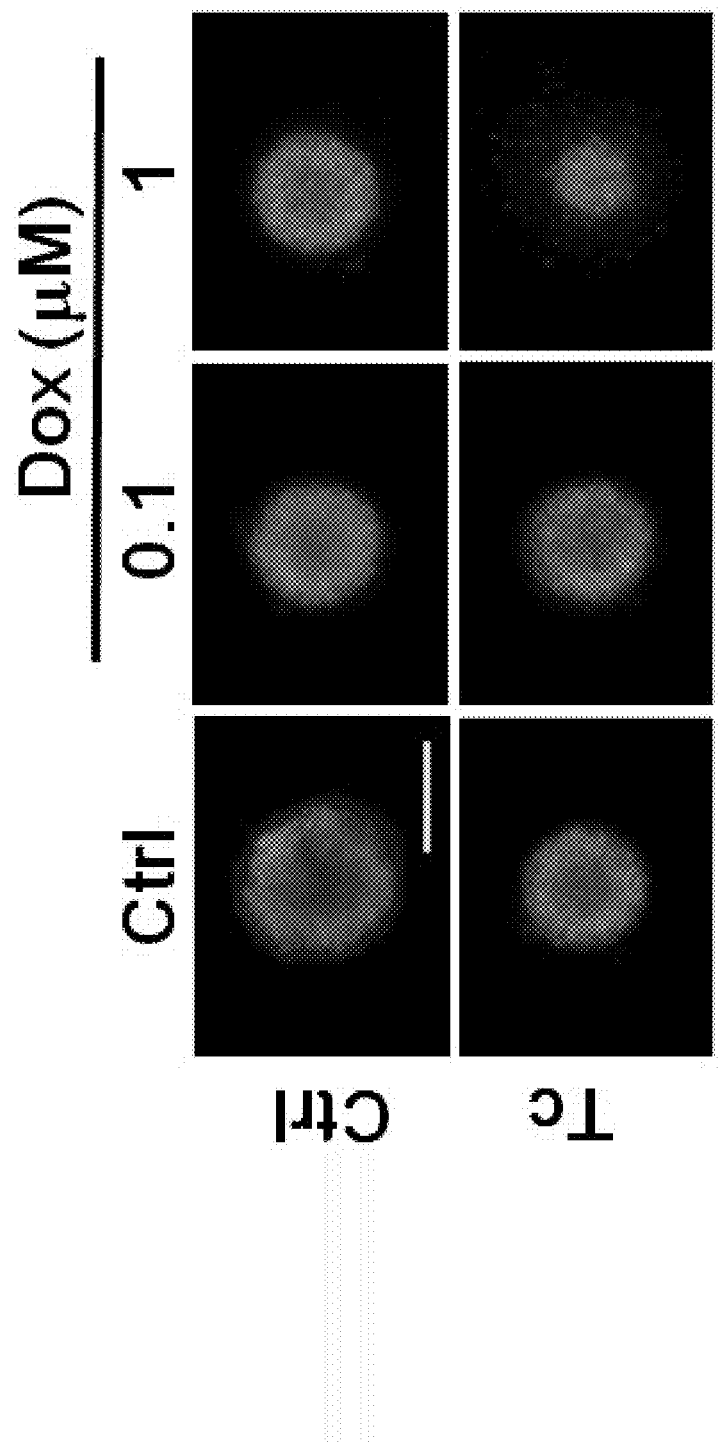
FIGS. 44-54 show the effects of tioconazole on chemosensitivity in tumor spheroid culture and xenograft mouse model.
Figure 45:
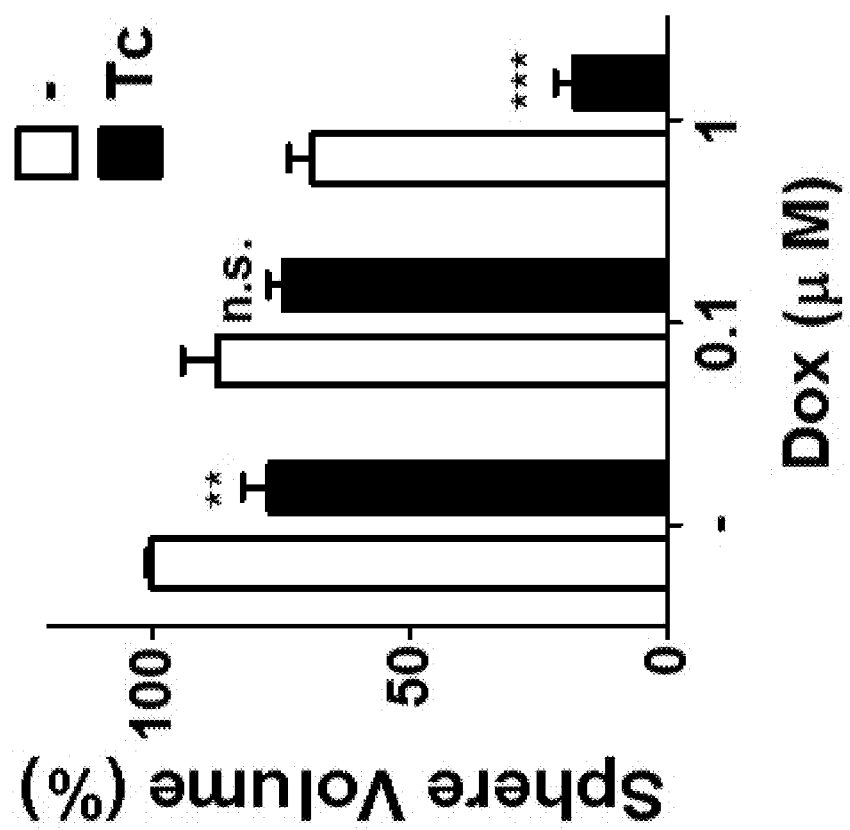
Figure 46:
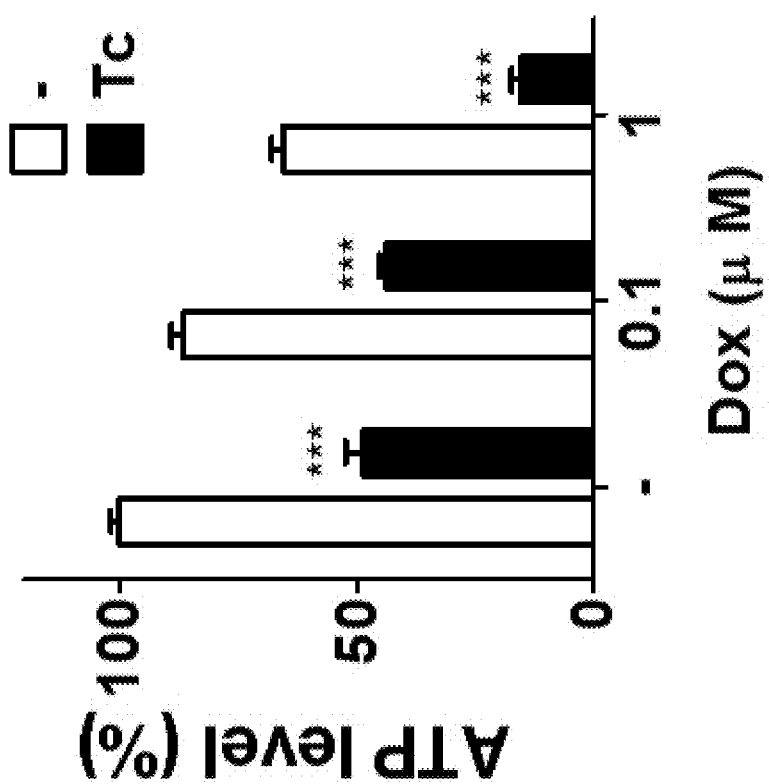
Figure 47:
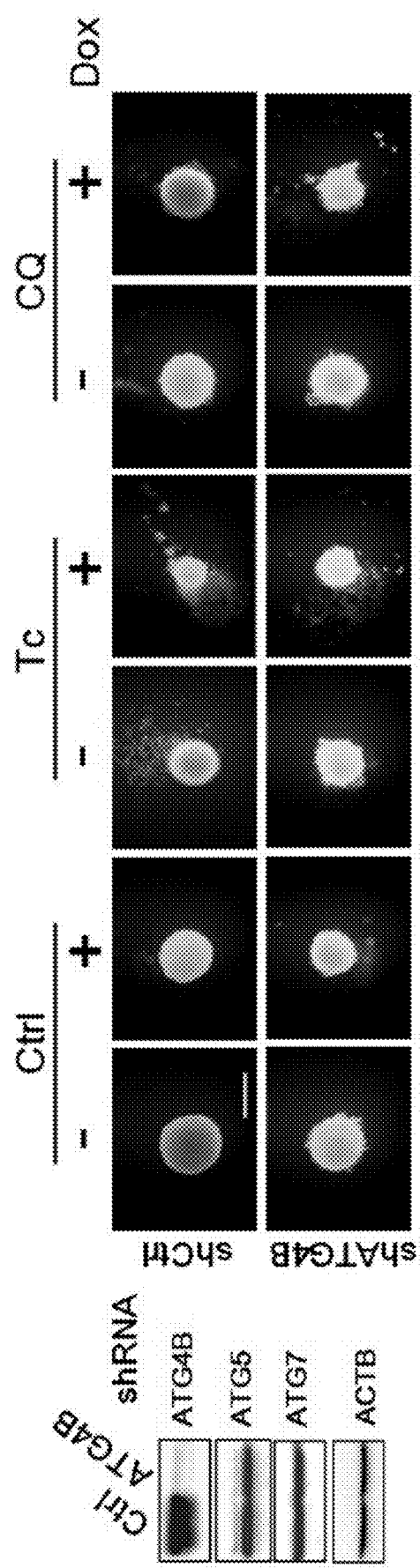
Figure 48:
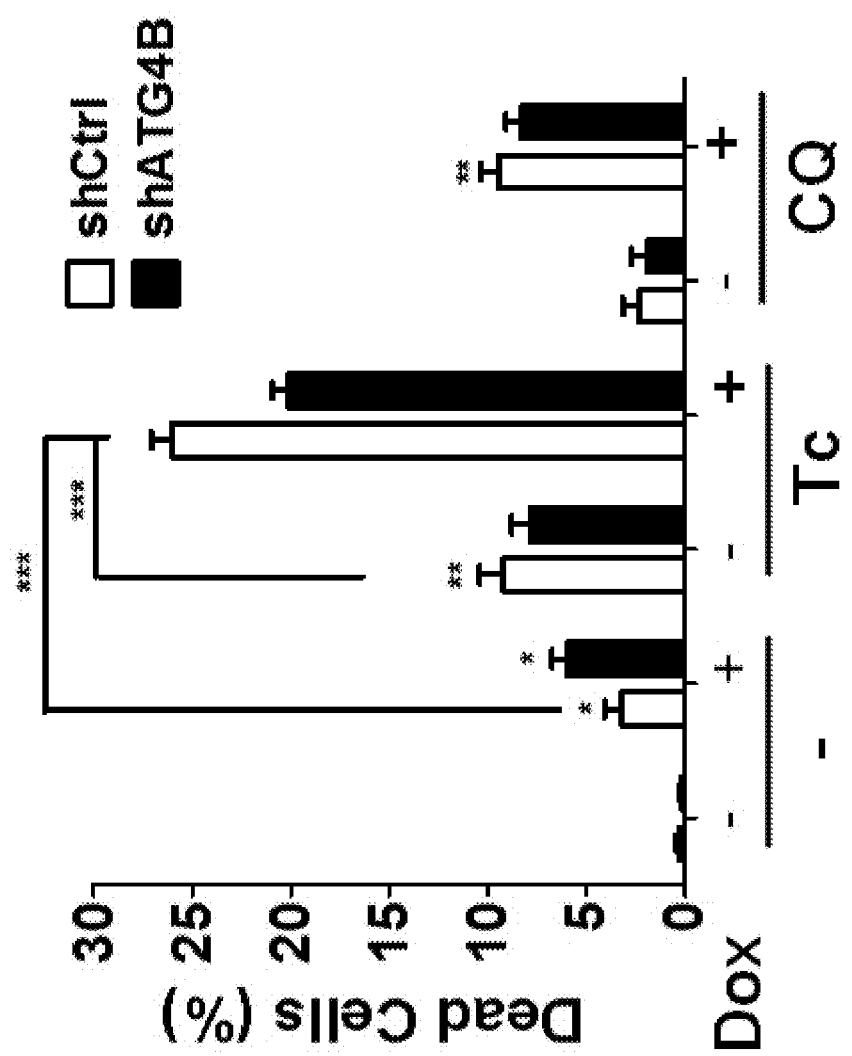

Example 5: Tioconazole Enhances Chemotherapy Efficacy in Spheroid Cell Culture and Xenografted Tumors To precisely assess the effects of tioconazole in tumors, HCT116 cells were cultured as spheroids and then treated with tioconazole alone or in combination with Dox (FIG. 44-46). Tioconazole significantly decreased the size of tumor spheroids and enhanced the cytotoxicity of Dox, as assessed based on the ATP levels and number of dead cells (FIG. 44-54). Moreover, tioconazole enhanced Dox-induced cell death both in cells treated with scramble shRNA and shRNA against ATG4B (FIGS. 47 and 48). Single ATG gene knockdown is likely not sufficient to block autophagy, as previously reported [32], which may explain why tioconazole appears to be more potent than ATG4B shRNA.

Figure 49:
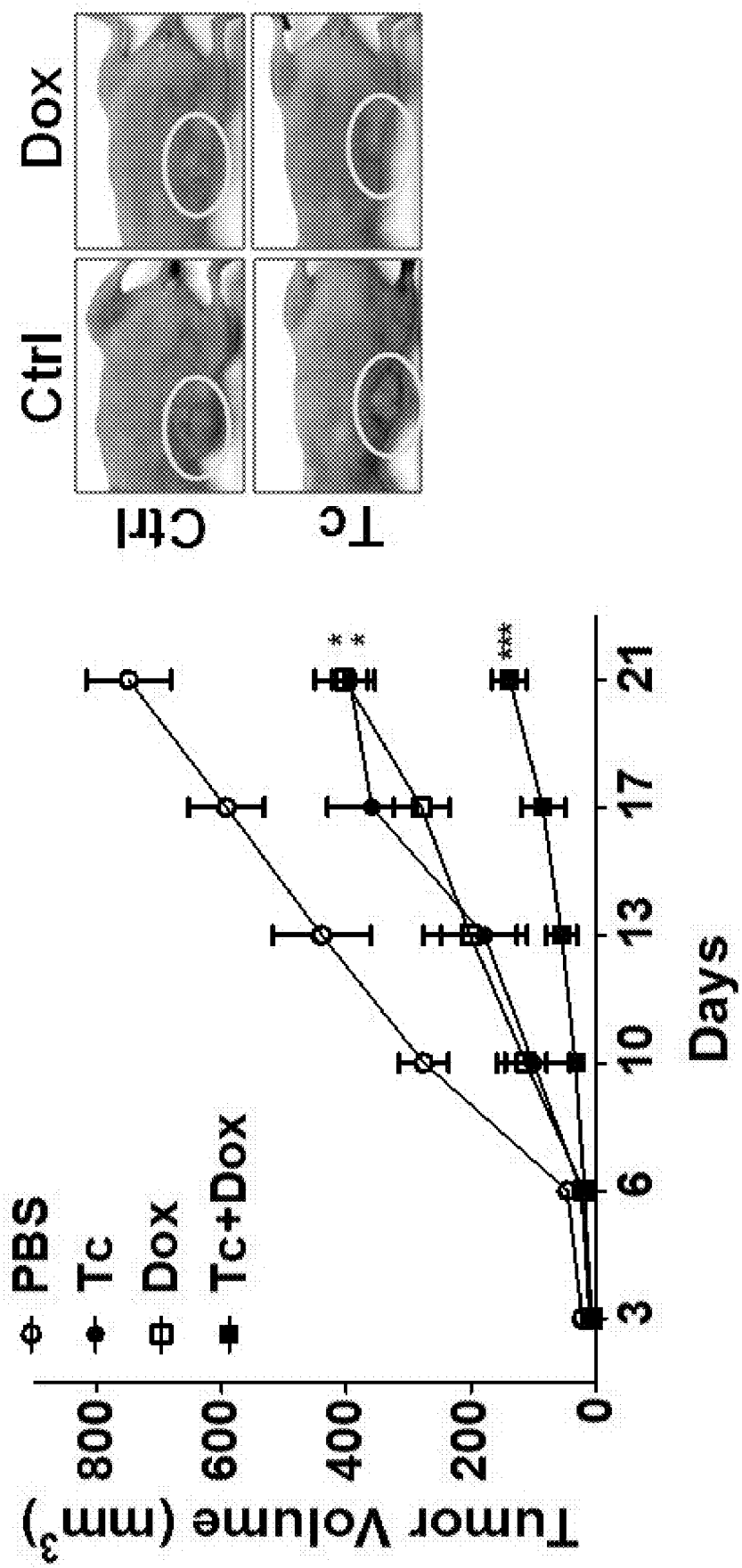
Figure 50:
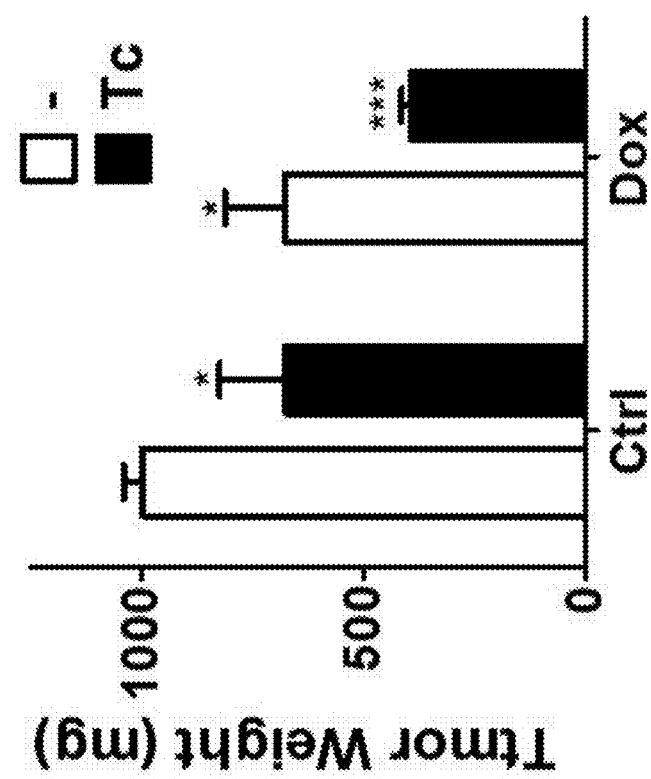
Figure 50:
Figure 51:
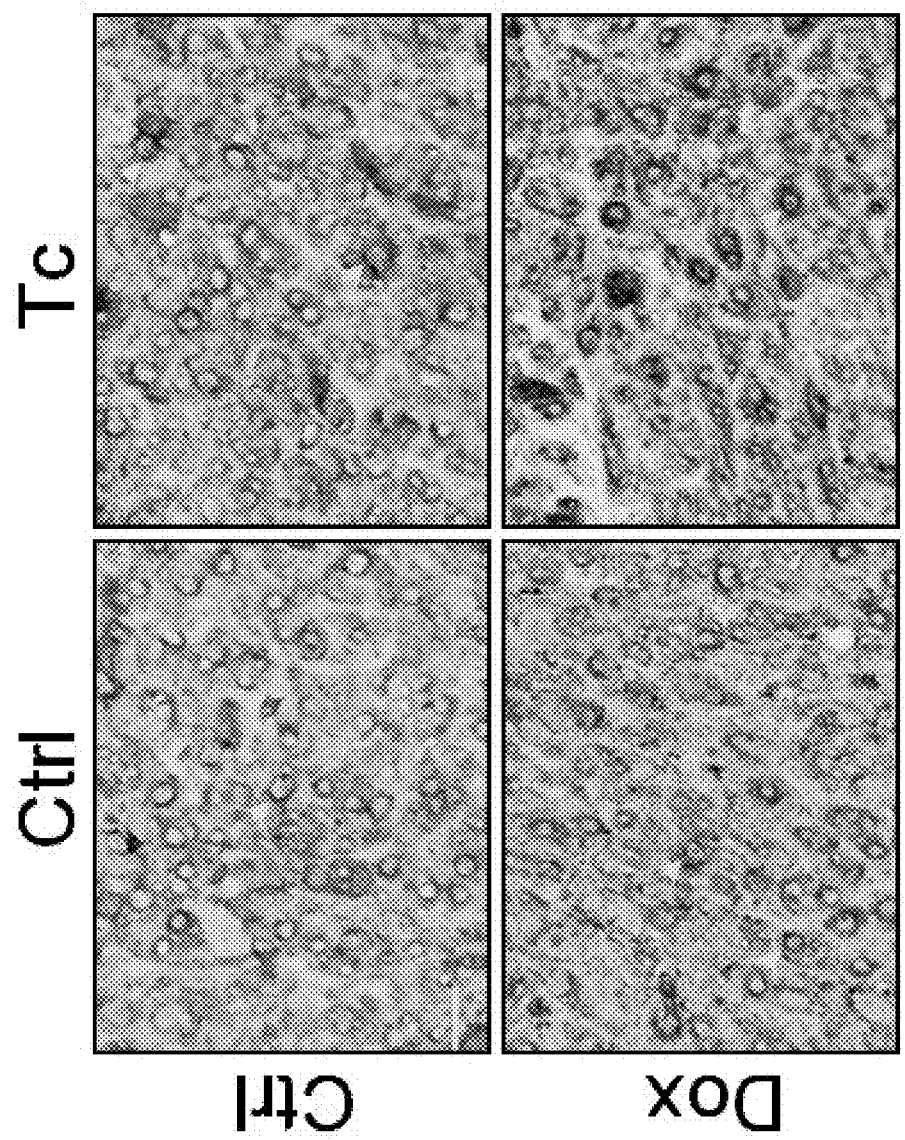
Figure 52:
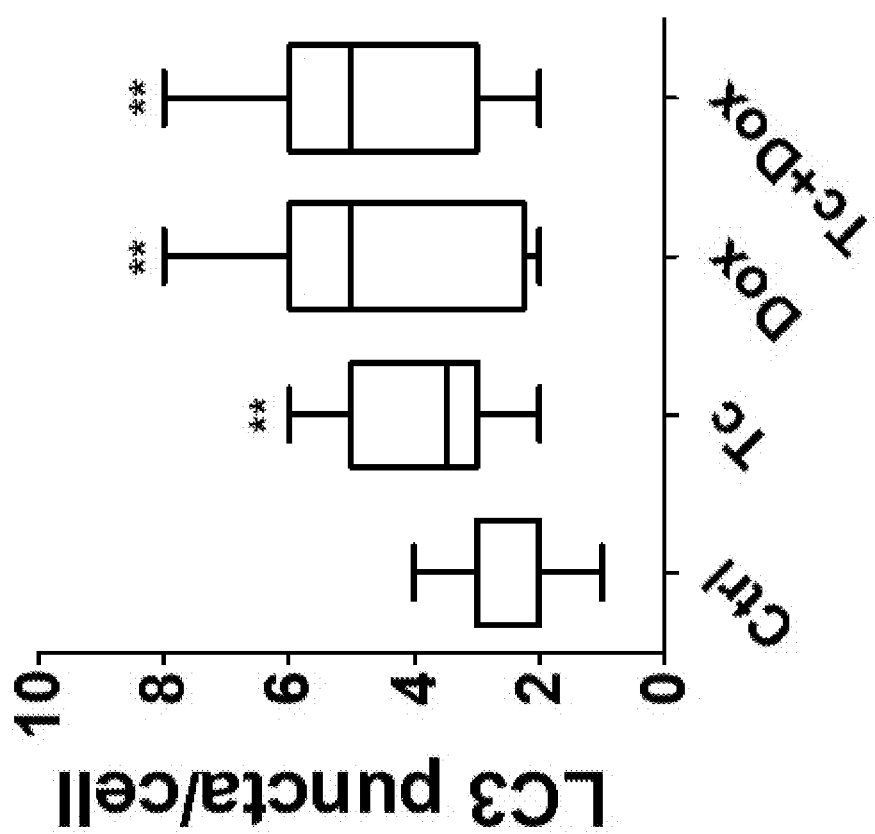
Figure 53:
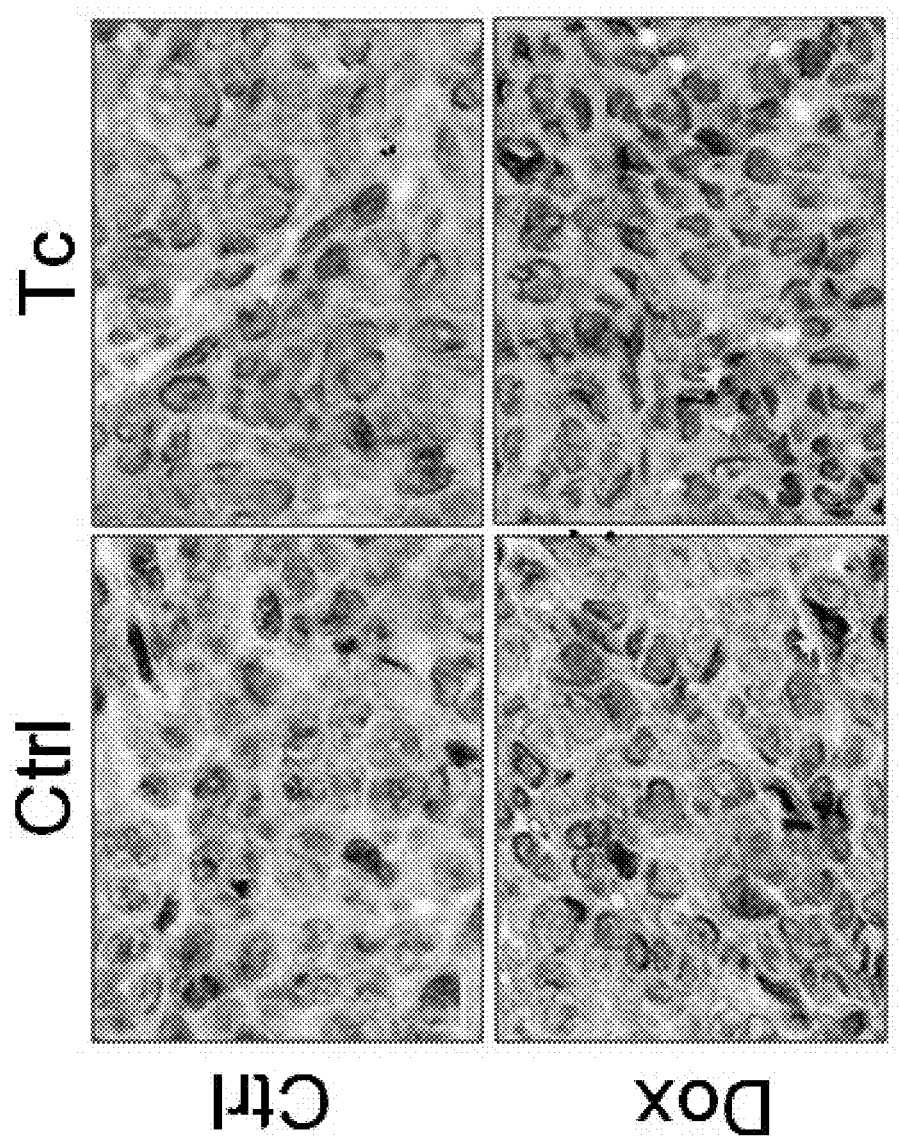
Figure 54:
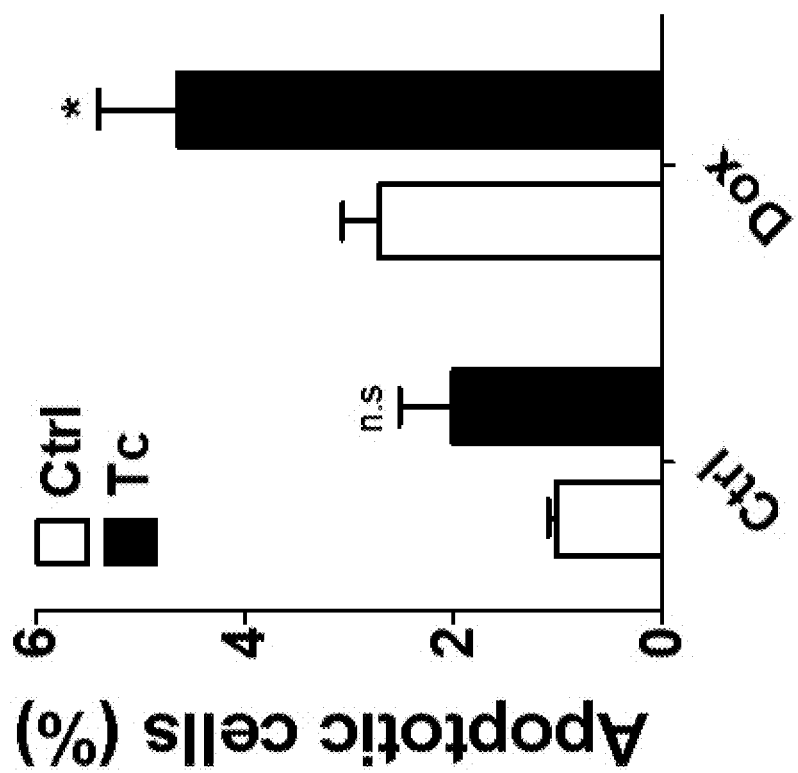
Figure 55:
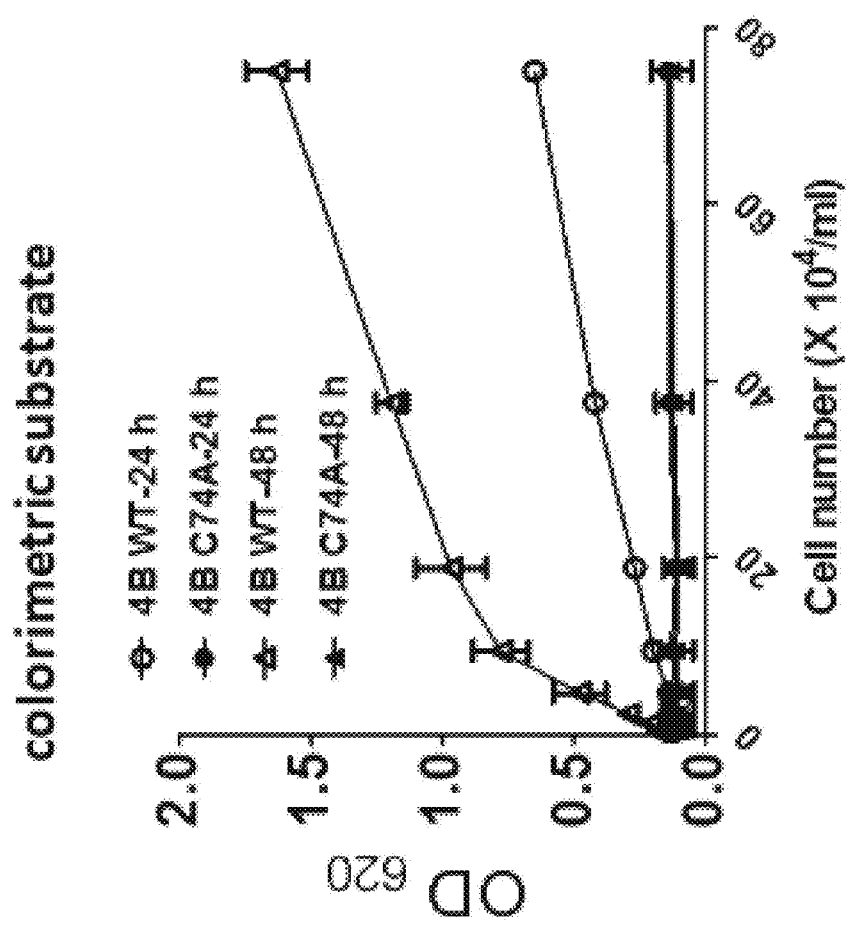
FIGS. 55-58 show the characterization of yeast based ATG4B reporter assay for hts.
Figure 56:
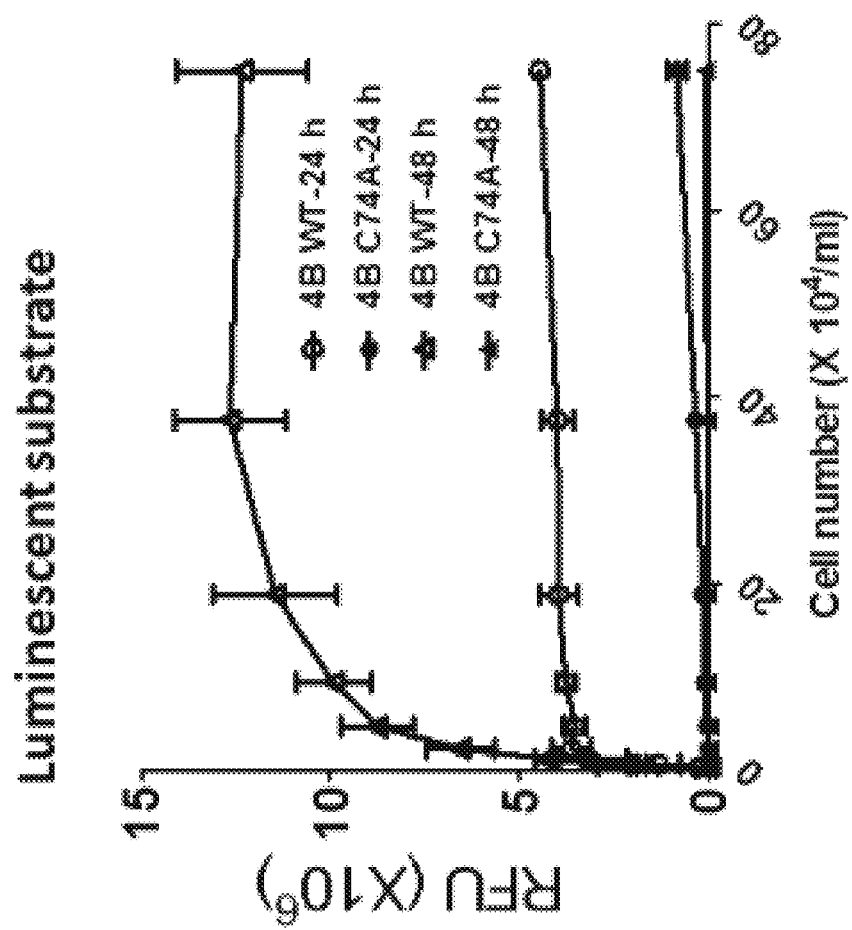
Figure 57:
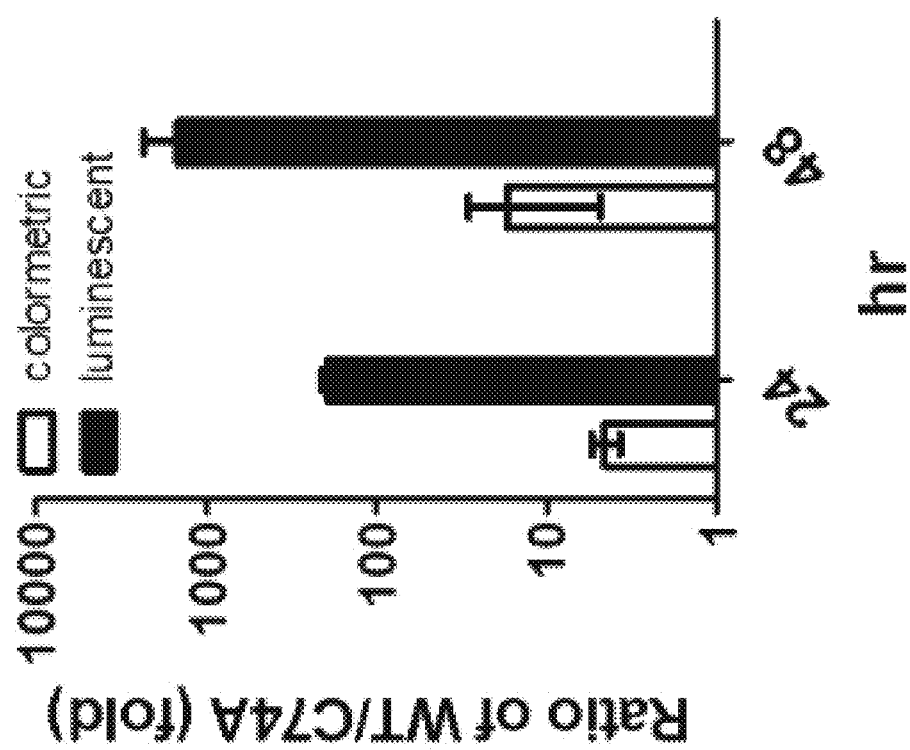
Figure 58:
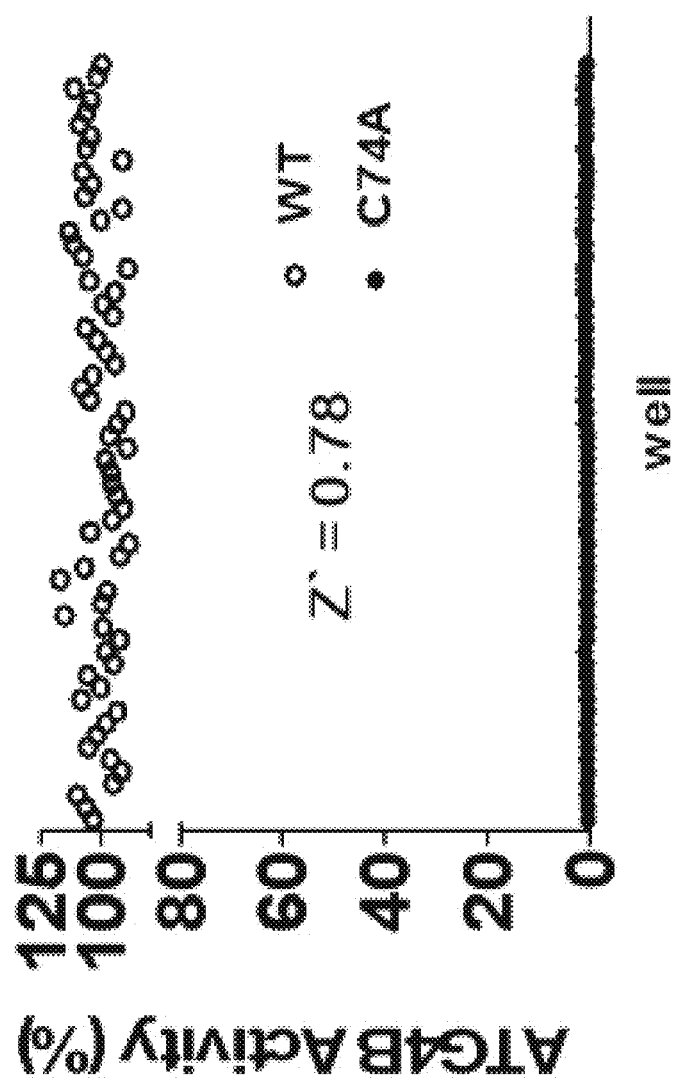

To assess the antitumor effects of tioconazole in vivo, HCT116 cells were xenografted into nude mice, and the animals were treated with tioconazole alone or in combination with Dox (FIGS. 49 and 50). Tioconazole reduced the xenograft tumor weight and sensitized xenograft tumors to Dox (FIG. 50). Moreover, the number of LC3 puncta and levels of cleaved caspase-3 were significantly increased in tumor tissues of the tioconazole-treated mice (FIG. 51-54). Overall, these findings are consistent with the cell culture model and support the notion that tioconazole may inhibit ATG4 and autophagy to enhance chemotherapy efficacy.

OTHER EMBODIMENTS

The invention includes embodiments in which exactly one member of the group is present in, employed in, or otherwise relevant to a given product or process. The invention includes embodiments in which more than one, or all of the group members are present in, employed in, or otherwise relevant to a given product or process. All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, those skilled in the art will recognize, or be able to ascertain by using no more than routine experimentation, many equivalents to the specific embodiments of the invention, described herein. For example, compounds structurally analogous to the compounds of this invention also can be made, screened for their modulating activities to ATG4 and treating ATG4 associated conditions. Thus, other embodiments are also within the claims. The scope of the present invention is not intended to be limited to the particular embodiments disclosed, but rather includes all embodiments falling within the scope of the appended claim. In addition, many modifications will be appreciated to adapt a particular instrument, situation or material to the teachings of the invention without departing from the essential scope thereof.

REFERENCE

1. Mizushima N, Klionsky D J. Protein turnover via autophagy: implications for metabolism. Annu Rev Nutr. 2007; 27:19-40.
2. Galluzzi L, Pietrocola F, Bravo-San Pedro J M, et al. Autophagy in malignant transformation and cancer progression. EMBO J. 2015; 34:856-880.
3. Jiang P, Mizushima N. Autophagy and human diseases. Cell Res. 2014; 24:69-79.
4. Renna M, Jimenez-Sanchez M, Sarkar S, et al. Chemical inducers of autophagy that enhance the clearance of mutant proteins in neurodegenerative diseases. J Biol Chem. 2010; 285:11061-11067.
5. Abedin M J, Wang D, McDonnell M A, et al. Autophagy delays apoptotic death in breast cancer cells following DNA damage. Cell Death Differ. 2007; 14:500-510.
6. Levy J M, Thompson J C, Griesinger A M, et al. Autophagy inhibition improves chemosensitivity in BRAF(V600E) brain tumors. Cancer Discov. 2014; 4:773-780.
7. Shi C S, Shenderov K, Huang N N, et al. Activation of autophagy by inflammatory signals limits IL-1beta production by targeting ubiquitinated inflammasomes for destruction. Nat Immunol. 2012; 13:255-263.
8. Yang Z J, Chee C E, Huang S, et al. Autophagy modulation for cancer therapy. Cancer Biol Ther. 2011; 11:169-176.
9. Solitro A R, MacKeigan J P. Leaving the lysosome behind: novel developments in autophagy inhibition. Future Med Chem. 2016; 8:73-86.
10. Maycotte P, Aryal S, Cummings C T, et al. Chloroquine sensitizes breast cancer cells to chemotherapy independent of autophagy. Autophagy. 2012; 8:200-212.
11. Maes H, Kuchnio A, Peric A, et al. Tumor vessel normalization by chloroquine independent of autophagy. Cancer Cell. 2014; 26:190-206.
12. Klionsky D J. Citing recent declines in the discovery of new ATG genes, some scientists now suggest that the end of autophagy research may be within sight. Autophagy. 2014; 10:715-716.
13. Nakatogawa H, Ishii J, Asai E, et al. Atg4 recycles inappropriately lipidated Atg8 to promote autophagosome biogenesis. Autophagy. 2012; 8:177-186.
14. Yu Z Q, Ni T, Hong B, et al. Dual roles of Atg8-PE deconjugation by Atg4 in autophagy. Autophagy. 2012; 8:883-892.
15. Marino G, Uria J A, Puente X S, et al. Human autophagins, a family of cysteine proteinases potentially implicated in cell degradation by autophagy. J Biol Chem. 2003; 278:3671-3678.
16. Schaaf M B, Keulers T G, Vooijs M A, et al. LC3/GABARAP family proteins: autophagy-(un)related functions. FASEB J. 2016; 30:3961-3978.
17. Li M, Hou Y, Wang J, et al. Kinetics comparisons of mammalian Atg4 homologues indicate selective preferences toward diverse Atg8 substrates. J Biol Chem. 2011; 286:7327-7338.
18. Shu C W, Drag M, Bekes M, et al. Synthetic substrates for measuring activity of autophagy proteases: autophagins (Atg4). Autophagy. 2010; 6:936-947.
19. Betin V M, Lane J D. Atg4D at the interface between autophagy and apoptosis. Autophagy. 2009; 5:1057-1059.
20. Trott O, Olson A J. AutoDock Vina: improving the speed and accuracy of docking with a new scoring function, efficient optimization, and multithreading. J Comput Chem. 2010; 31:455-461.
21. Chang C E, Chen W, Gilson M K. Ligand configurational entropy and protein binding. Proc Natl Acad Sci USA. 2007; 104:1534-1539.
22. Tsui V, Case D A. Theory and applications of the generalized Born solvation model in macromolecular simulations. Biopolymers. 2000; 56:275-291.
23. Hayashi H, Cuddy M, Shu V C, et al. Versatile assays for high throughput screening for activators or inhibitors of intracellular proteases and their cellular regulators. PLoS One. 2009; 4:e7655.
24. Akin D, Wang S K, Habibzadegah-Tari P, et al. A novel ATG4B antagonist inhibits autophagy and has a negative impact on osteosarcoma tumors. Autophagy. 2014; 10:2021-2035.
25. Morris G M, Huey R, Lindstrom W, et al. AutoDock4 and AutoDockTools4: Automated docking with selective receptor flexibility. J Comput Chem. 2009; 30:2785-2791.
26. Bortnik S, Choutka C, Horlings H M, et al. Identification of breast cancer cell subtypes sensitive to ATG4B inhibition. Oncotarget. 2016.
27. Fujita N, Hayashi-Nishino M, Fukumoto H, et al. An Atg4B mutant hampers the lipidation of LC3 paralogues and causes defects in autophagosome closure. Mol Biol Cell. 2008; 19:4651-4659.
28. Betin V M, Singleton B K, Parsons S F, et al. Autophagy facilitates organelle clearance during differentiation of human erythroblasts: evidence for a role for ATG4 paralogs during autophagosome maturation. Autophagy. 2013; 9:881-893.
29. Klionsky D J, Abdelmohsen K, Abe A, et al. Guidelines for the use and interpretation of assays for monitoring autophagy (3rd edition). Autophagy. 2016; 12:1-222.
30. Egan D F, Chun M G, Vamos M, et al. Small Molecule Inhibition of the Autophagy Kinase ULK1 and Identification of ULK1 Substrates. Mol Cell. 2015; 59:285-297.
31. Weinberg S E, Chandel N S. Targeting mitochondria metabolism for cancer therapy. Nat Chem Biol. 2015; 11:9-15.
32. Nishida Y, Arakawa S, Fujitani K, et al. Discovery of Atg5/Atg7-independent alternative macroautophagy. Nature. 2009; 461:654-658.
33. Liu P F, Leung C M, Chang Y H, et al. ATG4B promotes colorectal cancer growth independent of autophagic flux. Autophagy. 2014; 10:1454-1465.
34. Rothe K, Lin H, Lin K B, et al. The core autophagy protein ATG4B is a potential biomarker and therapeutic target in CML stem/progenitor cells. Blood. 2014; 123: 3622-3634.
35. Satoo K, Noda N N, Kumeta H, et al. The structure of Atg4B-LC3 complex reveals the mechanism of LC3 processing and delipidation during autophagy. EMBO J. 2009; 28:1341-1350.

What is claimed is:

1. A method of treating a cancer comprising a step of administering a subject with an effective amount of tioconazole in combination with doxorubicin or camptothecin, wherein the cancer is colorectal cancer, neural glioma cancer, triple negative breast cancer, gastric cancer, or pancreatic cancer.

2. The method of claim 1, wherein the cancer is colorectal cancer.

3. The method of claim 1, wherein the cancer is neural glioma cancer.

4. The method of claim 1, comprising the step of administering a subject with an effective amount of tioconazole in combination with doxorubicin.

5. The method of claim 1, comprising the step of administering a subject with an effective amount of tioconazole in combination with camptothecin.

6. The method of claim 1, wherein said administration inhibits the activity of ATG4.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: forward primer for Real-Time PCR of ATG4A

<400> SEQUENCE: 1
tgctggttgg ggatgtatgc                                           20

<210> SEQ ID NO 2
<211> LENGTH: 22
<212> TYPE: DNA
<213> ORGANISM: Artificial Sequence
<220> FEATURE:
<223> OTHER INFORMATION: Reverse primer for Real-Time PCR of ATG4A

<400> SEQUENCE: 2
gcgttggtat tctttgggtt gt                                        22

<210> SEQ ID NO 3
<211> LENGTH: 21
<212> TYPE: DNA
<213> ORGANISM: Artificial Sequence
<220> FEATURE:
<223> OTHER INFORMATION: forward primer for Real-Time PCR of ATG4B

<400> SEQUENCE: 3
gatagcgcaa atgggagttg g                                         21

<210> SEQ ID NO 4
<211> LENGTH: 21
<212> TYPE: DNA
<213> ORGANISM: Artificial Sequence
<220> FEATURE:
<223> OTHER INFORMATION: Reverse primer for Real-Time PCR of ATG4B

<400> SEQUENCE: 4
ccacgtatcg aagacagcaa g                                         21

<210> SEQ ID NO 5
<211> LENGTH: 23
<212> TYPE: DNA
<213> ORGANISM: Artificial Sequence
<220> FEATURE:
<223> OTHER INFORMATION: forward primer for Real-Time PCR of ATG4C

<400> SEQUENCE: 5
tagaggatca cgtaattgca gga                                       23

<210> SEQ ID NO 6
<211> LENGTH: 23
<212> TYPE: DNA
<213> ORGANISM: Artificial Sequence
<220> FEATURE:
<223> OTHER INFORMATION: Reverse primer for Real-Time PCR of ATG4C

<400> SEQUENCE: 6
gttgtcaaag ctgagccttc tat                                       23

<210> SEQ ID NO 7
<211> LENGTH: 21
<212> TYPE: DNA
<213> ORGANISM: Artificial Sequence

```
-continued

<220> FEATURE:
<223> OTHER INFORMATION: forward primer for Real-Time PCR of ATG4D

<400> SEQUENCE: 7
ggaacaacgt caagtacggt t                                              21

<210> SEQ ID NO 8
<211> LENGTH: 19
<212> TYPE: DNA
<213> ORGANISM: Artificial Sequence
<220> FEATURE:
<223> OTHER INFORMATION: Reverse primer for Real-Time PCR of ATG4D

<400> SEQUENCE: 8
ctcgccctcg aaacggtag                                                 19
```